US009445713B2

(12) United States Patent
Douglas et al.

(10) Patent No.: US 9,445,713 B2
(45) Date of Patent: Sep. 20, 2016

(54) APPARATUSES AND METHODS FOR MOBILE IMAGING AND ANALYSIS

(71) Applicant: CellScope, Inc., San Francisco, CA (US)

(72) Inventors: Erik Scott Douglas, Oakland, CA (US); Daniel Irving Golden, Palo Alto, CA (US); Christopher Todd Fox, Mill Valley, CA (US); Thomas Burnell Reeve, San Francisco, CA (US); Janakiramanan Ramachandran, Fremont, CA (US)

(73) Assignee: CellScope, Inc., San Francisco, CA (US)

( * ) Notice: Subject to any disclaimer, the term of this patent is extended or adjusted under 35 U.S.C. 154(b) by 0 days.

(21) Appl. No.: 14/479,225

(22) Filed: Sep. 5, 2014

(65) Prior Publication Data
US 2015/0065803 A1   Mar. 5, 2015

Related U.S. Application Data

(60) Provisional application No. 61/874,041, filed on Sep. 5, 2013, provisional application No. 61/988,281, filed on May 4, 2014, provisional application No. 62/008,493, filed on Jun. 5, 2014.

(51) Int. Cl.
*A61B 1/227* (2006.01)
*A61B 1/00* (2006.01)
(Continued)

(52) U.S. Cl.
CPC ........... *A61B 1/227* (2013.01); *A61B 1/00009* (2013.01); *A61B 1/00045* (2013.01); *G06K 9/6267* (2013.01); *G06T 7/0081* (2013.01);
(Continued)

(58) Field of Classification Search
CPC ................. A61F 11/00; A61F 11/004; A61B 2017/00787; A61B 1/2275; A61B 1/227
See application file for complete search history.

(56) References Cited

U.S. PATENT DOCUMENTS 5,202,758 A   4/1993   Tamburrino
5,982,559 A  11/1999   Furutake
(Continued)

FOREIGN PATENT DOCUMENTS

CN          2722826 Y    9/2005
KR       1020050006623   1/2005
(Continued)

OTHER PUBLICATIONS

Fletcher et al.; U.S. Appl. No. 14/301,506 entitled "High Numerical Aperture Telemicroscopy Apparatus," filed Jun. 11, 2014.
(Continued)

*Primary Examiner* — Eduardo C Robert
*Assistant Examiner* — Julianna N Harvey
(74) *Attorney, Agent, or Firm* — Shay Glenn LLP

(57) ABSTRACT

Apparatuses and methods for mobile imaging and image analysis. In particular, described herein are methods and apparatuses for assisting in the acquisition and analysis of images of the tympanic membrane to provide information that may be helpful in the understanding and management of disease, such ear infection (acute otitis media). These apparatuses may guide or direct a subject in taking an image of a tympanic membrane, including automatically detecting which direction to adjust the position of the apparatus to capture an image of the tympanic membrane and automatically indicating when the tympanic membrane has been imaged.

22 Claims, 46 Drawing Sheets

(51) Int. Cl.
*G06K 9/62* (2006.01)
*G06T 7/00* (2006.01)
*A61B 3/12* (2006.01)
*G06F 19/00* (2011.01)

(52) U.S. Cl.
CPC ............... *G06T 7/0087* (2013.01); *A61B 3/12* (2013.01); *G06F 19/321* (2013.01); *G06K 2209/05* (2013.01); *G06T 2207/30004* (2013.01)

(56) References Cited

U.S. PATENT DOCUMENTS

| | | | |
|---|---|---|---|
| 6,048,320 A * | 4/2000 | Brainard, II | 600/559 |
| 6,606,413 B1 | 8/2003 | Zeineh | |
| 6,790,178 B1 | 9/2004 | Mault et al. | |
| 6,950,241 B1 | 9/2005 | Liang | |
| 7,031,745 B2 | 4/2006 | Shen | |
| 7,802,909 B2 | 9/2010 | Baker | |
| 7,821,569 B2 | 10/2010 | Yang | |
| 8,253,787 B2 | 8/2012 | Yamamoto | |
| 8,743,194 B2 | 6/2014 | Fletcher et al. | |
| 8,786,695 B2 | 7/2014 | Fletcher et al. | |
| 2003/0078517 A1 | 4/2003 | Kensey | |
| 2003/0103262 A1 | 6/2003 | Descour et al. | |
| 2003/0164895 A1 | 9/2003 | Viinikanoja et al. | |
| 2004/0017620 A1 | 1/2004 | Kaneko et al. | |
| 2004/0062545 A1 | 4/2004 | Ushiro | |
| 2004/0184163 A1 | 9/2004 | Nishioka et al. | |
| 2005/0001144 A1 | 1/2005 | Cartlidge et al. | |
| 2005/0266839 A1 | 12/2005 | Paul et al. | |
| 2006/0222567 A1 | 10/2006 | Kloepfer et al. | |
| 2006/0233545 A1 | 10/2006 | Senba et al. | |
| 2006/0282009 A1 | 12/2006 | Oberg et al. | |
| 2006/0291842 A1 | 12/2006 | Tokiwa et al. | |
| 2007/0183930 A1 | 8/2007 | Roman | |
| 2007/0255115 A1 | 11/2007 | Anglin et al. | |
| 2007/0280677 A1 | 12/2007 | Drake | |
| 2008/0058629 A1 | 3/2008 | Seibel et al. | |
| 2008/0070599 A1 | 3/2008 | Apodaca et al. | |
| 2008/0146277 A1 | 6/2008 | Anglin et al. | |
| 2009/0185191 A1* | 7/2009 | Boppart et al. | 356/479 |
| 2009/0190822 A1 | 7/2009 | Ortyn et al. | |
| 2009/0203986 A1 | 8/2009 | Winnick | |
| 2009/0285283 A1 | 11/2009 | Gao et al. | |
| 2010/0033587 A1 | 2/2010 | Yumiki | |
| 2010/0042004 A1 | 2/2010 | Dhawan | |
| 2010/0056928 A1 | 3/2010 | Zuzak et al. | |
| 2010/0066892 A1 | 3/2010 | Momoki | |
| 2010/0191144 A1* | 7/2010 | Zoth et al. | 600/559 |
| 2011/0015496 A1 | 1/2011 | Sherman et al. | |
| 2011/0035234 A1 | 2/2011 | Roe et al. | |
| 2011/0085032 A1 | 4/2011 | Kim | |
| 2011/0181947 A1 | 7/2011 | Yang | |
| 2011/0224493 A1 | 9/2011 | Oyadiran et al. | |
| 2011/0234757 A1 | 9/2011 | Zheng et al. | |
| 2011/0292198 A1 | 12/2011 | Lapstun et al. | |
| 2011/0292199 A1 | 12/2011 | Lapstun et al. | |
| 2011/0294543 A1 | 12/2011 | Lapstun et al. | |
| 2012/0039593 A1 | 2/2012 | Yang | |
| 2012/0133825 A1 | 5/2012 | Nakajima et al. | |
| 2012/0236424 A1 | 9/2012 | Yang | |
| 2012/0245422 A1 | 9/2012 | Hasbun | |
| 2012/0320340 A1 | 12/2012 | Coleman | |
| 2013/0083185 A1 | 4/2013 | Coleman | |
| 2013/0102359 A1 | 4/2013 | Ho | |
| 2013/0128223 A1* | 5/2013 | Wood et al. | 351/206 |
| 2013/0222562 A1 | 8/2013 | Ono | |
| 2013/0300919 A1 | 11/2013 | Fletcher et al. | |
| 2014/0071547 A1 | 3/2014 | O'Neill et al. | |
| 2015/0002950 A1 | 1/2015 | O'Neill et al. | |
| 2015/0042877 A1 | 2/2015 | O'Neill et al. | |
| 2015/0070557 A1 | 3/2015 | Petty et al. | |
| 2015/0172522 A1 | 6/2015 | O'Neill et al. | |

FOREIGN PATENT DOCUMENTS

| | | |
|---|---|---|
| KR | 1020050093291 | 9/2005 |
| KR | 1020050100745 | 10/2005 |
| WO | WO2004/081653 A1 | 9/2004 |
| WO | WO2005/016135 A1 | 2/2005 |
| WO | WO2006/083081 A1 | 8/2006 |
| WO | WO2009149499 A1 | 12/2009 |
| WO | WO2011150444 A1 | 12/2011 |
| WO | WO2012058641 A2 | 5/2012 |
| WO | WO2013040352 A1 | 3/2013 |
| WO | WO2013071153 A1 | 5/2013 |
| WO | WO2013088144 A1 | 6/2013 |

OTHER PUBLICATIONS

Achanta et al.; SLIC superpixels compared to state-of-the-art superpixel methods; IEEE Transactions on Pattern Analysis & Machine Intelligence; 34(11); pp. 2274-2282; Nov. 2012.
Archer; rpartOrdinal: An R package for deriving a classification tree for predicting an ordinal response; J Stat Softw.; 34(7); 17 pgs.; Apr. 2010.
Arel et al.; Deep machine learning—A new frontier in artificial intelligence research; IEEE Computational Intelligence Magazine; 5(4); pp. 13-18; Nov. 2010.
Ballard; Generalizing the Hough transform to detect arbitrary shapes; Pattern Recognition; 13(2); pp. 13(2); pp. 111-122; 1981 (year of pub. sufficiently earlier than effective US filed and any foreign priority date).
Bay et al.; Speeded-up robust features (SURF); Computer Vision and Image Understanding; 110(3); pp. 346-359; Jun. 2008.
Bay et al.; SURF: Speeded up robust features; Computer Vision—ECCV 2006; Lecture Notes in Computer Science; vol. 3951; pp. 404-417; May 2006.
Blaivas et al.; Ultrasound image transmission via camera phones for overreading; The American Journal of Emergency Medicine; 23(4); pp. 433-438; Jul. 2005.
Brown et al.; Automatic panoramic image stitching using invariant features; Int J Comput Vis.; 74(1); pp. 59-73; Aug. 2007.
Canny; A computational approach to edge detection; IEEE Trans. on Pattern Analysis and Machine Intelligence; PAMI-8(6); pp. 679-698; Nov. 1986.
Cavanaugh; Pediatricians and the pneumatic otoscope: Are we playing it by ear?; Pediatrics; 84(2); pp. 362-364; Aug. 1989.
Christensen; Regression Models for Ordinal Data via Cumulative Link (Mixed) Models; ordinal-package section; pp. 1-4; version dated Nov. 8, 2011; retrieved from the internet on Oct. 15, 2014 (http://cran.r-project.org/web/packages/ordinal/index.html).
Daugman; Two-dimensional spectral analysis of cortical receptive field profiles; Vision Research; 20(10); pp. 847-856; 1980 (year of pub. sufficiently earlier than effective US filed and any foreign priority date).
Daugman; Uncertainty relation for resolution in space, spatial frequency, and orientation optimized by two-dimensional visual cortical filters; J. Opt. Soc. Am. A; 2(7); pp. 1160-1169; Jul. 1985.
Depeursinge et al.; Multiscale lung texture signature learning using the Riesz transform; Med Image Comput Comput Assist Interv.; 15(Pt 3); pp. 517-524; Oct. 2012.
Dziadzio et al.; A still image of a transient rash captured by a mobile phone; Clin rheumatol.; 26(6); pp. 979-980; Jun. 2007.
Ferzli et al.; A no-reference objective image sharpness metric based on the notion of just noticeable blur (JNB); IEEE Trans Image Precessing; 18(4); pp. 717-728; Apr. 2009.
Frean, J.; Microscopic images transmitted by mobile cameraphone; Trans. of the Royal Society of Tropical Medicine and Hygiene; 101(10); p. 1053; Jul. 2007.
Friedman; On Bias, Variance, 0/1-Loss, and the curse-of-dimensionality; Data Mining and Knowledge Discovery; Kluwer Academic Publishers; 1(1); pp. 55-77; Mar. 1997.
Gabor; Theory of communication. Part 1: The analysis of information; IEEE; The Journal of the Institution of Electrical Engineers—Part III: Radio and Communication Engineering; 93(26); pp. 429-441; Nov. 1946.

(56) References Cited

OTHER PUBLICATIONS

Golugula et al.; Supervised regularized canonical correlation analysis: integrating histologic and proteomic measurements for predicting biochemical recurrence following prostate surgery; BMC Bioinfomatics; 12:483; 13 pgs.; Dec. 2011.

Haralick et al.; Textural features for image classification; IEEE Trans. on Systems, Man and Cybernetics; 3(6); pp. 610-621; Nov. 1973.

Lieberthal et al.; The diagnosis and management of acute otitis media; Pediatrics; 131(3); pp. e964-e999; Mar. 2013.

Liu et al.; A survey of content-based image retrieval with high-level semantics; Pattern Recognition; 40(1); pp. 262-282; Jan. 2007.

Lowe; Distinctive image features from scale-invariant keypoints; Int J Comput Vis.; 60(2); pp. 91-110; Nov. 2004.

Makinen et al.; Add-on laser reading device for a camera phone; Optical Design and Engineering II; Proc. of SPIE; 5962; pp. 596228-1-596228-11; Oct. 2005.

Müller et al.; A review of content-based image retrieval systems in medical applications—clinical benefits and future directions; Int J Med Inform.; 73(1); pp. 1-23; Feb. 2004.

Peleg et al.; Multiple resolution texture analysis and classification; IEEE Trans. Pattern Anal. Mach. Intell.; 6(4); pp. 518-523; Jul. 1984.

Razdan et al.; The camera phone: a novel aid in urologic practice; Urology; 67 (4); pp. 665-669; Apr. 2006.

Rodriguez et al.; A microchip CD4 counting method for HIV monitoring in resource-poor settings; PLoS Medicine; 2(7); pp. 0663-0672; Jul. 2005.

Rublee et al.; ORB: An efficient alternative to SIFT or SURF; IEEE; 2011 IEEE Conf. on Computer Vision (ICCV); pp. 2564-2571; Nov. 2011.

Smeulders et al.; Content-based image retrieval at the end of the early years; IEEE Trans. Pattern Anal. Mach. Intell.; 22 (12); pp. 1349-1380; Dec. 2000.

Suzuki; Pixel-based machine learning in medical imaging; International Journal of biomedical Imaging; Hindawi Publishing Corp.; Article ID 792079; vol. 2012; 18 pgs.; 2012 (year of pub. sufficiently earlier than effective US filed and any foreign priority date).

Tibshirani; Regression shrinkage and selection via the lasso; Journal of the Royal Statistical Society; Series B (Methodolocial); 58(1); pp. 267-288; 1996 (year of pub. sufficiently earlier than effective US filed and any foreign priority date).

Unser et al.; Wavelet steerability and the higher-order Riesz transform; IEEE Trans Image Process; 19(3); pp. 636-652; Mar. 2010.

Wikipedia; Stereo Camera; 4 pgs.; retrieved from the internet on Oct. 21, 2014 (http://en.wikipedia.org/wiki/Stereo_camera).

Yuen et al.; Comparative study of Hough transform methods for circle finding ; Image and Vision Computing; 8(1); pp. 71-77; Feb. 1990.

\* cited by examiner

Tympanic Membrane Segmentation

```
function [feature_set, pixel_masks, img_sizes] = ExtractFeatures(obj,
images_or_filenames, varargin)
% Extract features image
% [feature_set, pixel_masks, img_sizes] = ExtractFeatures(obj,
% image_filenames, varargin)
%
% PARAMETERS
% training_pts_per_image: number of training pixels per
% image (default: 100)
% pixel_masks: one pixel mask per image (default: empty, computed here)
% b_exclude_black_border: don't extract features from dark regions, as
% determined by OtoImage.GetFOVMask (default: false)
%
% OUTPUTS
% feature_set: a Matlab table
% pixel_masks: cell array of pixel masks, one for each image, used
% in training
% img_sizes: sizes of input images %% Input parameters
p = inputParser;
p.addParameter('training_pts_per_image', 100);
p.addParameter('pixel_masks', {});
p.addParameter('b_exclude_black_border', false);
p.parse(varargin{:});

%% Run
SE_neighbors = getneighbors(obj.SE); % col1 = y, col2 = x if isempty(p.Results.pixel_masks)
    pixel_masks = cell(size(images_or_filenames));
else
    pixel_masks = p.Results.pixel_masks;
end % Loop over images
img_sizes = zeros(length(images_or_filenames), 2);
parfor kk = 1:length(images_or_filenames)
    try
        [feature_table_cell{kk}, pixel_masks{kk}, img_sizes(kk,:)] = ...
extract_dec_features(obj, ...
            images_or_filenames{kk}, pixel_masks{kk},
p.Results.training_pts_per_image, ...
            SE_neighbors, p.Results.b_exclude_black_border, obj.NumScales,
true);
    catch er
        fprintf('Error in iteration %d\n', kk);
        rethrow(er);
    end
end
feature_set = vertcat(feature_table_cell{:});

```
function [feature_table, pixel_mask, img_size] =
extract_dec_features(obj, image_or_filename, pixel_mask, num_pts,
SE_neighbors, b_exclude_black_border, num_scales, b_top_scale)
%% Function: extract features from decimated image % Chosen based on aesthetics by screwing around with
PMLClassifier.TestImageScaling
imresize_method_reduce = 'bicubic';
imresize_method_expand = 'bicubic';

switch obj.FeatureTransformEngine
    case 'matlab'
        resize_fcn = @imresize;
        color_transform_fcn = @(src)obj.ColorTransform.fcn(src);
        %disp 'Using MATLAB for color & resize'
    otherwise
        disp 'Warning'
end img = image_or_filename_to_image(image_or_filename);

if b_top_scale
   if isempty(pixel_mask)
      include_mask = get_include_mask(img, b_exclude_black_border);
      pixel_mask = get_pixel_mask(img, num_pts, include_mask);
   else
      include_mask = get_include_mask(img, b_exclude_black_border);
   end img_size = imsize(img);

[img, pixel_mask, pad_size] = zero_pad_img_and_mask(img, pixel_mask);
end if num_scales > 1
   % Get features from decimated image
   img_decimated = resize_fcn(img, 1/obj.ScaleReduceFactor,
imresize_method_reduce);
   feature_table = extract_dec_features(obj, img_decimated, pixel_mask,
num_pts, SE_neighbors*obj.ScaleReduceFactor, b_exclude_black_border,
num_scales - 1, false);
else
   feature_table = table;
end scale = round(size(pixel_mask, 1)/size(img, 1)); % Factor by which the
original image has been reduced if ~b_top_scale
   % This is a decimated image; resize to original image size
   img = resize_fcn(img, size(pixel_mask), imresize_method_expand);
end img_ctransform = color_transform_fcn(img);
```

FIG. 2C

```
% Get x and y coordinates for target pixels at this scale
pixel_mask_idx = find(pixel_mask);

% Create feature table
this_feature_vector = extract_features_one_image(img_ctransform,
pixel_mask_idx, SE_neighbors);
this_feature_table = array2table(this_feature_vector);
this_feature_table.Properties.VariableNames =
get_feature_names(SE_neighbors, scale);
feature_table = [this_feature_table, feature_table];

% If we're back at the top scale, undo padding and get average image
features if
% requested
if b_top_scale
  pixel_mask = remove_zero_padding(pixel_mask, pad_size);
  img_ctransform = remove_zero_padding(img_ctransform, pad_size);

if obj.b_AvgImageFeatures
    avg_image_features = extract_avg_image_features(img_ctransform,
include_mask);
    feature_table = [feature_table, repmat(avg_image_features,
size(feature_table, 1), 1)];
  end
end
function feature_vector = extract_features_one_image(img, pixel_mask_idx,
SE_neighbors)
%% Function: extract features from one image in a super fast way I
thought of in the shower % feature_vector is MxN with M observations of N features
% N is num_neighbors*num_channels where we loop first over neighbors,
then channels assert(isnumeric(pixel_mask_idx), 'Expected pixel_mask_idx to be an array
of numeric indices, got class: %s', class(pixel_mask_idx));

num_pixels = size(img, 1)*size(img, 2);
num_channels = size(img, 3);
num_observations = length(pixel_mask_idx);
num_features = size(SE_neighbors, 1)*num_channels;

% Create index map (for debugging)
index_map = reshape(1:numel(img), size(img));

% Turn SE_neighbors into 2D index offsets
index_offsets_2d = SE_neighbors(:,1) + size(img,1)*SE_neighbors(:,2);

% Make 3D: this is the full, multi-channel offset list
index_offsets_3d = flatten(bsxfun(@plus, repmat(index_offsets_2d, 1, 3),
[0 1 2]*num_pixels));

% Index into img of each observation and feature
```

FIG. 2D

```
feature_idx = bsxfun(@plus, repmat(index_offsets_3d(:)', 
num_observations, 1), pixel_mask_idx(:));

% Find valid observations (feature indices are within image bounds)
[feature_row, feature_col, feature_channel] = ind2sub(size(img), 
feature_idx(:));
idx_feature_valid = feature_row > 0 & feature_row <= size(img, 1) & ...
                    feature_col > 0 & feature_col <= size(img, 2) & ...
                    feature_channel > 0 & feature_channel <= size(img, 3);

% Assign valid features
feature_vector = zeros(num_observations, num_features);
feature_vector(idx_feature_valid) = img(feature_idx(idx_feature_valid));

% Copyright (c)2014 CellScope, Inc. All rights Reserved.
```

FIG. 2E

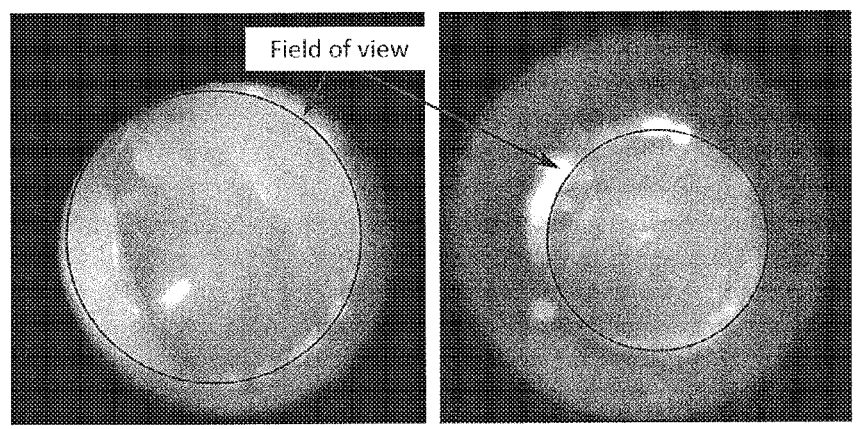

FIG. 3A   FIG. 3B

```
function [mask_out, mask_out_calculated] = Predict(obj, image, varargin)
% Run the trained classifier
% [mask_out, mask_out_calculated] = Predict(obj, image, varargin)
%
% PARAMETERS
% predict_fcn_args: arguments to pass directly to the appropriate predict
% function (e.g., predict for logistic regression or svmclassify for
% support vector machines)
% skip_pixels_x, skip_pixels_y: predict only on a subset of pixels and
% then create a final mask via interpolation. If skip_pixels_x is set
% to 1, for example, every other pixels will be predicted; if
% skip_pixels_x is set to 2, every third pixels will be
% predicted. 0 (default) indicates predicting on all pixels, with no
% interpolation
% include_mask: only predict a subset of pixels set to true in this
% mask (default: predict all pixels)
% b_force_logical_mask: if true, mask_out will be set
% to (mask_out >= 0.5) (default: true)
% b_resize_to_training_size: resize input image to size of training image
% b_sparse_output: instead of interpolating output if skip_pixels is
% nonzero, return a sparse matrix containing the explicit predictions
%
% OUTPUTS
% mask_out: output mask
% mask_out_calculated: sparse matrix containing 1 where the output
% was explicitly calculated and zero elsewhere (where there is no output,
% or output was interpolated)

%% Parse input arguments
p = inputParser;
p.addParameter('skip_pixels_x', 0);
p.addParameter('skip_pixels_y', 0);
p.addParameter('include_mask', true(size(image(:,:,1))));
p.addParameter('b_force_logical_mask', true);
p.addParameter('b_resize_to_training_size', true);
p.addParameter('b_sparse_output', false);
p.parse(varargin{:});

%% Setup
if isempty(obj.MLData)
   error('Cannot run classifier before it has been trained');
end include_mask = p.Results.include_mask;

%% Resize image and prepare skipped pixel indices
imsize_original = imsize(image);

if p.Results.b_resize_to_training_size
   image = resize_img_to_training_size(obj, image);
   include_mask = resize_img_to_training_size(obj, include_mask);
end
```

FIG. 2F

```
full_pixel_idx_x = 1:(p.Results.skip_pixels_x - 1):size(image, 2);
full_pixel_idx_y = 1:(p.Results.skip_pixels_x + 1):size(image, 1);

img_size = imsize(image);

%% Create a mask of pixels on which to predict
include_mask_subset = false(img_size);
include_mask_subset(full_pixel_idx_y, full_pixel_idx_x) = true;

calculate_mask = include_mask & include_mask_subset;

%% Extract features from image
feature_table = ExtractFeatures(obj, {image}, 'pixel_masks', ...
{calculate_mask});
feature_matrix = table2array(feature_table);

%% Run
response = GetPredictedValues(obj.MLData, feature_matrix);

assert(min(response) >= 0 && max(response) <= 1, ...
  'Expected response range to be between 0 and 1; limits are [%f %f]', ...
lims(response));

%% Convert response to image
% NaN response should only appear at the edges
response(isnan(response)) = false;

if p.Results.b_sparse_output
  mask_out = sparse(img_size(1), img_size(2));
  mask_out(calculate_mask) = response;
else
  % Interpolated the remainder of the values, including those that we
explicitly
  % calculated
  mask_out = zeros(img_size);
  [X, Y] = meshgrid(1:img_size(2), 1:img_size(1));
  scattered_interpolant = scatteredInterpolant(X(calculate_mask), ...
Y(calculate_mask), double(response), 'linear', 'nearest');
  mask_out(include_mask) = scattered_interpolant(X(include_mask), ...
Y(include_mask));
end mask_out_calculated = logical(sparse(img_size(1), img_size(2)));
mask_out_calculated(calculate_mask) = true;

if p.Results.b_force_logical_mask
  mask_out = mask_out >= 0.5;
end

%% Resize to original size
if p.Results.b_resize_to_training_size && ~p.Results.b_sparse_output
  mask_out = imresize(mask_out, imsize_original);
```

FIG. 2G

```
% Resizing can cause values to be out of range
mask_out(mask_out < 0) = 0;
mask_out(mask_out > 1) = 1;
end % Copyright (c) 2014 CellScope, Inc. (https://www.cellscope.com). All
rights Reserved.
```

FIG. 4A      FIG. 4B

Exam Feature Extraction

```
function [rank_struct, obj, features_query] = QueryImage(obj, oto_image)
% Submit a query image and get a ranking of database images based on k-
    nearest neighbors
% [rank_struct, obj, features_query] = QueryImage(obj, oto_image)
%
% Remember to store the returned obj to avoid re-calculating the
    KNNSearcher property
% for future queries.
%

%% Update KNNSearcher if necessary
if isempty(obj.KNNSearcher)
    obj = UpdateKNNSearcher(obj);
end %% Get features for the query image
features_query = GetFeaturesForImage(obj, oto_image);

% Remove unwanted features
features_query = features_query(:, obj.FeatureNamesInKNNSearcher);

assert(isequal(features_query.Properties.VariableNames, ...
    obj.FeatureNamesInKNNSearcher));

% Multiply by weights
features_query = table2array(features_query);
features_query_weighted = ApplyFeatureWeights(obj, features_query);

%% Perform k-nearest neighbors search
[idx, dist] = knnsearch(obj.KNNSearcher, features_query_weighted, 'K', ...
    size(obj.KNNSearcher.X, 1));

%% Transform results into output struct
ID_list = GetIDList(obj);
rank_struct = struct('rank', num2cell(1:length(idx)), ...
                    'ID', ID_list(idx), ...
                    'dist', num2cell(dist));

% Copyright (c) 2014 CellScope, Inc. (https://www.cellscope.com).
% All rights Reserved.
```

FIG. 13B

Automated Diagnosis

```
combined_features =
combined_feature_mean_by_contrast,combined_feature_variance_by_energy,...
                    combined_feature_mean_into_correlation];
feature_matrix = [feature_matrix, combined_features];

end

% Copyright (C)2014 CellScope Inc. - All Rights Reserved
```

FIG. 14D

```
%   Automated Diagnosis (Dx)[Training the classifiers]
%   Determine robust features and accurate classifiers to separate normal
%   tympanic membrane from abnormal conditions
%   This portion of Dx code performs the training of the model and tests
%   it using k fold cross validation as a first step and predicts on an
%   independent benchmark dataset as a second step.

function Dx_train_and_predict
tic
addingpaths;
% Train
[feature_matrix, outcome] = process_data_into_feature_vector;

% Perform dimensionality reduction
obj_pcaclass = PCAReduction(feature_matrix);
feature_matrix = Reduce(obj_pcaclass, feature_matrix);
PlotLatent(obj_pcaclass);

%   Classification: Training and testing (using cross-validation) with
%   various types of classifiers
rng('default');
[models] = ml_classifiers(feature_matrix, outcome);
clear feature_matrix;
clear outcome;

% Predict
[feature_matrix, outcome] = process_data_into_feature_vector;
feature_matrix = Reduce(obj_pcaclass, feature_matrix);

% Predictor for Test Data
test_on_benchmarkset(feature_matrix, outcome, models);

%
fprintf('\n');
toc end

% Copyright (C)2014 CellScope Inc. - All Rights Reserved
```

FIG. 14B

```
% Automated Diagnosis (Dx)  [Extract features]
% Primary function that does processing of raw data from a
% list, extracts features, performs machine learning processes
% and generates a reduced feature vector function [feature_matrix, outcome] = process_data_into_feature_vector
% Fetch the data
[input_dir, input_mask_dir, output_dir] = organize_input_data;
feature_table = table;

% Selecting image list option
[~, filenames, ~, outcome, mask, image_list] = choose_image_list;

% Loop through images in the data set
for image_count = 1: length(filenames)
   [oto_image_trimmed] = image_preparation(input_dir,input_mask_dir,
filenames, image_count, mask, image_list);
   oto_trimmed_image = oto_image_trimmed.Image;

% Save cropped images im RGB mode
   image_save(oto_image_trimmed, oto_trimmed_image, output_dir, filenames,
image_count);

% Transforming color space
   [~, input_image] = convert_to_lab(oto_image_trimmed);
   %input_image_hsv = image_conversion_hsv(oto_image_trimmed);

% Color features
   %oto_image = pre_process_for_color_features(input_image);
   color_features = GetFeatureColor(OtoImage(input_image));

%Texture features
   texture_features = GetFeatureTexture(OtoImage(input_image));

%Histogram of color based features
   histbin_features = GetFeatureHistogram(OtoImage(input_image));

% Update table with all feature categories
   feature_table = [feature_table; color_features, texture_features,...
      histbin_features];
end % Organize the data for classification - create Feature Space
feature_matrix = table2array(feature_table);

% Combined features
combined_feature_mean_by_contrast =
(feature_matrix(:,1).^2)./(feature_matrix(:,3).^0.5);
combined_feature_variance_by_energy =
(feature_matrix(:,8).^2./(feature_matrix(:,5).^0.5);
combined_feature_mean_into_correlation =
feature_matrix(:,1).*feature_matrix(:,4);

% Integrating them into the feature matrix
```

FIG. 14C

Automated Prognosis

Automated Determination of Disease Stage

Continuous Monitoring for Intervention Modification

Tympanic Membrane Panorama

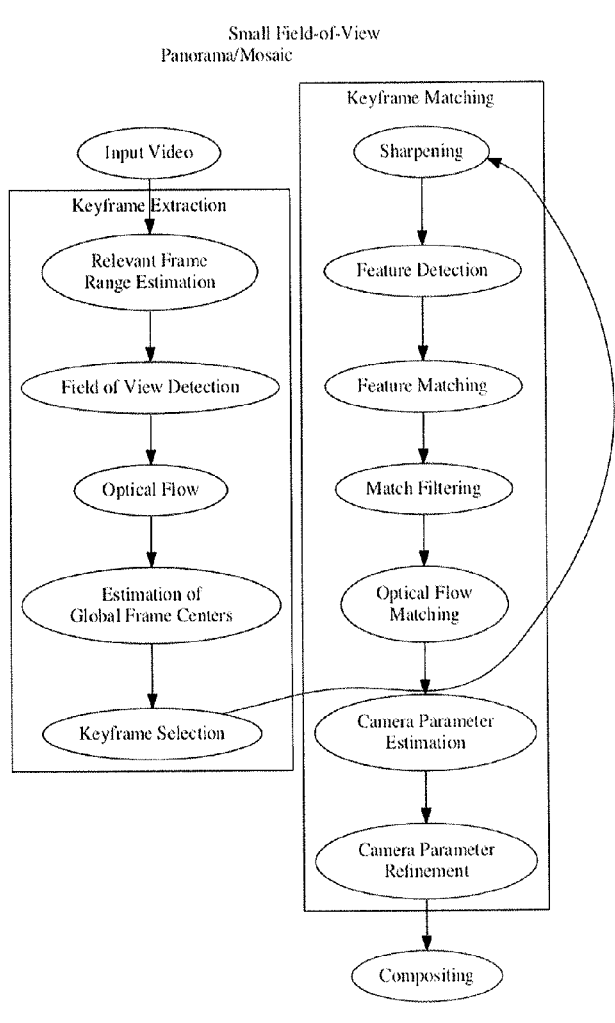
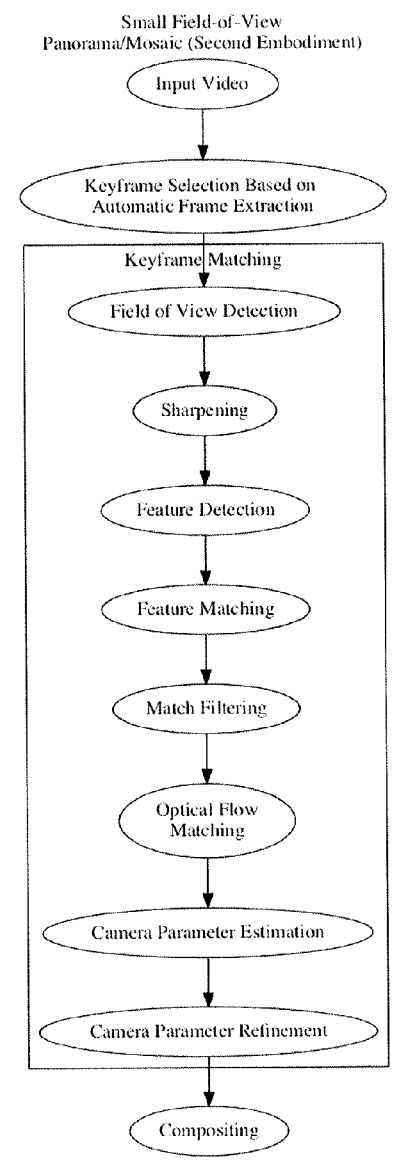
FIG. 22
FIG. 23

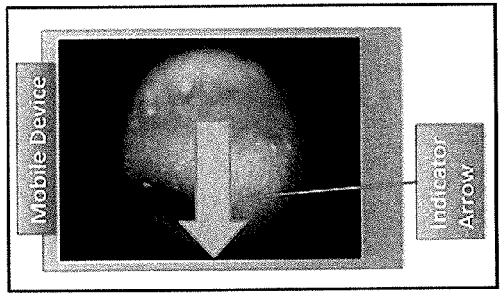
FIG. 26
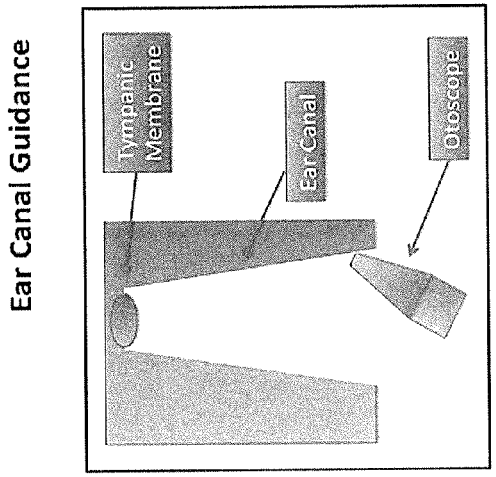
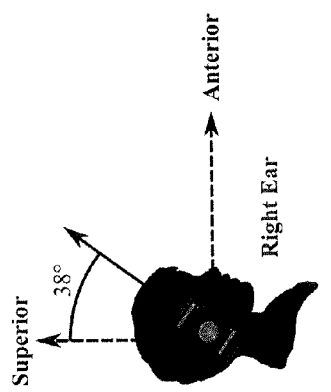
FIG. 24
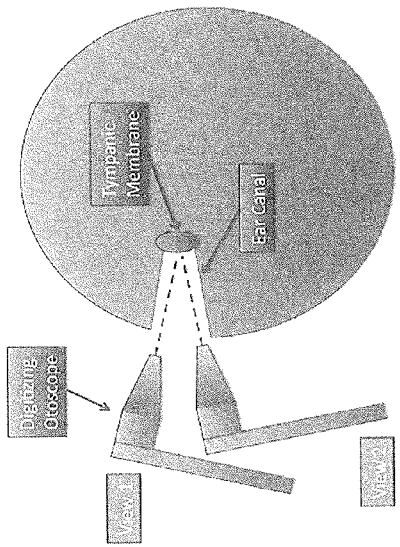
FIG. 25

```
function [pixel_idx, props] = RunOnFrame(obj, frame_id, varargin)
% Run depth finder on a single frame from a video
% [pixel_idx, props] = RunOnFrame(obj, frame_id, varargin)
%
% PARAMETERS
% b_debug: make debugging plot (default: false)
% h_fig: figure on which to make debugging plot; if h_fig=='gcf', use the
% current figure %% Parse input parameters
p = inputParser;
p.addParameter('b_debug', false);
p.addParameter('h_fig', []);
p.parse(varargin{:});

%% Go
[oto_image, img_gray_orig, fov_mask, avg_light] = get_cropped_frame(obj, frame_id);
img_gray_med_filt = median_filter_image(img_gray_orig);
img_gray_corrected = correct_illumination(img_gray_med_filt, fov_mask, avg_light);
img_quantile = quantile_image(img_gray_corrected, 'mask', fov_mask);

% Threshold
thresh = 0.1;
img_thresh = threshold_image(img_quantile, thresh);

% Morphologically close
img_thresh_closed = close_bw_image(img_thresh);

% Find connected regions
[props, props_idx_valid] = get_connected_regions(obj, img_thresh_closed, img_gray_med_filt);

% Output arguments
[pixel_idx, convex_hull_cell] = parse_output_args(props, props_idx_valid);

%% Debug plot
if p.Results.b_debug
    plot_debug(oto_image, fov_mask, img_gray_corrected, img_quantile, img_thresh_closed, props, convex_hull_cell, frame_id, p.Results.h_fig);
end function [props, props_idx_valid] = get_connected_regions(obj, img_thresh, img_gray)
%% Function: find the largest connected region
% Multiple regions may be returned props = struct2table(regionprops(img_thresh, img_gray, ...
    'Area', 'Eccentricity', 'Centroid', 'PixelIdxList', 'Centroid', ...
    'ConvexHull', 'Solidity', 'MeanIntensity'), ...
    'AsArray', true);
```

FIG. 27B

```
if isempty(obj.Classifier)
   props_idx_valid = props.Area > max(props.Area)*0.5 & ... % Area is at
least half as large as area of largest region
                     props.Area > numel(img_thresh)*0.01 & ... % Area is
at least 1% of total image area
                     props.Eccentricity < 0.995 & ... % Region is not
nearly a straight line
                     props.Solidity > 0.25 & ... % Region convex hull is
at least 25% filled
                     props.MeanIntensity < 0.3;
else
   features_table = props(:, obj.Classifier.FeatureNames);
   props_idx_valid = Predict(obj.Classifier, table2array(features_table));
end % Copyright (c)2014 CellScope, Inc. All rights Reserved.
```

FIG. 27C

Feature Explanation Interface

CBIR Result Drill-Down

Access Comparison Screen from CBIR Screen

Diagnosis Display Interface

Intervention Efficacy Display Interface

Expected Recovery Progression with Example Images

Expected Recovery Progression with Example Images: Comparison View

Display to Show Patient Superior Direction with Image

Method 1
Indication of superior direction with arrow

Method 2
Automatic rotation of image

Camera/Illumination Offset

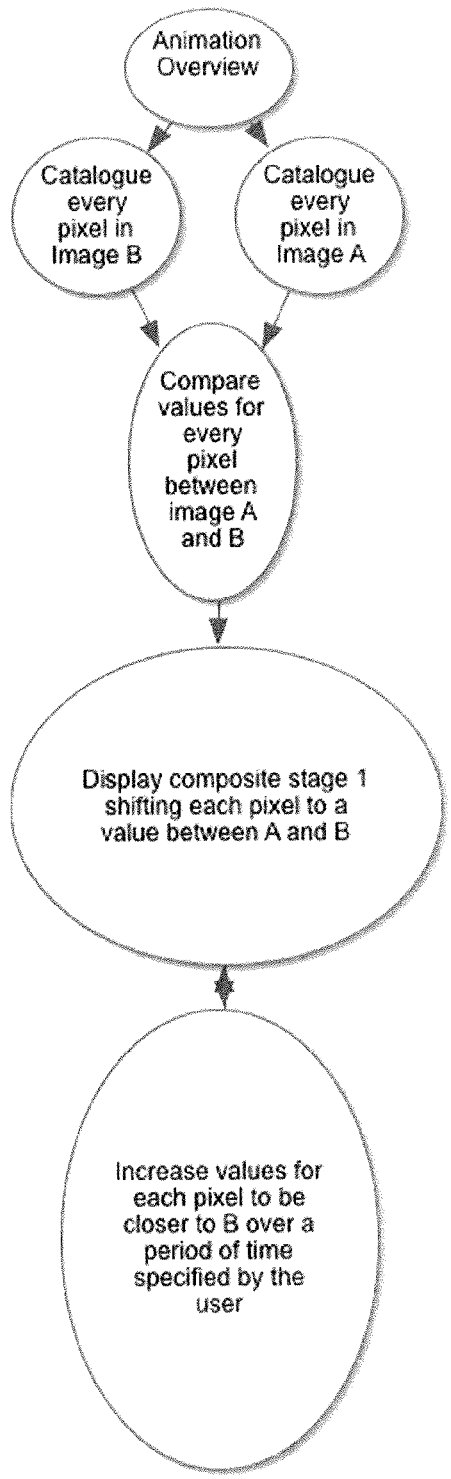
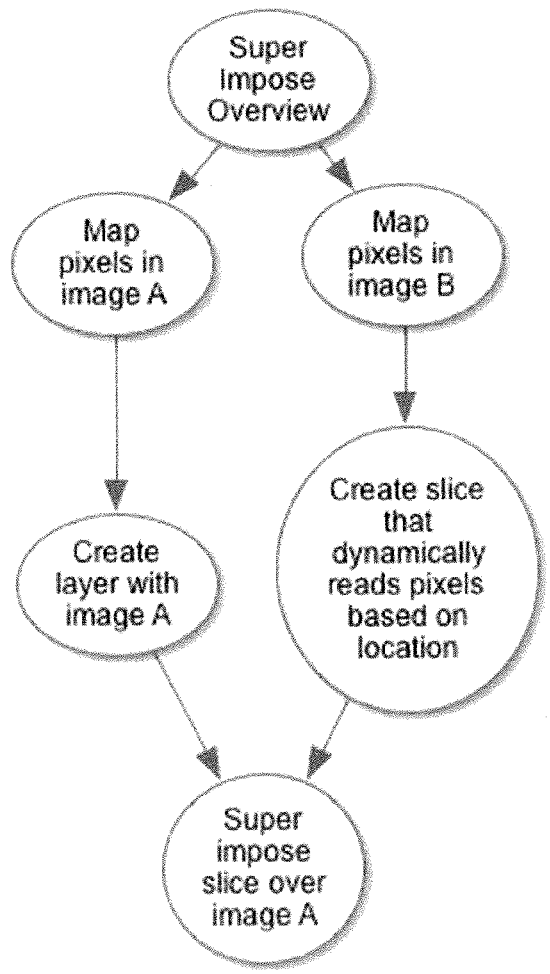
FIG. 48A  FIG. 48B

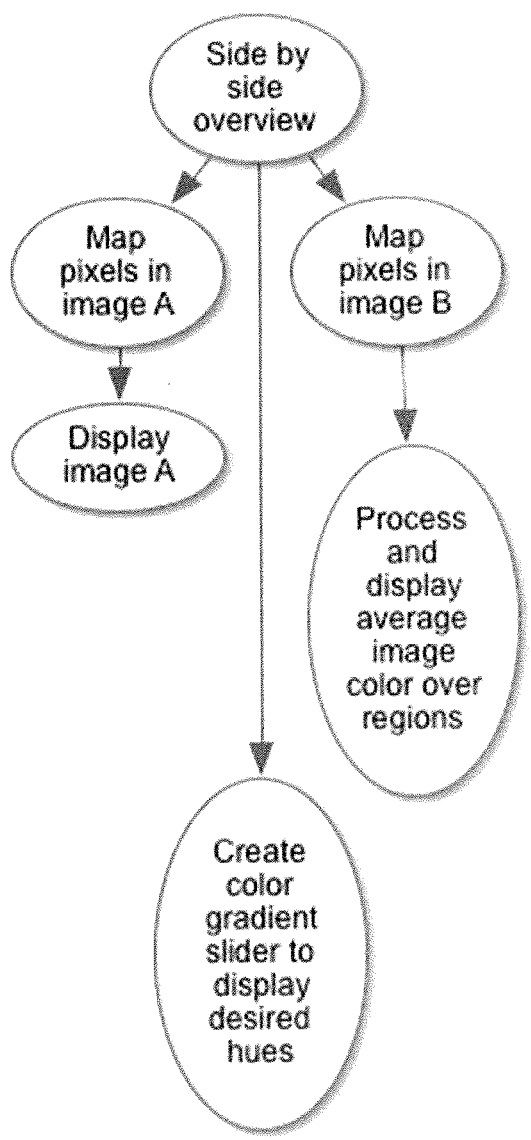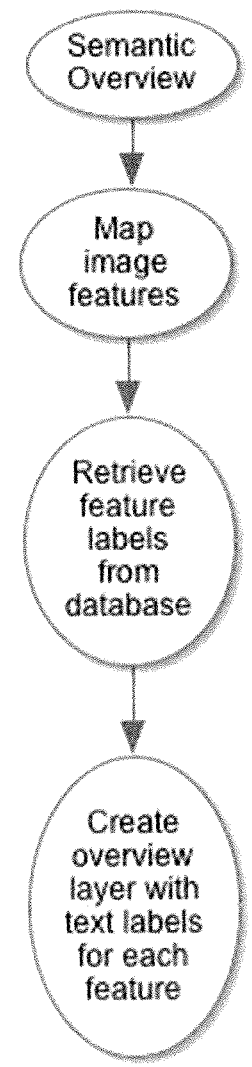
FIG. 48C                    FIG. 48D

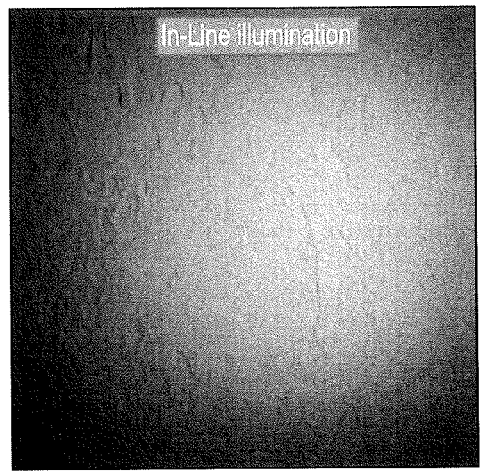
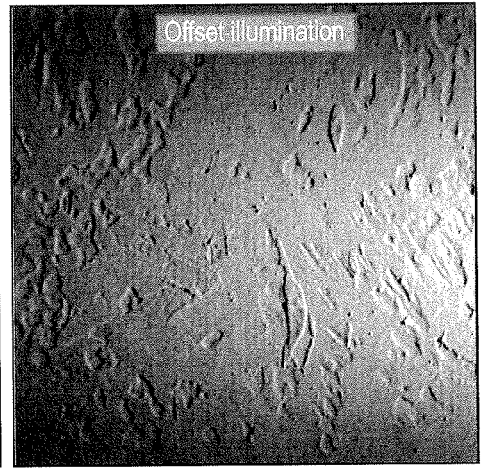
FIG. 49C            FIG. 49D
Otoscope Offset Illumination
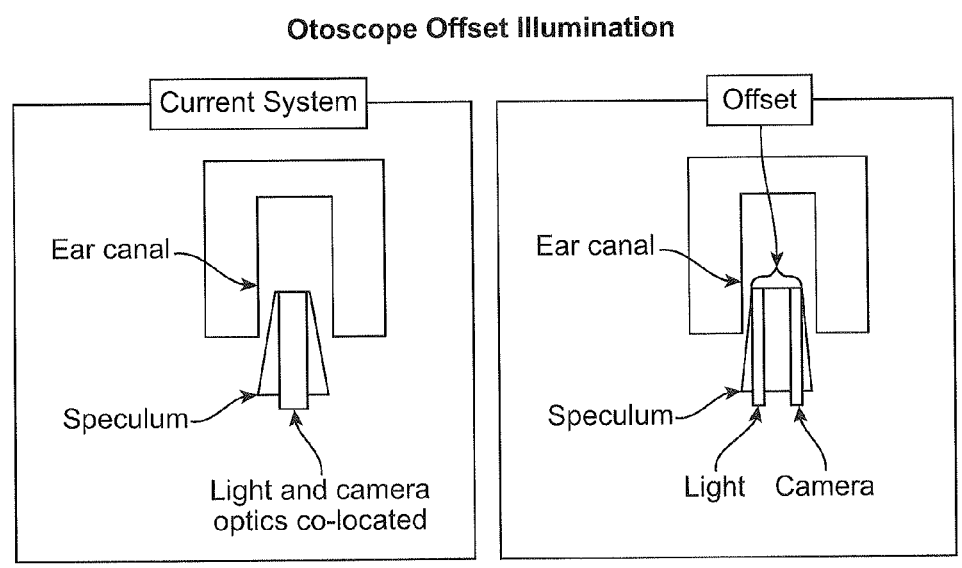
FIG. 50A            FIG. 50B

Otoscope Reflective Illumination

Stereoscopic 3D Otoscope

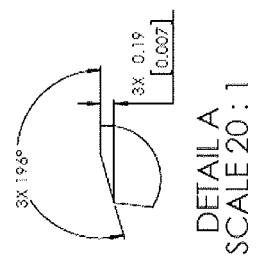
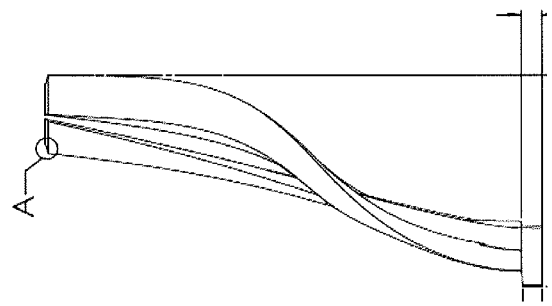
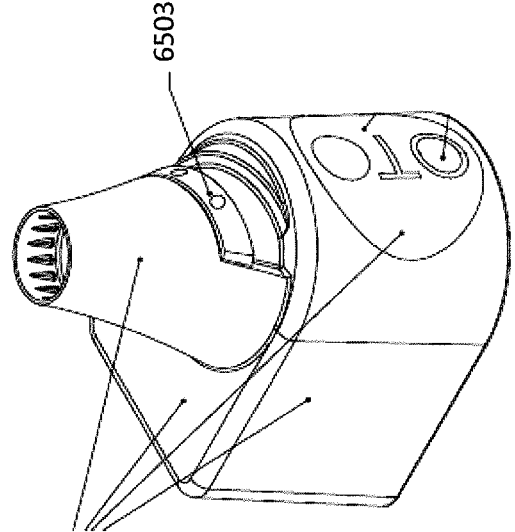
FIG. 65C
FIG. 65B
FIG. 65A

APPARATUSES AND METHODS FOR MOBILE IMAGING AND ANALYSIS

CROSS REFERENCE TO RELATED APPLICATIONS

This application claims the benefit under 35 U.S.C. 119 of U.S. Provisional Patent Application No. 61/874,041, filed Sep. 5, 2013, titled "SYSTEM AND METHODS FOR MOBILE IMAGING AND ANALYSIS", and U.S. Provisional Patent Application No. 61/988,281, filed May 4, 2014, titled "SYSTEM AND METHODS FOR MOBILE IMAGING AND ANALYSIS," and U.S. Provisional Patent Application No. 62/008,493, filed Jun. 5, 2014, titled "SYSTEMS AND METHODS FOR DIAGNOSTIC IMAGING." Each of these applications is herein incorporated by reference in its entirety.

International Application No. PCT/US2014/054382, filed concurrently herewith on Sep. 5, 2014 is also herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD

The methods and apparatuses described herein relate generally to the detection and analysis of anatomical structures using a handheld imaging device. In particular, described herein are methods and devices for detection and analysis of a tympanic membrane using a handheld otoscope device.

BACKGROUND

Otoscopes have long been a staple device in the physician's office as a tool for visually examining the ear. A typical otoscope, such as those manufactured by Heine Inc. and Welch Allyn, Inc., among others, includes a handle that may house a battery, and an instrument head mounted to the top of the handle. A conical speculum portion at a distal end of the instrument head permits insertion thereof a predetermined distance into the ear canal of a patient. An image is seen by the user through means of a magnifying eyepiece located on the rear or proximal side of the instrument, with the ear being illuminated by means of an interior lamp or a lamp tethered to a bundle of optical fibers located in the instrument head to facilitate viewing.

Other otoscopic instrument versions have since been developed which include a video camera that is attached to the eyepiece portion of the instrument head. An optical lens system, such as a relay lens assembly or a rod lens assembly, transmits the image directly to the camera. More recent versions employ a miniature imager element, such as a CCD, which is distally or otherwise positioned within the instrument head.

Otoscopes are typically used to allow a visual inspection of a patient's ear, and in particular, the patient's tympanic membrane. For example, acute otitis media (AOM), which is one of the most common ailments in children, can be classified as an infectious inflammation in the middle ear that typically starts abruptly with significant pain, is of relatively short duration and can be clinically verified (e.g., diagnosed) at least in part, by inspection of the tympanic membrane. Symptoms may include earache, fever and reddening and/or bulging of the tympanic membrane within the ear canal. Other ailments may also be suggested by visual inspection of the ear canal, including otitis media with effusion (Otitis Media with Effusion or OME), which may also present as bulging of the tympanic membrane; for example, a reddening and thickening of the tympanic membrane with a loss of normal topology may suggest AOM, OME, or a common cold virus. To an inexperienced observed, it may be difficult to diagnoses a problem with the tympanic membrane problems because there may be substantial visual overlap between the problems.

Thus, although the standard for medical diagnosis, and therefore medical treatment, may involve the use of an experience physician observing the patient's tympanic membrane, in some cases it may be difficult or overly costly for a patient, or (in the case of children) guardians/caregivers for patients, to timely visit a physician to have their ear examined directly by a physician or health care provider.

Thus, it may be desirable to provide tools, including in particular tools that may be used or incorporated into/onto a mobile computing device, such as a smartphone, pad, laptop computer, or the like, to act as an otoscope. In particular, it may also be useful to provide one or more tools and/or methods for guiding a subject (e.g., parent, caregiver, patient, health care provider, etc.) to acquire one or more images (including video) of the inner ear region, including or particularly including the tympanic membrane. Thus, these systems and methods may make it possible for untrained persons to take and save high-quality images of the tympanic membrane. In any of the variations described herein, the subject may also be the patient (e.g., they may be taking an image or images of their own ear).

It may also be useful to provide one or more methods and apparatuses for guiding the interpretation of one or more images of a subject's body (e.g., inner ear and/or tympanic membrane). For example, it would be helpful to provide one or more images of a patient's inner ear/tympanic membrane and provide similar images (including time course images) from a database of such images, particularly where the database images are associated with related images and/or diagnosis/prognosis information. It would also be helpful to identify a particular region (e.g., tympanic membrane) from an image, as well as provide methods and apparatuses for clarifying the images and preparing them for comparison to a database of similar images (for which one or more clinical identifiers may be associated).

Thus, described herein are methods and apparatuses (including devices and systems) for guiding taking of one or more images of a tympanic membrane, as well as analyzing the resulting image(s) and determining a diagnosis. In general these methods and apparatuses may identify a region of an image corresponding to a tympanic membrane, as well as presenting the image (e.g., along with similar images from a database).

SUMMARY OF THE DISCLOSURE

In general, described herein are methods and apparatuses (device and methods) to help guide a subject in taking an image of a body region (e.g., tympanic membrane within an ear canal), as well as method and apparatuses for identifying the body region from one or more images, and methods of identifying similar images from a large database of images, and methods and apparatuses for assisting in diagnosis using the image(s).

For example, described herein are methods and devices for detecting a tympanic membrane. In general, a method of detecting a tympanic membrane from an image of a subject's ear canal may include: receiving the image of the subject's ear canal; extracting a set of feature values for subregions of the image; estimating, for each subregion, a probability that the subregion is part of a tympanic membrane based on an extracted sets of feature values for the subregion; and identifying a tympanic membrane region from the image using the estimated probabilities for the subregions.

Thus, a method of detecting a tympanic membrane from an image of a subject's ear canal may include: receiving the image of the subject's ear canal; selecting a subset of subregions from the image; extracting a set of feature values for each of the subregions in the subset of subregions; estimating, for each individual subregion within the subset of subregions, a probability that the individual subregion is part of a tympanic membrane based on the extracted sets of feature values for the individual subregion; and identifying a tympanic membrane region from the image using the estimated probabilities for the subregions within the subset of subregions.

A method of detecting a tympanic membrane from an image of a subject's ear canal may include: receiving the image of the subject's ear canal; determining a field of view from the image; selecting a subset of subregions from the field of view of the image; extracting, at a plurality of different scales for each of a particular subregion within the subset of subregions, a set of feature values comprising a plurality of color space values for: the particular subregion in the subset of subregions, and for a plurality of subregions immediately adjacent to the particular subregion; estimating, for each individual subregion within the subset of subregions, a probability that the individual subregion is part of a tympanic membrane based on the extracted sets of feature values for the individual subregion; estimating, for subregions not within the subset of subregions, a probability that a subregion not in the subset of subregions is part of a tympanic membrane by interpolating from the probabilities that adjacent subregions within the subset of subregions are part of the tympanic membrane; and generating a probability map containing each of the estimated probabilities.

In some variations, a method of detecting a tympanic membrane from an image of a subject's ear canal includes: receiving the image of the subject's ear canal; automatically selecting, using a mobile telecommunications device, a subset of subregions from the image; extracting, using the mobile telecommunications device, a set of feature values for each of the subregions in the subset of subregions; estimating, for each individual subregion within the subset of subregions, a probability that the individual subregion is part of a tympanic membrane based on the extracted sets of feature values for the individual subregion; and identifying, on a representation of the image, a tympanic membrane region from the image using the estimated probabilities for the subregions within the subset of subregions.

In any of the methods described herein, receiving the image may include comprises receiving a video frame (e.g., an image taken from a video).

In general, extracting may comprise extracting feature values for each of the subregions in the subset of subregions at a plurality of different scales. Different scales may mean different magnifications, or different filtering levels. For example, a raw image may be processed to provide a different scale by filtering (e.g., blurring, sharpening, etc.) and the resulting processed image may provide an additional scale of the image.

For example, extracting may comprise extracting, at the plurality of different scales for each particular subregion within the subset of subregions, the set of feature values comprising a plurality of color space values for: the particular subregion in the subset of subregions, and for a plurality of subregions immediately adjacent to the particular subregion.

Any of these methods described herein may also include estimating, for subregions not within the subset of subregions, a probability that subregions not in the subset of subregions is part of a tympanic membrane by interpolating from the probabilities that adjacent subregions within the subset of subregions are part of the tympanic membrane.

Estimating may comprise using a trained classification model to predict if a subregion within the subset of subregions is part of a tympanic membrane.

Any of these methods may also include generating a probability map containing each of the estimated probabilities that each subregion within the subset of subregions is part of a tympanic membrane. The probability map may be applied over/onto the image, or it may be separated.

A subregion of an image may refer to a single pixel or adjacent groups of pixels. Selecting a subset of subregions may comprise selecting a subset of pixels forming the image. Selecting a subset of subregions may comprise selecting a field of view from the image and selecting a subset of subregions from within the field of view. In general, the selection of a subset of subregions from the image may be performed automatically by a processor (such as a mobile telecommunications device, e.g., a smartphone). Automatic selection is not manual, though it may be manually triggered; the actual selection of subregions may be performed automatically from the image.

In any of the methods and apparatuses described, the method may include a preliminary step of selecting (from an image) the field of view. The field of view may be a portion of the image that includes the ear canal. The field of view may exclude portions that are constant between images (e.g., the inner surfaces of an otoscope forming the image which may be present at the edges of the image, etc.). In general, the field of view includes the otoscope view of the ear canal, but excludes non-meaningful (typically surrounding regions) that may include images of the otoscope assembly (e.g. speculum) itself.

Extracting a plurality of features for each of the subregions in the subset of subregions may include: extracting a plurality of features for each of the subregions at a first scale; resealing the image at a plurality of different scales by decimating the image; and extracting a plurality of features for each of the subregions at each of the plurality of different scales.

Extracting a plurality of features for each of the subregions in the subset of subregions at a plurality of different scales comprises: extracting a plurality of features for each of the subregions at a first scale; resealing the image at a plurality of different scales by filtering the image; and extracting a plurality of features for each of the subregions at a second scale.

Any appropriate features may be extracted. For example, features may include color features (color space, such as RGB, HSL/HSV, CMYK, and lab color space, e.g., CIELAB). For example, eExtracting a plurality of features for each of the subregions in the subset of subregions may comprise extracting color space information for each subregion in the subset of subregions. Color space information may refer to color information for the image from a particular color space, such as CIELAB. Thus, only a portion of the color space information (one or more intensity, hue, saturation, lightness, etc.) may be used. Features may include statistical mappings or transformations of the raw color information, such as averages, distributions, standard deviations, etc. For example, extracting a plurality of features for each of the subregions in the subset of subregions may comprise extracting a color lightness value, a first hue value and a second hue value for each subregion in the subset of subregions. Extracting a plurality of features for each of the subregions in the subset of subregions may comprise extracting a color hue value, a color saturation value and a color brightness value for each subregion in the subset of subregions.

In general, identifying the tympanic membrane region may include any appropriate identification, including visual (e.g., identifying a tympanic membrane region from the image on a representation of the image by circling/outlining, highlighting, coloring, etc.), audible, indicating that the image includes such a region, or setting one or more registers associated with an image to indicate that the image includes a tympanic membrane, or portion of a tympanic membrane (e.g., above a threshold minimum amount of tympanic membrane region). A separate image including just the extracted tympanic membrane may be generated.

Any of the methods described herein may generally be performed by an apparatus that is configured to be executed on a processor.

For example, an apparatus may also include an otoscope or otoscope adapter (lens portion) to connected to a mobile telecommunications device and a non-transitory computer-readable storage medium storing a set of instructions capable of being executed by a processor, that when executed by the processor causes the processor to: receive an image of the subject's ear canal; select a subset of subregions from the image; extract, at a plurality of different scales, a set of feature values for each of the subregions in the subset of subregions; estimate, for each individual subregion within the subset of subregions, a probability that the individual subregion is part of a tympanic membrane based on the extracted sets of feature values for the individual subregion; and identify, on a representation of the image, a tympanic membrane region from the image using the estimated probabilities for the subregions within the subset of subregions.

Thus, described herein are non-transitory computer-readable storage medium storing a set of instructions capable of being executed by a processor, that when executed by the processor causes the processor to: receive an image of the subject's ear canal; select a subset of subregions from the image; extract, at a plurality of different scales, a set of feature values for each of the subregions in the subset of subregions; estimate, for each individual subregion within the subset of subregions, a probability that the individual subregion is part of a tympanic membrane based on the extracted sets of feature values for the individual subregion; and identify, on a representation of the image, a tympanic membrane region from the image using the estimated probabilities for the subregions within the subset of subregions.

Any of the methods and devices for identifying a tympanic membrane region (or portion of a tympanic membrane region) described herein may be configured or adapted for use as part of a method or device for displaying, matching, identifying, diagnosing, guiding a subject to acquire and image or, or otherwise examining a image or video including the determination of a tympanic membrane region.

Also described herein are methods and devices for guiding a subject to assist in taking an image a patient's tympanic membrane. In general, it may be difficult for a novice (or an untrained individual, such as a patient, parent or non-specialist) to image the tympanic membrane, and in particular to capture a sufficiently detailed image of a tympanic membrane for use in diagnosing or analysis using the tympanic membrane. Described herein are methods and device for aiding in imaging the tympanic membrane that may be used, in particular, for use with a home or clinical device that includes an otoscope (e.g., speculum, lens/lenses, and video/image capture capability). Images may be acquired until the method/apparatus indicates, e.g., visually or audibly, that an adequate image has been taken. The image(s) may then be stored, transmitted, and/or analyzed. For example, stored images may be transmitted to a medical provider for further analysis, or to a third-party analysis center.

For example, a method of guiding a subject using an otoscope coupled to a display device to image a tympanic membrane may include: displaying, on the display device, an image from the otoscope; detecting at least a portion of a tympanic membrane from an image of a subject's ear canal; indicating to the subject when an image of at least a portion of the tympanic membrane has been taken.

In general, a method of guidance or an apparatus for guiding a subject to take an image may examine images (digital images) of a patient's ear canal being taken by the user, e.g., operating an otoscope to determine when a minimum amount of tympanic membrane is showing (e.g., more than 20%, more than 25%, more than 30%, more than 35%, more than 40%, more than 45%, more than 50%, more than 55%, more than 60%, more than 65%, more than 70%, more than 75%, more than 80%, more than 85%, more than 90%, more than 95%, etc.) in the image. This may be done, as mentioned above. The method or apparatus may then indicate that an adequate image has been taken, and/or may automatically start sending, transmitting, and/or analyzing the image(s).

As mentioned above, detecting at least a portion of the tympanic membrane from the image may comprise: extracting a set of feature values for each of a plurality of subregions from the image; estimating, for each individual subregion within the plurality of subregions, a probability that the individual subregion is part of a tympanic membrane based on the extracted sets of feature values for the individual subregion.

Any of the methods and apparatuses described herein may be performed on/by a mobile telecommunications device, such as a smartphone (iPhone, Android, etc.), pad/tablet (iPad, etc.), laptop, and mobile computing device (e.g., Google Glass, iWatch, retina implant, etc.). For example, displaying one or more images on the display device may comprise displaying on a mobile telecommunications device. Thus, any of the steps of the methods described herein may be performed by the mobile telecommunications device (e.g., smartphone), including on the display and/or processor of the mobile telecommunications device. Some of the steps (or in some variations, all of the steps) may be performed remotely, e.g., by a processor to which the mobile telecommunications device is communicating. In general, as described herein a mobile telecommunications device includes any device that is portable, includes a processor and is configured to communicate with a network such as the internet and/or a telephony network, including, but not limited to smartphones (iPhone, Android, etc.), pads/tablets (iPad, etc.), laptops, and wearable computing devices (e.g., Google Glass, iWatch, retina implant, etc.)

In some variation a method or system may alternatively or additional guide a subject by providing one or more directions, including directions on a display screen showing the images, audible cues, textual cues or the like, so that the subject may move the otoscope device to adjust the view being taken. In addition, the method or system may indicate when the image is obstructed (e.g., by wax, foreign body, etc.) and/or when the image quality is low (poor lighting, focus/lensing issues, etc.).

For example, in some variations, a method of guiding a subject using an otoscope coupled to a display device to image a tympanic membrane may include: displaying, on the display device, an image from the otoscope; detecting one or more deeper regions in the image from the otoscope; indicating to the subject, a direction to orient the otoscope based on the detected one or more deeper regions.

A method of guiding a subject using an otoscope coupled to a display device to image a tympanic membrane may include: displaying, on the display device, an image from the otoscope; detecting one or more deeper regions in the image from the otoscope; indicating to the subject, a direction to orient the otoscope based on the detected one or more deeper regions; and indicating to the subject when an image of at least a portion of the tympanic membrane has been taken.

A method of guiding a subject using an otoscope coupled to a display device to image a tympanic membrane may include: taking an image of an ear canal using the otoscope; displaying, on the display device, the image; detecting one or more deeper regions in the image from the otoscope; indicating if the ear canal is occluded; indicating on the display device, a direction to orient the otoscope based on the detected one or more deeper regions; and indicating when an image of the tympanic membrane has been taken.

A method of guiding a subject using an otoscope coupled to a display device to image a patient's tympanic membrane, the method comprising: displaying, on the display device, an image of the subject's ear canal from the otoscope; detecting one or more deeper regions in the image: correcting for uneven illumination in the image, identifying one or more regions of brightness below a threshold in the image, extracting features for each identified region, and determining if an identified region is deeper in the ear canal based on the extracted features; indicating a direction to orient the otoscope based on the detected one or more deeper regions; determining if the image includes a tympanic membrane by: extracting a set of feature values from a plurality of subregions from the image, estimating, for each subregion, a probability that the subregion is part of a tympanic membrane based on the extracted sets of feature values; and indicating when an image of the tympanic membrane has been taken.

As mentioned, any of these methods may include detecting at least a portion of a tympanic membrane from an image of a subject's ear canal and indicating to the subject when an image of at least a portion of the tympanic membrane has been taken. The indicator may be visual, audible, or both.

For example, an indicator may be a beep, tone, song, etc., indicating that an adequate image has been taken. In some variations the indicator includes a flash, highlight, signal, text message, or the like, which may be displayed on the screen (e.g., of the display device, e.g., smartphone screen).

Any of these methods and apparatuses may also indicate an occlusion of an ear canal from the image, including automatically detecting when the ear canal is occluded. Additionally, any of these methods and apparatuses may also include instructing the subject to straighten the ear canal. Instructions may be visual (images, text, etc.) or audible, or both. In general, any of these apparatuses and methods may be configured to automatically detect when it is helpful or necessary for the subject to straighten the ear canal (e.g., by pulling on the subject's outer ear to align the canal). The method of device may include providing an indicator when the ear canal has been straightened sufficiently. Thus, instructing the subject to straighten the ear canal includes automatically instructing the subject to straighten the ear canal.

In some variations, detecting one or more deeper regions comprises: determining a field of view for the image, correcting for uneven illumination in the field of view, identifying from the field of view one or more regions of brightness below a threshold in the image, extracting features for each identified region, and determining if an identified region is deeper in the ear canal based on the extracted features. Alternatively or additionally, detecting one or more deeper regions may comprise: determining a field of view for the image, converting the field of view of the image to greyscale, filtering the field of view of the image to remove small objects, and dividing the image by an average illumination value.

Detecting one or more deeper regions may comprises: determining a relative distribution of pixel values from the image from the otoscope and identifying regions having the relative distribution of pixel values below a threshold value. Detecting one or more deeper regions comprises may include using a trained model to determine if the one or more regions are deeper regions in an ear canal. In some variations, detecting one or more deeper regions comprises extracting features from one or more regions of the image that are not as bright as other regions and using a trained model to determine if the one or more regions are deeper regions in an ear canal, wherein the extracted features include one or more of: region area, region eccentricity, region solidity, mean intensity of the region, and mean intensity of the region in an illumination-corrected image.

In general, the method or apparatus may indicate to the subject a direction to orient the otoscope based on the detected one or more deeper regions. This indication may be visual, e.g., displaying an arrow on the display device, text ("tilt right", etc.), audible (a tone or a verbal communication), or a combination of these.

The step of indicating to the subject a direction to orient the otoscope based on the detected one or more deeper regions may include: determining a centroid of the one or more deeper regions and guiding the subject towards the centroid.

As mentioned, any of these methods may include determining if the image includes a tympanic membrane. For example, by extracting a set of feature values from a plurality of subregions from the image, estimating, for each subregion, a probability that the subregion is part of a tympanic membrane based on the extracted sets of feature values.

Also described herein are apparatuses configured to guide a subject using an otoscope. For example, a system may include a non-transitory computer-readable storage medium storing a set of instructions capable of being executed by a processor, that when executed by the processor, causes the processor to: display an image from an otoscope; detect one or more deeper regions in the image from the otoscope; indicate to a subject a direction to orient the otoscope based on the detected one or more deeper regions; and indicate to the subject when an image of the tympanic membrane has been taken. Any of these systems may also include the otoscope (e.g., lens, speculum, etc.) and display device (e.g., smartphone or other mobile telecommunications device). The otoscope may be configured to couple to the display device, including coupling to a built-in camera on the display device and supplement any lenses on the built-in camera to convert it to a otoscope lens.

In general, also described herein are methods and devices for displaying a tympanic membrane. These methods may generally be performed on images collected and analyzed as described above, though they may be used/performed independently of these.

For example, a method of displaying an image of a tympanic membrane may include: displaying a first image of a subject's tympanic membrane; identifying a plurality of similar tympanic membrane images from a database of tympanic membrane images including images of the same tympanic membrane taken at different times, based on color and texture values of the first image; concurrently displaying the first image and the plurality of similar tympanic membrane images. A method of displaying an image of a tympanic membrane may include: extracting a plurality of image features from a first image of a subject's tympanic membrane, wherein the image features include color and texture data; combining the extracted features into a feature vector for the first image; identifying a plurality of similar tympanic membrane images from a database of tympanic membrane images by comparing the feature vector for the first image to feature vectors for images in the database of tympanic membrane images; displaying (e.g., concurrently) the first image and the plurality of similar tympanic membrane images and indicating the similarity of each of the similar tympanic membrane images to the first image.

A method of displaying an image of a tympanic membrane may include: selecting a region of interest from a first image including a tympanic membrane; extracting a plurality of image features from the region of interest of the first image, wherein the image features include color and texture data; combining the extracted features into a feature vector for the first image; identifying a plurality of similar tympanic membrane images from a database of tympanic membrane images by determining the distance between the feature vector for the first image and feature vectors for images in the database of tympanic membrane images, and selecting images from the database of tympanic membrane that are closest based on the determined distance; displaying the first image and the plurality of similar tympanic membrane images and indicating the similarity of each of the similar tympanic membrane images to the first image.

Extracting a plurality of image features from the first image may include extracting image features comprising color and texture data from the first image and wherein identifying the plurality of similar tympanic membrane images comprises using the extracted image features to identify the plurality of similar tympanic membrane images.

Any of these methods may also include allowing a user to select one of the plurality of similar tympanic membrane images and displaying time course images of the selected tympanic membrane image. In addition or alternatively, any of these methods or apparatuses may be configured to display a diagnosis associated with one or more of the plurality of similar tympanic membrane images. In general, the methods and apparatuses described herein may communicate with a dataset of images (e.g., tympanic membrane images) that includes associated information, which may include diagnosis information, associated symptom information (e.g., fever, headache, ear pain, etc.). For example, the subject/user may be allowed to select one of the plurality of similar tympanic membrane images and displaying time course images of the selected tympanic membrane image.

As mentioned, any of these devices and apparatuses may be configured to use a smartphone or the like. For example, displaying the first image and the plurality of similar tympanic membrane images may comprise displaying on a mobile telecommunications device.

Any of the methods for displaying the image of the tympanic membrane may include reducing the dimensionality of the feature vector to form a reduced feature vector and identifying the plurality of similar tympanic membrane images using the reduced feature vector.

In general, identifying the plurality of similar tympanic membrane images from the database of tympanic membrane images may comprise determining the distance between the feature vector for the first image and feature vectors for images in the database of tympanic membrane images, and selecting images from the database of tympanic membrane images that are near.

Any of these methods may also include transforming a color space of a first image of a subject's tympanic membrane into a uniform color space (e.g., CIELAB, etc.). For example, any of these methods may include transforming the first image into a perceptually uniform color space.

An apparatus for displaying an image of a tympanic membrane may include non-transitory computer-readable storage medium storing a set of instructions capable of being executed by a processor such as a smartphone, that when executed by the processor (e.g., smartphone), causes it to: display a first image of a subject's tympanic membrane from an otoscope; identify a plurality of similar tympanic membrane images from a database of tympanic membrane images including images of the same tympanic membrane taken at different times, based on color and texture values of the first image; concurrently display the first image and the plurality of similar tympanic membrane images.

Also described herein are methods and apparatuses to assist in diagnosis.

For example, described herein are methods of guiding diagnosis of an ear ailment using an image, the method comprising: extracting a plurality of image features from a first image of a subject's tympanic membrane, wherein the image features include color and texture data; combining the extracted features into a feature vector for the first image; applying the feature vector to a trained classification model to identify a probability of each of a plurality of different diseases; indicating the probability of each of a plurality different diseases.

A method of guiding diagnosis of an ear ailment using an image of a subject's tympanic membrane may include: selecting a region of interest comprising at least a portion of the subject's tympanic membrane from a first image including at least a portion of a tympanic membrane; extracting a plurality of image features from the region of interest of the first image, wherein the image features include data derived from the color and texture data; combining the extracted features into a feature vector for the first image; applying the feature vector to a trained classification model to identify a probability of each of a plurality of different diseases; indicating the probability of each of a plurality different diseases and displaying an image of an exemplary tympanic membrane for each of the plurality of different diseases.

Any of these methods may include reducing the dimensionality of the feature vector to form a reduced feature vector and applying the feature vector to the trained classification model comprises using the reduced feature vector.

As mentioned above, any of these methods and apparatuses may be configured to work on/with a mobile telecommunications device such as a smartphone. Thus, any of the steps may be performed on the mobile telecommunications device. For example, extracting may comprise extracting on a mobile telecommunications device.

Any of these methods may include selecting a region of interest including at least a portion of the tympanic membrane.

In some variations, the methods may include transforming the first image into a perceptually uniform color space (e.g., CIELAB) before extracting the image features. In general, extracting image features may include extracting color data comprising a mean of an image color channel within a region of interest.

There are many kinds of image features that may be extracted, however, color and texture image features (including "derived" color and texture features as described herein) have been found herein to be particularly useful. For example, extracting image features may include extracting color data comprising a median of an image color channel within a region of interest. Extracting image features may comprise extracting texture data comprising one or more of: energy, correlation and homogeneity of the tympanic membrane in one or more color channels. Extracting image features may comprise extracting texture data comprising one or more of: energy, correlation and homogeneity of the tympanic membrane in one or more of an L, A and B channel of the first image transformed to a CIELAB image. Extracting image features may comprise extracting a mean of all the standard deviations within one or more sub-regions of the first image from channel A and B of a CIELAB transformation of the first image. Extracting image features may comprise extracting a variance of all the standard deviations within one or more sub-regions of the tympanic membrane in channel A and B of a CIELAB transformation of the first image. Extracting image features may comprise extracting a normalized histogram of one or more values of channels L, A and B of a CIELAB transformation of the first image. Extracting image features may comprise extracting a ratio of a square of the mean value of at least a portion of the subject's tympanic membrane from the first image by a square root of a contrast texture value of at least the portion of the subject's tympanic membrane in the first image of channels A and B of a CIELAB transformation of the first image. Extracting image features may comprise extracting a ratio of square of the variance of a plurality of standard deviations within one or more sub-regions of at least a portion of the subject's tympanic membrane from the first image by a square root of an energy texture value in at least the portion of the subject's tympanic membrane in the first image of channels A and B of a CIELAB transformation of the first image. Extracting image features may comprise extracting a product of a mean value of at least a portion of the subject's tympanic membrane from the first image and a correlation texture value of at least the subject's tympanic membrane from the first image of channels A and B of a CIELAB transformation of the first image.

Textural information may generally be derived from a gray-level co-occurrence matrix (see, e.g., Haralick, R. M., Shanmugam, K., & Dinstein, I. (1973). Textural Features for Image Classification. Systems, Man and Cybernetics, IEEE Transactions on, 3(6), 610-621). For example, textural data may include energy, contrast, correlation and homogeneity of the tympanic membrane in one or more color channels.

Color and textural features that may be extracted from a tympanic membrane may include extraction of color features such as the average color hue value or a range of percentiles of color hue value of a tympanic membrane. Examples of specific color features that may be extracted include the average color value (hue) of tympanic membrane, and zero or more percentiles of color of tympanic membrane. Extracted texture features may be those features which characterize the degree of uniformity, coarseness or smoothness within a tympanic membrane image at a pixel level comparative scale. An example of such an extracted texture feature is average contrast value of a tympanic membrane, where contrast value is a measure of the intensity contrast between a pixel and its neighbor over the whole image. Another example is an average energy value of a tympanic membrane, wherein energy value is a measure of the degree of "uniformity" in an image. Another example is an average correlation value of a tympanic membrane, where correlation value is a measure of how correlated a pixel is to its neighbor over the whole image. Yet another example is average homogeneity value of a tympanic membrane, where homogeneity value is a measure of how evenly (or not evenly) intensity values are distributed over the entire image. Each of these examples may be mathematically defined as known in the art.

Texture features may also be extracted as one or more levels that are greater than the pixel level comparative scale (in which the smallest units of comparison are aggregated pixels, or sub-regions, typically adjacent to each other). For example, extracted texture features may include features which characterizes the degree of uniformity, coarseness or smoothness within a tympanic membrane image at a sub-region level comparative scale. An example of such a feature includes: average of standard deviations of sub-regions of a tympanic membrane, which indicates a measure of the degree of "coarseness" or "fineness" of an image. Each sub-region may have a different degree of "coarseness" or "fineness" and these localized textural differences can be captured and averaged using this feature. Another example includes a variance of standard deviations of sub-regions of a tympanic membrane, which indicates a measure of a variation of "coarseness" or "fineness" of an image. Each sub-region may have a different variation of "coarseness" or "fineness" and these localized textural differences can be captured in each sub-region and its variation across the image can be quantified using this feature.

Color and textural features that may be extracted include combined color and textural features. Extracted color and textural features (combined color and texture features) may characterizes the effect of image smoothness or coarseness for a certain color hue of the tympanic membrane at a pixel level comparative scale. An example of this type of feature includes a ratio of color value by contrast value of a tympanic membrane, which may provide increased separability of high hue-high contrast from low-hue low contrast tympanic membrane images. Another example is the ratio of color value and correlation value of a tympanic membrane, which may provide increased separability of high hue-low correlation from low-hue high correlation tympanic membrane images.

Combined color and texture features that may be extracted including extracted combined color and texture features that characterize the effect of image smoothness or coarseness for a certain color hue of the tympanic membrane at a sub-region level comparative scale. For example, a combined color and texture feature includes a ratio of variance of all the standard deviations by the energy value of sub-regions of a tympanic membrane, which may provide an increased separability of high hue-high coarse from low-hue low coarse tympanic membrane images.

In general, also described herein are methods and apparatuses that are configured to detect when a lens (e.g., otoscope lens) is connected to the device, and particularly to a mobile telecommunications device such as a smartphone. For example, a method of detecting if a lens device is attached to a mobile telecommunications device having a digital camera may include: taking an image using the digital camera of the mobile telecommunications device; comparing an average value for each of a plurality of clusters of pixels at a plurality of regions from the image to a first threshold value; indicating that the lens device is attached when the average values of each of the clusters of pixels in the plurality of clusters of pixels are lower than the first threshold value.

A method of detecting if a lens device is attached to a digital camera device may include: taking an image using the digital camera device; comparing an average value of a first plurality of pixels at a first corner region of the image to a first threshold value; comparing an average value of a second plurality of pixels at a second corner region of the image to the first threshold value; comparing an average value of a third plurality of pixels at a central region of the image to a second threshold value when the average values of the first and second plurality of pixels are both lower than the first threshold value; and indicating that the lens device is attached when the average values of the first and second plurality of pixels are both lower than the first threshold value and the average value of the third plurality of pixels is higher than the second threshold value.

A method of detecting if an otoscope lens device is attached to a mobile telecommunications device having a digital camera may include: taking an image using the digital camera of the mobile telecommunications device; comparing an average value for each of a plurality of clusters of pixels at a plurality of corner regions of the image to a first threshold value; comparing the average value of a central cluster of pixels at a central region of the image to a second threshold value; indicating that the lens device is attached when the average values of each of the clusters of pixels in the plurality of clusters of pixels are lower than the first threshold value and wherein the average value of the central cluster of pixels is higher than the second threshold value; and beginning an otoscope recording session when the lens device is indicated as attached.

The lens device may be an otoscope configured to be inserted into a subject's ear. The camera device may be a mobile telecommunications device (e.g., smartphone) having a built-in camera, as mentioned above.

Any group (plurality) of pixels may be used, including, e.g., a block of 3×3 or more pixels.

Comparing the average value may comprise comparing an average color RGB color values to the first threshold value. The first threshold value may be a value indicating a dark region. Once the lens is detected and indicated to be attached, the device may proceed to operate, for example, turning on a light source if the lens device is indicated as attached.

Any of these methods may also include comparing an average value of a fourth plurality of pixels at a third corner region of the image to the first threshold value, and indicating that the lens device is attached when the average values of the first, second and fourth plurality of pixels are all lower than the first threshold value and the average value of the third plurality of pixels is higher than the second threshold value.

Any of these methods may also include detecting one or more markings in the image identifying the lens device.

BRIEF DESCRIPTION OF THE DRAWINGS

FIGS. 2B-2E are an exemplary code listing for one example of a method of identifying tympanic membrane from an image.

FIGS. 2F-2H illustrate a method of predicting if an image includes a tympanic membrane or portion of a tympanic membrane.

FIGS. 3A and 3B illustrate identification of field of view from two images of an ear canal.

FIGS. 4A and 4B illustrate fields of view (outer and inner) for two images.

FIG. 13B is exemplary code for identifying similar images of TM from a database (library) of TM images.

FIG. 14B shows exemplary code for training a classifier that may be used to assist in diagnosis, as described herein.

FIGS. 14C and 14D show exemplary code for extracting features from an image of a TM to create the feature vector (and in this example, creating the reduced feature vector). The code beginning in FIG. 14C is continued in FIG. 14D.

FIG. 22 schematically illustrates one method of forming a panoramic view of a tympanic membrane from a plurality of images.

FIG. 23 schematically illustrates another method of forming a panoramic view of a tympanic membrane from a plurality of images.

FIG. 24 illustrates orientation of an imaging device (e.g., the video screen of a smartphone) with respect to patient position.

FIG. 25 schematically illustrates image acquisition for a 3D reconstruction of an ear canal.

FIG. 26 illustrates one example of guidance of subject using an otoscope to image a tympanic membrane.

FIGS. 27B and 27C are exemplary code for one variation of determining guidance for a user by estimating depth within an image. The code beginning in FIG. 27B is continued in FIG. 27C.

FIG. 48A is a schematic of a method of comparing tympanic membrane images, generating a composite image, such as the exemplary display shown in FIG. 39.

FIG. 48B is a schematic of a method for displaying tympanic membrane images by labeling features. Examples of such displays may be seen in FIGS. 40 and 41.

FIG. 48C is a schematic of a method of comparing tympanic membrane images including display of color gradient information. Examples of this type of display may be seen, for example, in FIGS. 43, 44 and 45.

FIG. 48D is a schematic of a method for displaying tympanic membrane images by labeling features. An example of this type of display is shown in FIGS. 46 and 47.

FIG. 49C is an example of in-line illumination.

FIG. 49D is an example of offset illumination.

FIG. 50A is an example of an otoscope having co-located (e.g., in-line) lights and camera optics.

FIG. 50B is an example of an otoscope system with offset illumination.

In FIG. 60, an axis on the left is the light entry axis, which is laterally displaced compared to the optical viewing axis on the right.

FIG. 65A illustrates the use of a 'bumps' or protrusions on an otoscope (e.g., component of otoscope) to decouple the lightpipe from the surface.

FIGS. 65B and 65C show the angled top (distal) surfaces of a lightpipe, which is designed to direct the rays from the lightpipe to be directed towards the surface being imaged.

DETAILED DESCRIPTION

Figure 1:
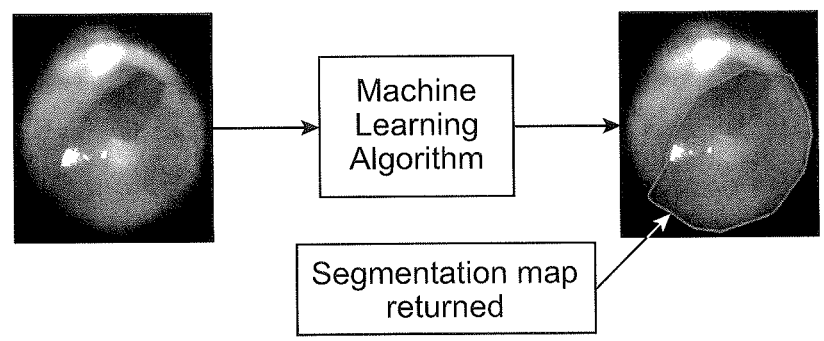
FIG. 1 illustrates one example of identification of a tympanic membrane from an image (tympanic membrane segmentation).

In general, described herein are apparatuses and methods for imaging and analyzing images. In particular, described herein are apparatuses and methods for imaging and examining images of an inner ear, including in particular the tympanic membrane (TM) region of the inner ear. These apparatus and methods include or be configured for use with an otoscope that may be operated by a physician (or other medical specialist) and in particular by an untrained, e.g., non-medical specialist, such as a parent or even the patient. In some aspects, the methods and apparatuses described herein assist the subject in taking images, and particularly images of the TM, including confirming that a TM (or part/region of a TM) has been identified. The methods and apparatuses described herein may also guide the subject in taking an image of the inner ear (and particularly the TM), as well as in interpreting the images acquired. The methods and apparatuses described herein may also assist a subject in identifying similar images from a database of images having known properties.

The methods and apparatuses described herein for a variety of imaging devices, including (but not limited to) those illustrated below. For example, many of the methods and apparatuses described herein may be variations of an otoscope, such as the mobile (e.g., portable) otoscope shown in FIG. 57. Other or similar otoscope systems may be used, for example, as described in U.S. application Ser. No. 13/855,501, filed Apr. 2, 2013, now Publication No. US-2013-0300919-A1 and herein incorporated by reference in its entirety. A portable otoscope such as the one shown in FIG. 57 may be configured to adapt a pre-existing mobile telecommunications device, such as a smartphone, into an otoscope capable of the various functions described herein. For example, any of the apparatuses described herein may include an otoscope attachment (component) having one or more imaging lenses configured to magnify images from the ear canal, and be configured to attach to a mobile telecommunications device (such as a smartphone). The otoscope attachment may be modular, and/or may include a lightguide (such as a lightpipe as described in more detail below) for transmitting light from the mobile telecommunications device (e.g., one or more "flash" LEDs on the phone) or an independent light source. In some variations the otoscope attachment couples to a case that attaches to the mobile telecommunications device. In general, the subject may provide/supply the mobile telecommunications device, and the mobile telecommunications device may be configured for operation specifically as an otoscope by software that is loaded/stored on a non-transitory computer-readable storage medium as a set of instructions capable of being executed by a processor of the mobile telecommunications device, that when executed by the processor causes the processor to operate as an otoscope having any of the features described herein. In one example of use, a modular otoscope component may be attached to a smartphone (or any other appropriate mobile telecommunications device). For example, a case may be attached to the smartphone and the modular otoscope component secured to the case so that the lens aligns with the camera lens built-in to the mobile telecommunications device. The flash of the mobile telecommunications device may be aligned with the light channel/lightpipe of the modular otoscope component. The modular otoscope may be locked into position on the mobile telecommunications device and/or the case for the mobile telecommunications device. A speculum cone (e.g., disposable cover for speculum) may be placed over the speculum form of the otoscope component (referred to as a speculum, for convenience). The mobile telecommunications device may then operate under control of the non-transitory computer-readable storage medium storing a set of instructions to control operation of the mobile telecommunications device and the otoscope component (or other imaging component in non-otoscope embodiments). For example, the display of the mobile telecommunications device may be used as a display screen for displaying controls (menus, buttons, sliders, etc.) and/or for displaying images (stills, movies, etc.) including a live display of the images received by the otoscope component. The set of instructions may include instructions allowing a subject to adjust settings, display parameters, and any other control features or operational features, including any of those described herein. For example, the apparatus may be configured to operate as an otoscope that can start/stop recording images, guide the user in taking one or more images of the ear canal, and in particular in taking one or more images of the tympanic membrane, and in automatically processing the images to identify the tympanic membrane (TM). The apparatus may also reference collected images (captured by the apparatus) to a library (database) of reference TM images, including identifying similar images and providing information specific to those images, as well as guiding diagnosis. The apparatus may also provide general training and interpretation of images or of ear ailments. The apparatus may also transmit one or more images and/or additional (patient-specific) information to a third party (e.g., database, electronic medical record, physician/health care provider, etc.). In addition or alternatively, the apparatus may allow various analysis and display options to assist in interpreting images, including in particular images of the TM.

TM Detection (Segmentation)

For example, described herein are methods and apparatuses that can automatically identify a tympanic membrane from an image, including in particular an image collected by the apparatus. These apparatuses and methods may also be referred to as tympanic membrane segmentation apparatuses and methods.

Generally, an otoscopic examination is usually intended to discern problems associated with the tympanic membrane (TM) in the ear. An otoscopic examination may be performed in real-time and/or may be recorded, e.g., via video or photographs using a mobile phone as described herein. Recordings may be available for subsequent or real-time processing. A given recording of the TM will generally include, in addition to the TM, other structures, such as the ear canal, hair, cerumen (earwax), etc. Described herein are apparatuses and method for automated identification and analysis of the TM by extraction of information (i.e., "features") from the images, including the TM. The apparatus may disregard ancillary structures when processing the image, if such processing is to take place exclusively on the TM.

For example, an otoscope system may include an otoscope component, including one or more lenses and a speculum for insertion into a patient's ear. The otoscope component may be coupled to a display device and one or more processors for receiving and analyzing images from the otoscope. In particular, the systems described herein may include an otoscope component that is coupled (directly or indirectly) with a mobile telecommunications device such as a smartphone; the smartphone acts as both the display device and as the processor for receiving, displaying and processing the image. The subject using/controlling the otoscope may be guided by the smartphone, including by observing the display screen of the smartphone, which may display the image of the ear (e.g., ear canal) when the otoscope is inserted into the patient's ear. The one or more processors may receive the image(s) from the otoscope and may analyze the images and/or record the images. In particular, the processor may automatically detect and segment the TM from digital video or image(s) taken during an ear exam. For convenience, the otoscope component may be referred to as simply an otoscope herein, though it should be understood that the otoscope may also refer to the system including the otoscope component as well as the display device and processor(s), e.g., connected to a smartphone configured to operate as the otoscope.

The application of TM segmentation may include two or more steps, including prediction of whether a given pixel or group of pixels is a member of the TM: feature extraction, followed by a machine learning method. Feature extraction consists of extracting a machine-readable set of image properties ("features"); these features are generally scalar parameters, the set of which (though not values of which) are invariant to image properties, such as size, color or source.

One appropriate method for TM segmentation consists of pixel-based machine learning. In this case, the features are the pixel values in an image surrounding the pixel-of-interest; features may also be determined simultaneously on multiple different scales or image size (e.g., at 10 pixels/mm, 5 pixels/mm, 2.5 pixels/mm, etc.). In the case of multi-scale features, features at multiple scales could be combined into a common feature vector. The target output is a continuous value, higher values of which approximately represent higher probability that the pixel-of-interest is a part of the TM. Pixel values may be determined from each of the image color coordinates in one or multiple color spaces, including RGB (red-green-blue), HSV (hue-saturation-value), CIELAB (International Commission on Illumination [CIE] 1976 L*, a*, b*), or others. The method is run for each pixel in the input image, and an output map, a segmentation likelihood map, of the same dimensions as the input image, may be created. Each pixel in the segmentation likelihood map may be assigned a value, e.g., from 0 to 1, where higher values indicate a higher likelihood of that pixel being within the TM. The segmentation likelihood map may also take on discrete values (e.g., only 0 and 1). The segmentation likelihood map may then thresholded at either a pre-determined or dynamically determined value between 0 and 1 to create a segmentation map. For each pixel in the segmentation likelihood map over the threshold, the corresponding pixel in the segmentation map may be set to 1 (True) and all other pixels in the segmentation map set to 0 (False). Once the TM segmentation map is created, any irregularities in the segmentation map (e.g., holes, errant pixels, etc.) may be eliminated with morphological operations (e.g., dilation and erosion).

The pixel-based machine learning method may be extended to use "superpixels," e.g., SLIC superpixels. Superpixels are connected groups of pixels with similar properties. An analogue to pixel-based machine learning, denoted "superpixel-based machine learning," would follow the same format as the above-described pixel-based machine learning, except that superpixels would be used in place of pixels. The target output would be, as before, a segmentation likelihood map, and all pixels within a superpixel-of-interest would be given a likelihood, from 0 to 1, say, of being within the TM. Features for the classifier would be derived from the superpixel-of-interest and locally surrounding superpixels. A richer array of features must be used in lieu of the simple pixel values used in pixel-based machine learning. One could instead use the mean or standard deviation of pixel values within each superpixel (again, in one or multiple color spaces), or more complex features based on texture, shape, size, or other properties of the superpixels including and surrounding the superpixel-of-interest.

The likelihood maps could also be combined with more traditional segmentation algorithms, including watershed, region growing, etc. Then, an augmented likelihood map could be created that combines information from the pixel or superpixel-based machine learning method and the traditional segmentation algorithm.

In some variations, the classification system may initially be trained as described below; thereafter, the trained classification system may be used to identify TM regions, although further training/updating may be performed. For example, extracted features may be fed to a machine learning method for classification. This machine learning method could consist of any feature-based supervised learning classification method, including logistic regression, lasso logistic regression, support vector machines, artificial neural networks, naïve Bayes, k-nearest neighbors, boosted ensemble classifiers, or others.

Training may be based on supervised machine learning and the model may therefore be trained before it can be used with new data. To generate training data, the user generates a training set of images, which may be frames from one or more videos, where each image contains an outlined contour of the TM to yield the TM segmentation mask. Some images may not contain a valid TM, in which case the TM segmentation will be present, but empty. The image subjects may include healthy TMs, pathological TMs (e.g., acute otitis media, otitis media with effusion, foreign bodies, etc.), or images that do not contain a TM. For images containing a TM, TM segmentation maps may be provided as a "gold standard" output for the images. For images which do not contain a TM, the segmentation maps will consist solely of 0 ("false") values. Images which do not contain a TM need not be otoscopic images if the classifier is to function on non-otoscopic images (e.g., images intentionally or accidentally taken outside the ear canal). A standard training procedure may be used for the machine learning method, using as input a subset of the total set of pixels and segmentations from the training set.

Once trained, the method may be able to automatically generate a TM segmentation for a given otoscopic image (or, possibly, a non-otoscopic image). An example of the expected output for an otoscopic image of a healthy TM is shown in FIG. 1. The output TM segmentation is shown, for illustration only, superimposed over the original image. The segmentation could be used in many different ways, including but not limited to: user training to indicate to a naïve user the location of the TM. In addition, focusing of additional machine learning methods to apply only to the TM portion of an image, to ignore the remaining portions of the image. Focusing of additional machine learning methods to apply only to the non-TM portion of an image may also be included, to ignore the TM portion of the image (e.g., for detection or classification of cerumen or rashes in the ear canal). Other benefits of segmentation includes quality control, to ensure that a given image or video contains a TM, and automated image extraction, to extract from a video of an otoscopic exam relevant frames that contain a TM.

In one example of a technique for identifying (segmenting) a TM from an image includes some or all of the steps described below. In an first step, setting out preconditions, the number of feature scales, N, is predetermined. This is the number of scales at which features will be extracted. For example, if N=2, features will be extracted from the original image, and from a single decimated version of the image. If N=3, features will additionally be extracted from a further decimated version of the image. A reasonable choice of N may be 4, though it could be any integer greater or equal to 1. Higher N will increase computational and algorithmic complexity, but may yield better machine learning performance. The preferred value of N will likely be chosen by trial and error.

A "scale reduction factor" is predetermined. This is the amount of blurring that is introduced when decimating the image to another scale. It represents the factor by which images are decimated, which in turn determines the optimal antialiasing filter bandwidth used in the decimation step. For example, if the scale reduction factor is 2, image height and width are both reduced by a factor of 2 at each scale, with an appropriate antialiasing filter applied. A reasonable scale reduction factor may be 2, though it could be any integer greater or equal to 1; the preferred value will likely be chosen by trial and error.

The input is generally an image (which may be a still frame from a video). In some cases, a Field of View is detected within the image, e.g., using a method as described below. Alternately, a pre-computed field of view may be used. Subsequent processing proceeds within the field of view.

Feature extraction may include converting the image to the CIELAB color space. Many alternate colors spaces would also work, though CIELAB has the advantage of being perceptually uniform (unlike RGB or HSV) and its hue channels are not cyclical (unlike the H channel of HSV). The mean of each channel within the FOV may be extracted as a feature; this would consist of a total of three scalar features, one for each channel. This step is optional and may allow the machine learning method to interpret pixel values as relative intensities instead of absolute intensities.

A subset of pixels may be chosen for processing. Choosing a subset of pixels for processing and interpolating across unprocessed pixels afterwards may significantly decrease the computational complexity of the method. It would also be possible to process all pixels at the expense of increased computational complexity. In the case of this embodiment, the pixel subset consists of every M pixels in the row and column directions of the image that are within the FOV, as determined by the FOV detection step. Increasing M trades off prediction accuracy for improvements in computational complexity.

Features may then be extracted for that pixel. Extracted features consist of the raw values of the pixel-of-interest and the pixels in a neighborhood surrounding the pixel, across all three CIELAB channels. For example, if an 8-neighborhood is used, then the features will consist of 9 values (the 8-neighborhood plus the pixel-of-interest), times 3 channels, for a total of 27 features (per scale).

If the apparatus has not yet performed N decimation steps, it may decimate the image and extract features at the new scale via the method of step "d." In the decimated image, the neighborhood will be the same, but since each pixel of the decimated image represents more than one pixel of the original image, the neighborhood will "reach further" with respect to the scale of the original image. It may be necessary to interpolate the pixel values in the decimated image because the pixel centers in the original and the decimated image may not line up. As an alternative to decimation, it would be possible to simply lowpass-filter the image and widen the neighborhood without actually subsampling the image; however, if more than two scales are desired, skipping the decimation step would increase the computational complexity without any obvious benefits (beyond slightly reduced code complexity).

The features may then be applied to an implementation of a pre-trained supervised machine learning classification model (e.g., a support vector machine or random forest model) included as part of the apparatus to predict whether the given pixel is part of the tympanic membrane or not. The output may be a "probability image," which consists of a probability from 0 to 1 that each processed pixel is part of the tympanic membrane.

The values of unprocessed pixels in the probability image may be determined by interpolating across processed pixels.

The output may be a probability image of the same size as the original image

Depending on the application, the apparatus may perform further processes, such as thresholding the probability image, performing morphological opening and/or closing, choosing the largest connected region, etc.

Figure 2A:
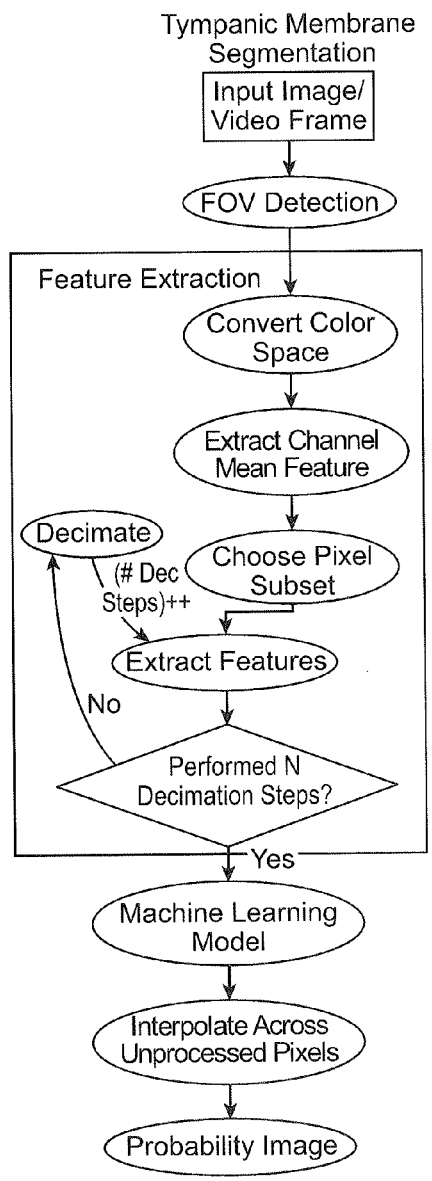
FIG. 2A is a diagram illustration one variation of a method for identifying tympanic membrane from an image.
Figure 2H:
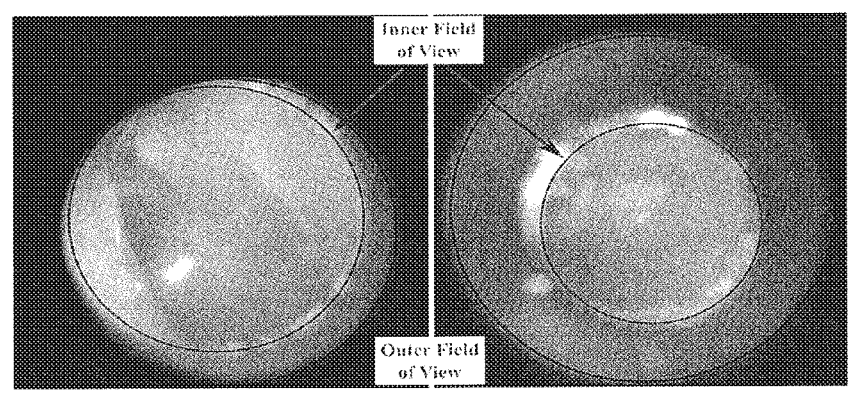

One example of an embodiment of this method of operating it is illustrated in the flow chart of FIG. 2A. FIGS. 2B-2E show an example of code for extracting features from an image and training a classifier to determine if there is a TM in the image, which may be part of a method of identifying a portion of an image likely to correspond to TM. FIGS. 2F-2H is an example of code for predicting if an image includes a TM or portion of a TM.

Field of View Detection

Images acquired with a standard camera (e.g., DSLR, "point and shoot," mobile phone camera, etc.) along with a lens attachment that fits over the standard camera lens may have part of the field of view obscured by the lens attachment; for example, this may occur when using an otoscope attachment to a smartphone. In this case, images acquired using the attachment may have everything but a central circular region of the image (hereafter referred to as the "field of view") obscured by the lens attachment, as shown in FIGS. 3A and 3B. In both images, an additional section of the field of view may be obscured by a speculum attachment on the otoscope device; the larger aperture of the adult speculum (left) obscures less of the field of view.

In FIGS. 3A and 3B, the Field of View is defined as the region of the image where the subject is visible. The left image (3A) shows an adult speculum, and the right (3B) is a pediatric speculum.

It may be desirable to be able to automatically locate the field of view within the image, particularly in the case where image processing or feature extraction algorithms are to be run only within the field of view. Locating the field of view may be particularly challenging due to variations in size of the field of view (e.g., due to variations in standard camera or module hardware or, in the case of an otoscope, due to different speculum sizes). Additional challenges may include varying location of the field of view (e.g., due variations in the standard camera or module hardware, misalignment of the attachment with the main camera, or of any additional attachments, such as the removable speculum), and varying shape of the field of view (e.g., in the case of an otoscope, if the speculum attachment is misaligned with the main otoscope module such that the field of view is no longer circular, or if wax or other debris obscures part of the field of view).

A general approach to locating the field of view in the recorded image may include the following steps, which may be performed by an apparatus as described herein. A "shape finding" method that can find one or more pre-determined shapes of varying sizes, locations and (possibly) orientations within an image may be used. The apparatus may then assess some quality metric of found matches depending on how well they match the shape prototype. The apparatus may use the found match of the highest quality as the "correct" field of view, as long as it exceeds some pre-determined quality threshold.

In the case of an otoscope (or other) module with variable size circular attachments that may obscure the field of view (e.g., different sized specula), a method of detecting the field of view may consist of a series of "circle finders" which return size and location of matched circles, the relative quality of the matches, and a machine learning model, based on the quality and properties of detected circles, to determine which circle actually comprises the field of view.

In the case of an otoscope and speculum, there may be two overlapping fields of view: the outer field of view of the otoscope module, which has enclosed in it both the subject and some area of the speculum (FIGS. 4A and 4B, circle), and the inner field of view of the speculum that shows only the subject, which is the field of view of interest (FIGS. 4A and 4B, circle). The inner field of view may be larger than the outer field of view, in which case, only the outer field of view will be visible.

One embodiment of a FOV detection for an otoscope module that may be included as part of an apparatus as described herein performs two parts: an outer circle finder and an inner circle finder. One example circle finder algorithm that may be used is the circular Hough transform (e.g., Yuen H K, Princen J, Illingworth J, Kittler J. Comparative study of Hough transform methods for circle finding. Image and Vision computing. 1990), which searches for a range of circle radii and centers within an image. Because the circles to be detected are known to lie within a certain range of sizes and locations, the search space of the circular Hough transform can be limited for computational performance. Additionally, the circular Hough transform returns a quality metric that is used to evaluate the circle quality; partial circles or circles with geometric irregularities will have lower values of the quality metric than will perfect circles.

This procedure could be logically extended to detect an arbitrary number of overlapping fields of view (instead of just the inner and outer circles) to return the smallest detected circle. Similarly, it could be adapted, using different variations on the Hough transform (Ballard D H. Generalizing the Hough transform to detect arbitrary shapes. Pattern Recognition. 1981) or other shape detectors, to detect a field of view of a different shape.

Figure 5:
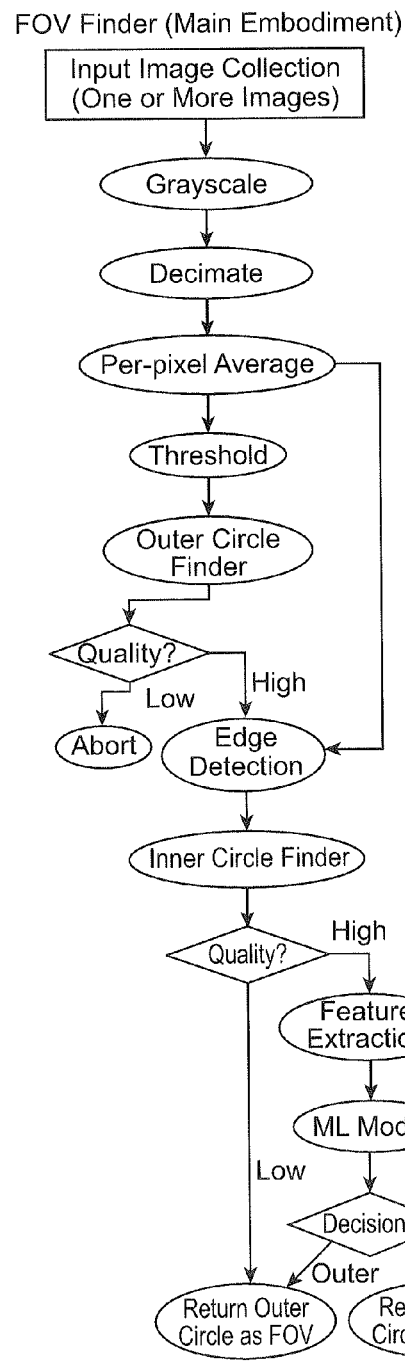
FIG. 5 illustrates one method of identifying a field of view from an image.

The system functions as shown in FIG. 5 and as described here. For example one or more images are collected; images may be converted to grayscale. Images may be decimated to a smaller resolution for computational speed; images may be averaged together on a per-pixel basis into a single "average intensity" image. The average intensity image may be thresholded at a predetermined threshold. The circular Hough transform may be used to search for an outer circle within a certain range of allowable radii and center location. The search range is determined in a preceding data analysis step. In general, multiple circles will be found of varying quality; only the circle with the highest quality is retained and the rest are discarded. The highest-quality detected circle may be examined. If the quality does not exceed a predetermined threshold, the process is aborted. Otherwise, edge detection is applied to the original average intensity image and a binary or real-valued edge mask is calculated. Edge detection proceeds only within the detected outer circle; edges outside the detected outer circle boundary are discarded. The circular Hough transform may be used to search for an inner circle using the same methodology described above. The highest-quality detected inner circle may be examined. If the quality does not exceed a predetermined threshold, return the outer circle as the field of view. Otherwise, extract features from the image and the detected outer and inner circles Features include: absolute inner metric: the quality of the detected inner circle, as returned by the circular Hough transform function; relative inner metric: the ratio of the highest returned inner circle metric to the second-highest returned inner circle metric; bushiness: the sum of the pixels in the edge mask; inner-outer center distance: the distance from the center of the inner circle to the center of the outer circle, in pixels; and inner-outer radius ratio: the ratio of the outer circle radius to the inner circle radius.

A pre-trained machine learning method may be applied, such as logistic regression, to predict whether (a) the detected inner circle represents the true field of view, or (b) the detected outer circle represents the true field of view. Thereafter, the apparatus may return either inner circle or outer circle as field of view, based on output of machine learning model.

Also described herein are automated frame extraction techniques and apparatuses adapted to perform them for medical videos. If a video is acquired from a medical exam, it may be desirable to extract individual frames for several reasons: to highlight desired anatomy or pathology; to be used as a "thumbnail" for rapid identification of the video; to reduce the information content by discarding unneeded frames (i.e., a form of "lossy compression" to summarize the video); and for use in a machine learning or image processing system that operates only on still images.

We describe here a method to automatically extract frames (e.g., for sharing or for further analysis) from a medical video based on the content of those frames. This method (which may be performed by an apparatus including a processor that receives the digital image) may first examine all or a subset of all frames contained within the video. If a subset of frames is used, that subset may be determined in several ways, including, but not limited to: every Nth frame for any positive integer N (e.g., every 10th frame for N=10); frames excluding those near the beginning and end of the video; frames on which or surrounding those on which a viewer of the video has manually paused playback (based on the premise that a viewer of a video will tend to pause playback on interesting or relevant frames).

In a first embodiment (Detection of Anatomical Entity), if the video is of an otoscopic exam, the apparatus may select frames to extract based on the presence or quality of a given anatomical entity of interest. For example, in an otoscopic video, the TM may be the anatomical entity of interest. In that case, for each selected frame, the TM will be detected and a segmentation map will be generated for each frame using the methodology described herein. Frames meeting certain criteria, based on the segmentation maps and image content, will be either flagged or extracted as images for further analysis. Criteria for the TM (or other anatomical entity) may include but are not limited to: a frame containing the largest TM area of all examined frames in a given video; a set of frames showing different portions of the TM; a set of frames spaced distantly in time throughout the video; all frames containing TM area (in square pixels) over some threshold area; and all frames containing any TM area.

Figures 6, 8:
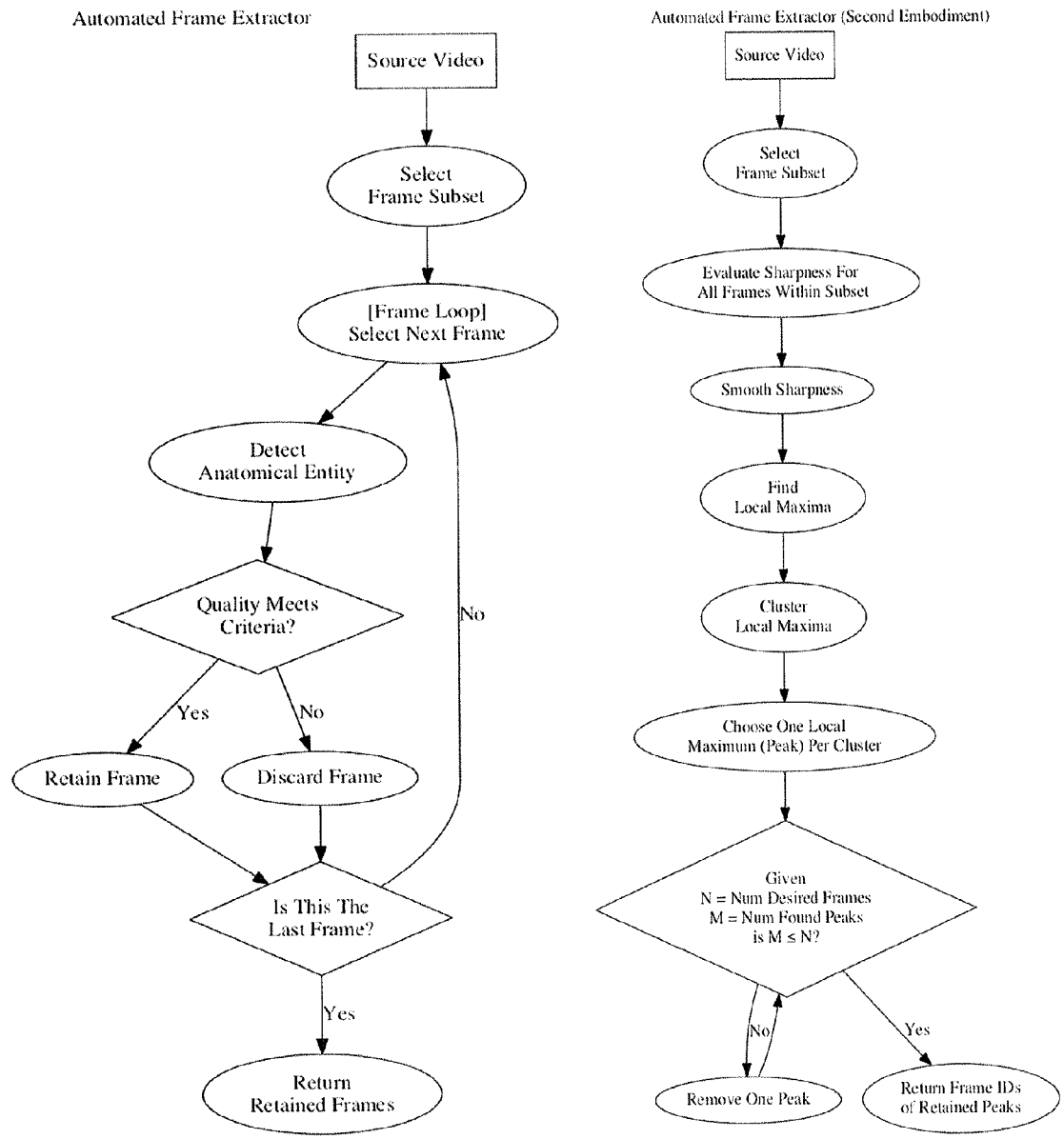
FIG. 6 illustrates a method of extracting frames from a video having multiple frames.
FIG. 8 illustrates another method of extracting frames from a video having multiple frames.

For any other medical video, a similar procedure could be followed, where, for each frame that is being examined, a "detector" for the anatomical entity of interest could be run, and a decision to extract the frame could be based on some analogous quality metric. Specifically, this embodiment proceeds as follows: select subset of frames for processing (e.g., every frame, every 2nd frame, etc); loop over every frame; detect anatomical entity (e.g., tympanic membrane); evaluate detection quality (if quality is high, retain frame, if quality is low, do not retain frame); and if this is the last frame, exit loop; if not, evaluate next frame. Finally, return retained frames. An example flow chart for this embodiment is shown in FIG. 6.

Another embodiment uses sharp frames. In this alternate, subject-independent method of frame extraction involves extracting only sharp frames from the movie. Over the course of a movie, the sharpness (also known as "contrast") of the frames may vary significantly due to changes in the subject, focus, lighting and motion blur. It is therefore desired to determine the optimal frames in the video where the subject is in clear focus and there is minimal blurring or other aberration. In particular, one may desire sharp frames distributed in time throughout the video so frames are extracted from each period where, e.g., the camera or subject was held still and the camera was given time to properly focus on the subject.

For a given frame that has been converted to grayscale, sharpness could be calculated in many different ways, including but not limited to: calculate the "contrast" property of the gray-level co-occurrence matrix (6) for the grayscale image; perform 2D FFT and get ratio of high-frequency information to low-frequency information; blur image, subtract blurred image from original image and sum the absolute value of the result (this is similar to examining the high frequencies of the image); other techniques may also be used (e.g., Ferzli R, Karam L J. A no-reference objective image sharpness metric based on the notion of just noticeable blur (JNB). Image Processing. 2009).

Figure 7:
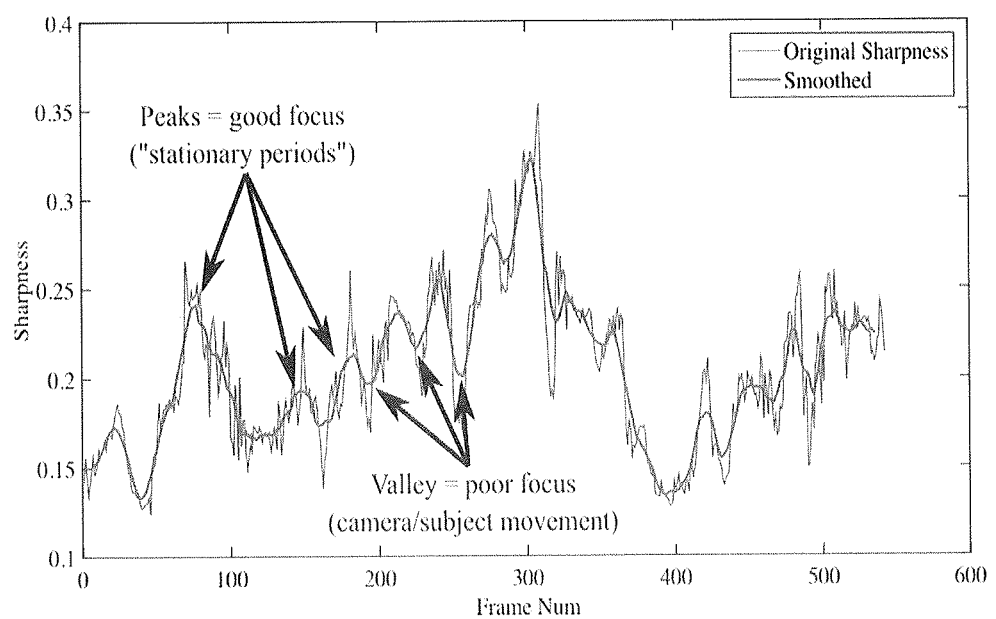
FIG. 7 shows an example graph of the sharpness of images in a video.

For a video where the subject or camera is moving, sharpness will periodically rise and fall. Sharpness will fall when the subject or camera moves and when the camera fails to focus on the subject, and it will rise when the subject or camera stops moving and focus is achieved. A reasonable goal for extracting frames would be to extract one representative frame from each period (up to, possibly, a maximum number of extracted frames) when the camera and subject are stationary and focus is achieved. These periods may be referred to as "stationary periods". See, for example, FIG. 7, showing a plot of sharpness for one video.

If it is desired to extract frames from some or all of the stationary periods, a naïve approach would be to calculate sharpness for every frame and simply return the N sharpest frames from the set (for predetermined N). This would not achieve the desired effect, however, as this would likely return only frames from a small subset of the stationary periods where the subject is the sharpest, e.g., where fine features (e.g., hairs) are present (e.g., all the returned frames may be near frame 300 in FIG. 7). Frames from other stationary periods where the subject has fewer fine features would not be returned. The returned frames would be biased towards only portions of the subject with fine features and frames containing regions of the subject that are not intrinsically sharp would not be returned. In the case of an otoscopic image, for example, the user may want to ensure that frames showing the tympanic membrane (generally a smooth, low-sharpness region) are returned, along with frames showing the ear canal (usually a region with high sharpness due to hairs and small folds).

The solution may be to calculate the sharpness for all (or a subset of) frames, find "peaks" in the sharpness plot, and only return one frame per peak.

This embodiment proceeds as follows below. The apparatus may select subset of frames for processing (e.g., every frame, every 2nd frame, etc.). Calculate sharpness for every frame within subset. Smooth the calculated sharpness by, e.g., setting the sharpness of each frame equal to the average sharpness of the five closest frames. Find local maxima within the graph of smoothed sharpness vs. frame number. Cluster local maxima based on the difference in their frame numbers; e.g., for a given threshold s, two local maxima belong to the same cluster if the difference in their frame numbers is less than or equal to s. Within each cluster, retain only the highest local maximum; call these retained frames the "peaks". Are there more peaks than the desired maximum number of returned frames? If so, the apparatus may find the two peaks which whose frame numbers are closest together and remove one; then repeat this step. Return frame IDs of retained peaks. A flow chart showing these steps appears in FIG. 8.

Image Features

Machine learning methods typically work on a fixed set of features as inputs to return a response, or output. A set of features consists of scalar values that summarize the input (e.g., an image) and can be easily processed with a computer. For example, in an otoscopic image of a TM, one might describe three values: redness (from 0 to 1), texture (0 to 1), and shape (0 to 1). These features together comprise a "feature vector" that would be extracted from the image before being fed as input into a machine learning method to predict some response (e.g., diagnosis, prognosis, etc.).

Digital images, e.g., an otoscopic image of the eardrum, cannot be trivially distilled into a feature vector. One could theoretically interpret each color channel of each pixel as a separate feature (generating, e.g., 30,000 features for a 100×100 pixel image with 3 color channels). However, this approach may generate a vast number of features for a typical image and these features would be overly-sensitive to image translation (left-right and up-down movement), scaling (changing size), rotation, and many other properties of images to which viable features are expected to remain invariant.

Instead, image features are typically extracted via a feature extraction method that is resistant to translation, scaling and other deformations and is designed specifically with the image subject in mind. For example, in otoscopic images, the images consist of visible-light images of the TM, ear canal, and related anatomy. One could therefore design feature-extraction methods that are specific to an otoscopic examination. In the case of otoscopic images, features may be extracted based on the following characteristics of the images.

Figure 9A:
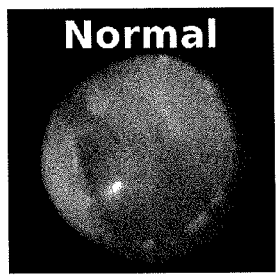
FIGS. 9A and 9B show figures (9A is Normal and 9B is Acute Otitis Media or AOM) allowing comparison of the color differences between normal (9A) and AOM (9B) images.
Figure 9B:
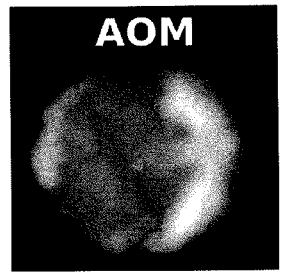

In normal physiology, the TM is typically grayish and partially translucent. However, in the case of many diseases affecting the TM, e.g., acute otitis media or otitis media with effusion, the TM may lose its translucency and, e.g., take on a reddish tint (compare FIG. 9A to FIG. 9B). Features related to color may therefore be useful for various machine learning tasks related to diagnosis, prognosis, etc.

Color features may be extracted in any color space, including but not limited to RGB (e.g., sRGB), HSV or CIELAB. Different color spaces present distinct advantages for image processing. Color features may include the mean, standard deviation, or other statistics of any color property associated with the TM or other outer ear structures, such as the ear canal, wax, hair, etc. For example, a redness features could be determined in the HSV color space and consist of the mean Hue for all pixels in the TM with Saturation and Value each greater than some threshold. Similarly, such a feature could be determined in the CIELAB color space, with distance of the average a* and b* values from red, for all pixels with L* above a threshold.

Normal TMs tend to have relatively smooth texture, with the exception of the areas near connecting structures (e.g., the malleus or umbo). Pathological TMs tend to have rougher textures (e.g., due to prominent vascularization) or pockets of fluid (effusion). One would therefore expect that texture features, particularly those involving the TM, could prove relevant in the diagnosis or other knowledge extraction for otoscopic images. These texture features could include, but are not limited to: Gray-level co-occurrence features (Haralick R M, Shanmugam K, Dinstein I. Textural Features for Image Classification. Systems, Man and Cybernetics, IEEE Transactions on. 1973 November; 3(6):610-21); Gabor wavelets (Gabor D. Theory of communication. Part 1: The analysis of information. Electrical Engineers—Part III: Radio and Communication Engineering, Journal of the Institution of. IET; 1946 Nov. 1; 93(26):429-41); The Riesz transform (Depeursinge A, Foncubierta-Rodriguez A, Van De Ville D, Müller H. Multiscale lung texture signature learning using the Riesz transform. Med Image Comput Comput Assist Interv. 2012; 15(Pt 3):517-24); Fractal analysis (Peleg S, Naor J, Hartley R, Avnir D. Multiple resolution texture analysis and classification. IEEE Trans Pattern Anal Mach Intell. 1984 April; 6(4):518-23); Properties of the 2D Fourier transform (e.g., spectral density of low frequencies vs. high frequencies); Properties of edges as determined by, e.g., a Sobel or Canny edge detector (16); Variance of image blocks' standard deviation; Mean of image blocks' standard deviation.

Figure 10:
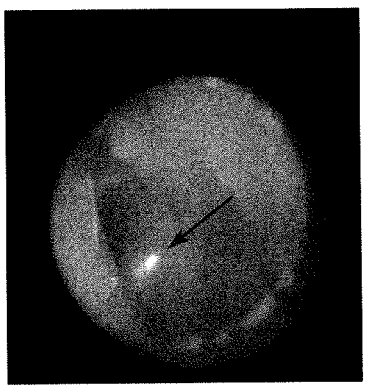
FIG. 10 illustrates a cone of light in an image of the ear canal/tympanic membrane.

For images of TMs, the "cone of light" may also be used as a characteristic feature from an image. A typical otoscopic examination of a healthy TM exhibits a phenomenon known as "cone of light", which is the reflection of the otoscope light source in the anterior inferior quadrant of the TM (FIG. 10, arrow). A pathologic TM may lack or have a distorted cone of light. Detection and characterization of the cone of light may therefore be useful in diagnosis or prognosis. The cone of light may be detected via various means. One method may proceed as follows: TM segmentation; thresholding of image by intensity (e.g., the L component in CIELAB) to yield a mask containing image pixels above a threshold intensity (since the cone of light will appear saturated or nearly so); construction of a mask which contains the intersection of the TM segmentation and the image intensity thresholding; morphological operations to close holes within and otherwise "clean" the mask; detection within the mask of connected regions of area above some threshold; measurement of certain properties of the connected regions, e.g., area, eccentricity, orientation, etc., that may help distinguish a cone of light from an unrelated specular highlight or other saturated region; thresholding based on those properties.

Other features may include but are not limited to: 2D shape (e.g., ellipticity, compactness) of the TM; shadows (which may indicate bulging or concavity of TM); reflectivity, possibly based on properties of the lightness of the TM or the number or properties of specular highlights, including the cone of light.

Deep learning (Arel I, Rose D C, Karnowski T P. Deep Machine Learning—A New Frontier in Artificial Intelligence Research [Research Frontier]. Computational Intelligence Magazine, IEEE. IEEE; 2010 Nov. 1; 5(4):13-8) could be used as an alternate, feature-independent machine learning method. In this case, image features would be learned "automatically" using convolutional neural networks or other techniques and may be combined with non-image features, such as semantic or clinical features (discussed below). Convolutional neural networks are traditionally applied to images as opposed to videos. There are several ways that they can be modified to apply to videos: extract a "representative" frame or frames from the video. In the case of an otoscopic exam, this may be the least blurry frame that contains the largest area of the tympanic membrane; convert the video into an appropriate summary image, e.g., a panorama; incorporate "time" (or frame number) as a third dimension and operate the convolutional neural network in 3D Beyond the quantitative features listed above, semantic features, e.g., annotations by a clinician or other trained human, may also be useful as machine learning features.

These features could be solicited from a human operator on a per-image or per-video basis either during the exam phase within a mobile app, or via a mobile or web interface after the exams have been uploaded to a centralized server. The human annotating the features need not have specialized training (e.g., medical school), since the semantic features will simply describe aspects of the image, not a diagnosis.

The following is an example list of semantic features that may be useful for otoscopic exams. Valid values may be multinomial (i.e., one option from a list of options or degrees between two endpoints) or continuous (e.g., a value from 0 to 1): Cone of light (absent to significant); Bulging (absent to significant); Vascularization (absent to significant); Cerumen (absent to significant); Foreign body (absent to significant); Ear canal irritation (absent to significant); TM Perforation (absent to significant); Tympanostomy tube (absent to present); Timpanostomy tube placement (N/A, correct, incorrect); Color (gray to red); Translucency (translucent to opaque); Growths (none to significant); or others.

Assessments of diagnosis, prognosis, etc., often benefit from general clinical information about the patient, in addition to image-based features. This clinical information may include, but is not limited to: Age, Race, Sex, Temperature, Height, Weight, Blood pressure, Current medications, Current diagnoses (i.e., pre-existing long or short-term conditions), Symptoms (e.g., pain, vomiting, urination, fever, trouble hearing, etc.), Medical history of any of the above, Geographical location of home, school, day care, work, etc., Lifestyle, Diet, and/or Exercise.

Generally, clinical information falls into one of two possible categories: numerical or categorical, which can be treated differently when converting them to features that are suitable for machine learning.

Numerical information (e.g., age, temperature, blood pressure) can take on scalar, real-numbered values (generally greater than 0). As such, they are suitable for directly being used as features in a machine learning system, which can operate with scalar values. Some information may be transformed, e.g., logarithmically, to reflect the non-normal distributions of the measurement and the fact that the effect of changing values may vary based on the original value. For example, the difference in physiologies between a newborn (0-month-old) and a 12-month-old child are likely to be vastly greater than the difference in physiologies between a 30-year-old and a 31-year-old adult, despite the fact that the age difference is one year in both cases. As such, one might use the logarithm of age as a feature instead of age itself.

Categorical information (e.g., sex, medications, diagnoses, symptoms) may be encoded in several ways. The most straightforward way is to treat each possible category as a separate feature. For example, if only three symptoms were possible, namely, pain, vomiting and fever, then each symptom would be encoded as a separate feature with two possible values, 0 (absent) or 1 (present). For a patient with pain and fever but no vomiting, the data could be represented in a table as follows:

TABLE 1

Example encoding of symptom features

| Pain | Vomiting | Fever |
|---|---|---|
| 1 | 0 | 1 |

This procedure can also be used for categorical information for which only one category is allowed to be in effect. For example, one could encode a subjective impression of the color of the TM during an otoscopic examination, where possible choices may be "gray," "yellow," "red" or "other." In that case, each of the possible choices would be encoded as a separate feature that can take on values of 0 (False) or 1 (True). One and only one feature would be set to True, and the others would be set to False. If there are N choices, and one and only one may be True, it is also possible to encode features for N−1 choices and let the Nth choice be implied to be True if all of the N−1 features are set to False.

Once calculated, clinical features may be used in concert with any other kind of feature, e.g., image features.

In addition to image features from an imaging examination, and standard clinical features, the apparatuses and/or methods may also include features determined from other tests or procedures. For example, for an otoscopic examination, features could be extracted from the results of: Insufflator measurements of TM mobility; Tympanometry measurements of the auditory canal's acoustic impedance; Tests for viruses or bacteria from tympanocentesis or directly from the middle ear in the case of tympanostomy tubes or TM perforation; Other sensors or tests which are not yet commonly used for clinical ear exam, including, but not limited to: Multispectral imaging, using one or more chromatic channels which may be narrowband or wideband and need not lie within the ~350-700 nm wavelength range of the human visual system, Mass spectrometry, and/or Volatile organics sensors.

Some exam measurements, such as those acquired by tympanometry, may have some features that can be extracted directly (e.g., compliance at 0 dekapascals, in cubic cm, for tympanometry measurements); other features that may need some form of extraction (e.g., hyperflaccid TM: true/false, stiff TM: true/false). Methods to extract these features will vary based on the individual measurements.

Once features are generated, regardless of their origin, they may be combined into a common feature vector. Features can be combined by concatenating them together into a single feature vector.

Figure 11:
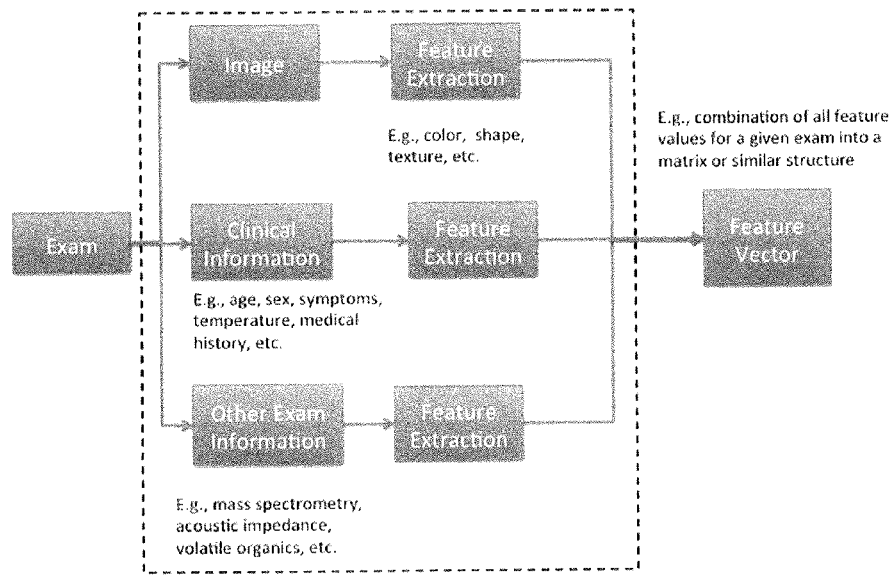
FIG. 11 is a schematic illustration of feature extraction from an image to form a feature vector.

The methods described herein can take the features created from all of these different data sources and assemble them into a combined feature vector (FIG. 11). This combined feature vector is suitable as input into a machine learning system for predicting, e.g., diagnosis or prognosis.

Further procedures may be employed for dimensionality reduction to reduce the so-called "curse of dimensionality" (e.g., Friedman J H. On Bias, Variance, 0/1-Loss, and the Curse-of-Dimensionality. Data Mining and Knowledge Discovery. Kluwer Academic Publishers; 1997; 1(1):55-77), in which, as the number of features increases, the machine learning procedure becomes less accurate due to overfitting. Many methods of dimensionality reduction exists, including principal component analysis, linear discriminant analysis, canonical correlation analysis (Golugula A, Lee G, Master S R, Feldman M D, Tomaszewski J E, Speicher D W, et al. Supervised regularized canonical correlation analysis: integrating histologic and proteomic measurements for predicting biochemical recurrence following prostate surgery. BMC bioinformatics. 2011 ed. 2011; 12:483), lasso regression (Tibshirani R. Regression Shrinkage and Selection via the Lasso. Journal of the Royal Statistical Society Series B (Methodological). 1996; 58(1):267-88), or others. Dimensionality reduction could be applied before or after features are combined.

At the time of a given exam, relevant information for predicting the diagnosis or prognosis may come not only from the current exam, but also from the results of past exams. For example, at the time of a given exam, a patient who has a history of Acute Otitis Media (AOM) is at higher risk of being diagnosed with AOM than a patient with no history of AOM, independent of information gleaned during the current exam. It is therefore useful to combine information from the current and past exams when making a prediction of diagnosis or prognosis.

If all patients received regular exams, for example, annually, it would be possible to simply generate one feature vector for the current exam, another for the exam from 1 year ago, another for the exam from 2 years ago, etc. Those feature vectors could then be combined via simple concatenation (possibly followed by dimensionality reduction) using the same procedure described herein to combine features within a single exam to form a combined feature vector.

However, in general, patients may not be expected to all have had regular past exams on the same schedule. For example, patient A may have had annual exams, patient B may have had exams every other year, and patient C may have only had exams during periods of illness, which occurred at irregular intervals. Therefore, there is a need for a consistent method of converting information from past exams into a feature vector in a way that does not depend on the frequency or interval between past exams.

Figure 12:
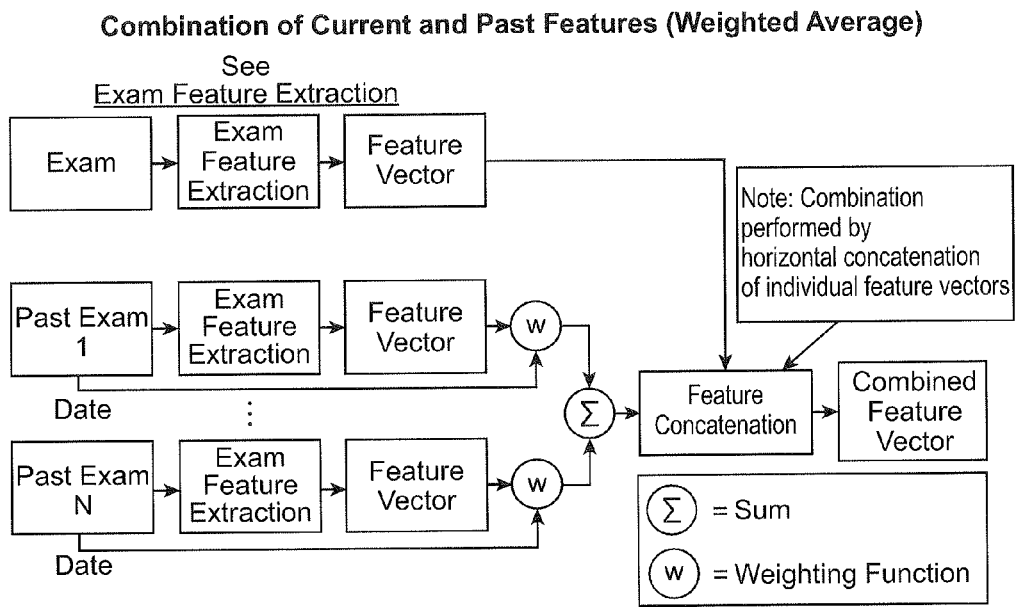
FIG. 12 is a schematic illustration of weighting of current and past features to form a feature vector.

One possible method for combining information from past exams is to combine features from past exams via a weighted average that takes into account the time from the current exam, with more recent exams weighted higher (FIG. 12). For example, a linear weighting function could be used which linearly runs from 0 at birth to 1 at the present time. For an example patient of age 10 who had exams at ages 3 months, 9 months, and 6 years, each feature would be averaged together across exams (excluding the present exam), with weights of 0.025, 0.075 and 0.6. Weighting functions other than linear could be used (e.g., logarithmic, power law, etc.) and weights could also be normalized to add up to 1. Features from the current exam would also be included separately in the feature vector, concatenated together with the weighted features from past exams.

Alternatively, one could include the current exam's features in the weighted feature vector from past exams, instead of including it separately.

Content-Based Image Retrieval

Content-based image retrieval (CBIR) is a method of retrieving images that are similar to a query image (Smeulders A W M, Worrng M, Santini S, Gupta A, Jain R. Content-based image retrieval at the end of the early years. IEEE Trans Pattern Anal Mach Intell. 2000; 22(12):1349-80; Müller H, Michoux N, Bandon D, Geissbuhler A. A review of content-based image retrieval systems in medical applications-clinical benefits and future directions. Int J Med Inform. 2004 February; 73(1):1-23; Liu Y, Zhang D, Lu G, Ma W Y. A survey of content-based image retrieval with high-level semantics. Pattern Recognition. 2007).

Returned results are usually ranked to allow more similar results to be displayed above less similar results. The operation of CBIR typically determines some measure of "similarity." Measuring similarity is challenging, as the concept of similarity is highly context dependent and subjective.

Instead of seeking a complete machine understanding of an image, images can be related to each other using basic extracted features, such as those discussed herein. These features will be weighted either (a) a priori, via a high level expectation of which features are likely to be most useful in the CBIR application or (b) via training to a example data set of images with manually-determined relative similarity, which would represent a gold standard for the purposes of the CBIR application of interest or (c) based on the relative importance of each feature in determining diagnosis, e.g., via the weights of a logistic regression model.

Figure 13A:
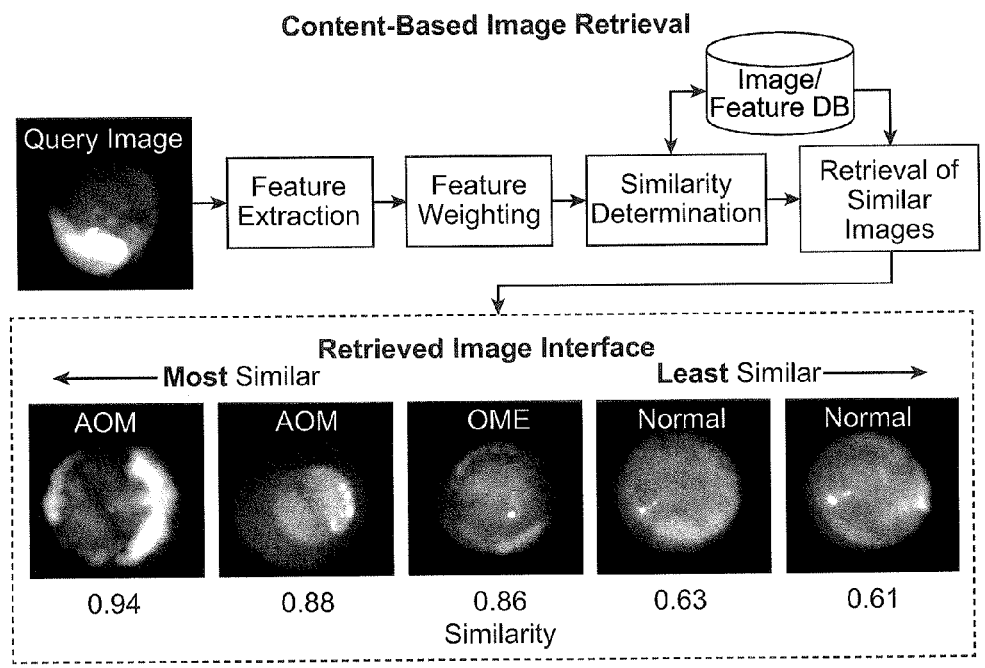
FIG. 13A shows one example of the display of similar tympanic membrane images selected from a library of annotated tympanic membrane images.

After the CBIR machine learning system is trained, regardless of the training method, the system is ready to perform CBIR. The CBIR method proceeds as follows (FIG. 13A): Query: A "query image" is generated, e.g. from a current or past exam, or any other source (e.g., from an image selected from the image database); Feature Extraction: Features are extracted from the query image; Feature Weighting: Features are weighted according to a pre-determined weighting scheme; Similarity Determination: The weighted features from the query image are compared with features vectors associated with images in the image/feature database, which contains a large library of exam images and associated feature vectors; images in the database are ranked by similarity to the query image, e.g., based on Euclidian distance between the weighted feature vectors of the query and database images via a k-nearest neighbors method; Retrieval of Similar Images: Based on the similarity ranking, all or a subset of images are returned, along with their rankings; Retrieved Image Interface: Images are displayed to the user, ordered by similarity to the query image (this interface is discussed more below). FIG. 13B shows exemplary code that may be used to identify similar TM images from a database/library of TM images, as described herein.

Automated Diagnosis

Figure 14A:
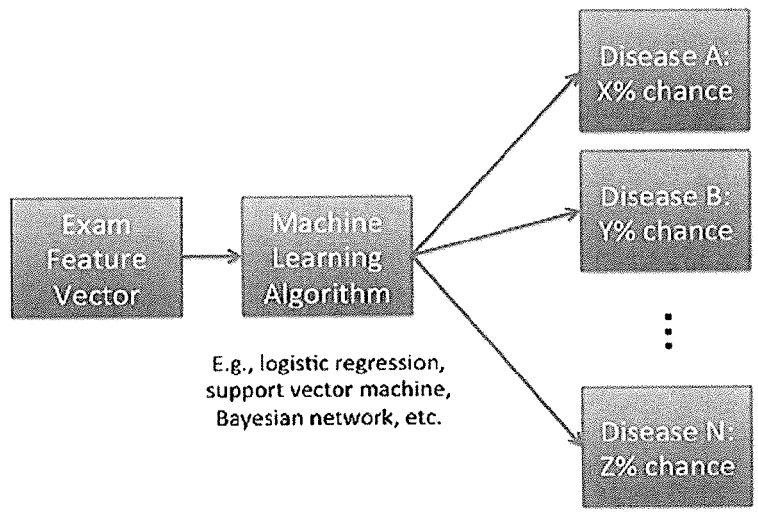
FIG. 14A schematically illustrates a method of assisting in diagnosis as described herein.

Once exam features (including features from images, clinical information or other tests) are collected and combined (either solely in a current exam, or including information from past exams), these features can be used in a machine learning system to predict the diagnosis associated with a given exam (FIG. 14A). In this case, the machine learning system would associate a real-valued "score" associated with each possible diagnosis; the score for a given diagnosis would be related to (but not necessarily the same as) the probability of that diagnosis being accurate for the given exam. The score may also contain a confidence interval. Displaying the results of the automated diagnosis method to the user is discussed below.

Any machine learning system tailored to classification (as opposed to regression) may be appropriate. Training of the system would proceed in a supervised sense, based on training with a "training set" of exam features associated with known diagnosis. Confirmation of low prediction error would be confirmed by testing the trained system in an independent benchmark test set that was not otherwise involved in the training. For example, FIG. 14B shows exemplary code for training classifiers to identify robust features that may be used in predicting and aiding in diagnosis. FIGS. 14C and 14D show exemplary code that may be used for processing a TM image to extract features for automated diagnosis.

An interface for displaying the results of diagnosis prediction is illustrated and described below.

Figure 15:
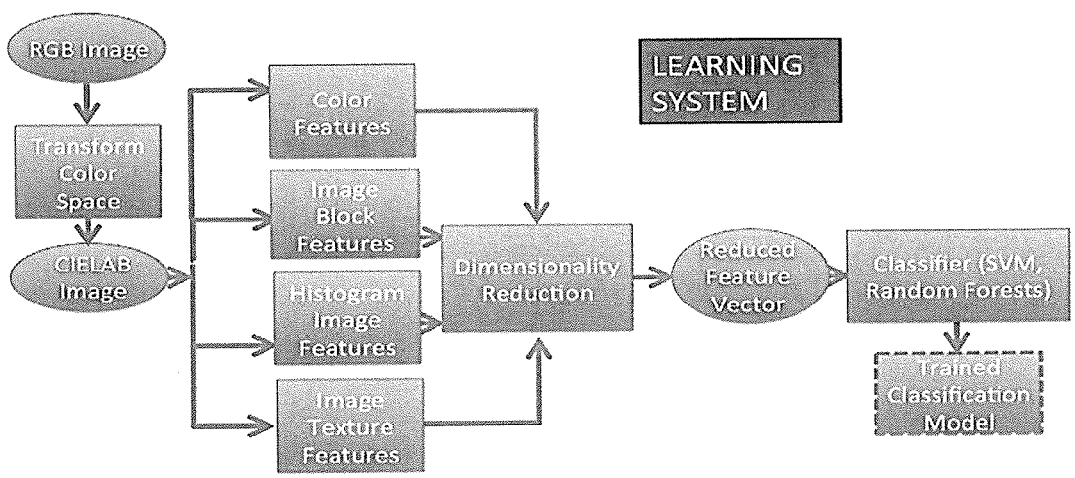
FIG. 15 schematically illustrates a learning system to train a classification model.
Figure 16:
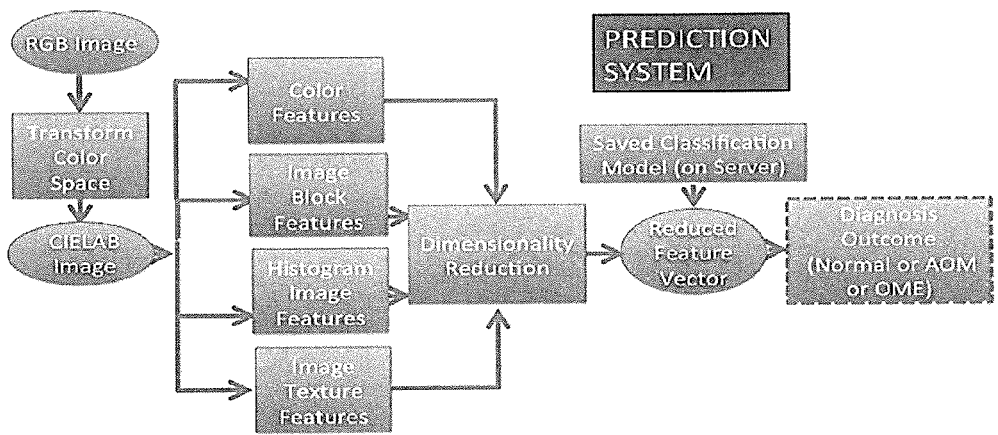
FIG. 16 schematically illustrates a prediction system for assisting in diagnosis of an ear ailment.

There are multiple variations in designing an automated diagnosis classification system. One such specific architecture of the diagnosis classification system is shown in FIG. 15 and FIG. 16 which depict a two-stage pipeline: a learning system and a prediction system.

Learning System

Step A. The first step in the learning system may involve (but does not require) transforming a dataset of input RGB images into a perceptually uniform color space, such as CIELAB. The CIELAB images become the transformed input for extracting image-based features.

Step B. Four categories of image features are depicted in the learning system (though systems can be effective with fewer or more).

1. Simple color statistics such as mean and median of the image color channels within a region of interest.

2. The image is divided into blocks of a certain size (example 32×32) and regions that have certain characteristics that do not imply the presence of eardrum could be excluded automatically. The simple mean and median can now be computed for these remaining blocks.

3. The normalized histogram of a certain channel of the CIELAB image are computed and each bin of the histogram is used as a feature.

4. The texture is a distinct category of feature from the above color intensity based features. Texture can be useful to, for example, capture variations in the vascularization of the tympanic membrane. Texture features may include gray-level co-occurrence matrix (6) contrast, energy, correlation and homogeneity.

A second class of texture features consists of computing the standard deviation within blocks of the image (example 64×64) and subsequently computing the mean and variance of the blocks. These are referred to as variance of block standard deviation and mean of block standard deviation.

Step C. The features are concatenated horizontally to obtain the feature vector. The redundancy of this feature vector could be reduced by some method of dimensionality reduction. A standard method such as principal component analysis could be used. Some other method such as linear correlation of the each feature to outcome could be used to select features that have a relatively high positive or negative correlation to diagnosis outcome. The resulting output is a reduced feature vector consisting of either orthogonal principal components or moderately to highly correlated features.

Step D. A classifier is now applied on the reduced feature vector to train the system. The various classifiers that could be utilized including but not limited to are: Logistic regression; k nearest neighbors; Support vector machines; Neural networks; Naïve bayes; Ensemble bagging; Ensemble boosting (AdaBoost, LogitBoost, etc.); Random forests (Tree bagger);

The classifiers would be trained and tested using k-fold cross-validation or a leave one out cross-validation or some other method. The final trained model is saved for the prediction stage.

Step E. The efficacy of the cross-validated model based on the diagnosis outcome could be evaluated using a few performance metrics. Metrics may include the Area under the curve (AUC) of the Receiver Operating Characteristics (ROC) Curve, accuracy, sensitivity, specificity, positive predictive value, negative predictive value etc.

Prediction System

An input test or query image may be processed through the prediction stage of the system (FIG. 16). Steps A through C as described in the learning system section above may be performed on the query image. The reduced feature vector is input into the saved training model. The machine-learning model outputs a diagnosis outcome (example: normal versus AOM).

The prediction system would also be used to measure the performance of the saved training model and ascertain that it is not over-fitting. To achieve this, the prediction system could be run on an independent benchmark test set that contains images that were never used in the training dataset. The overall performance can be measured using one or more of the performance metrics as described previously in Step E of the learning system.

Figure 17:
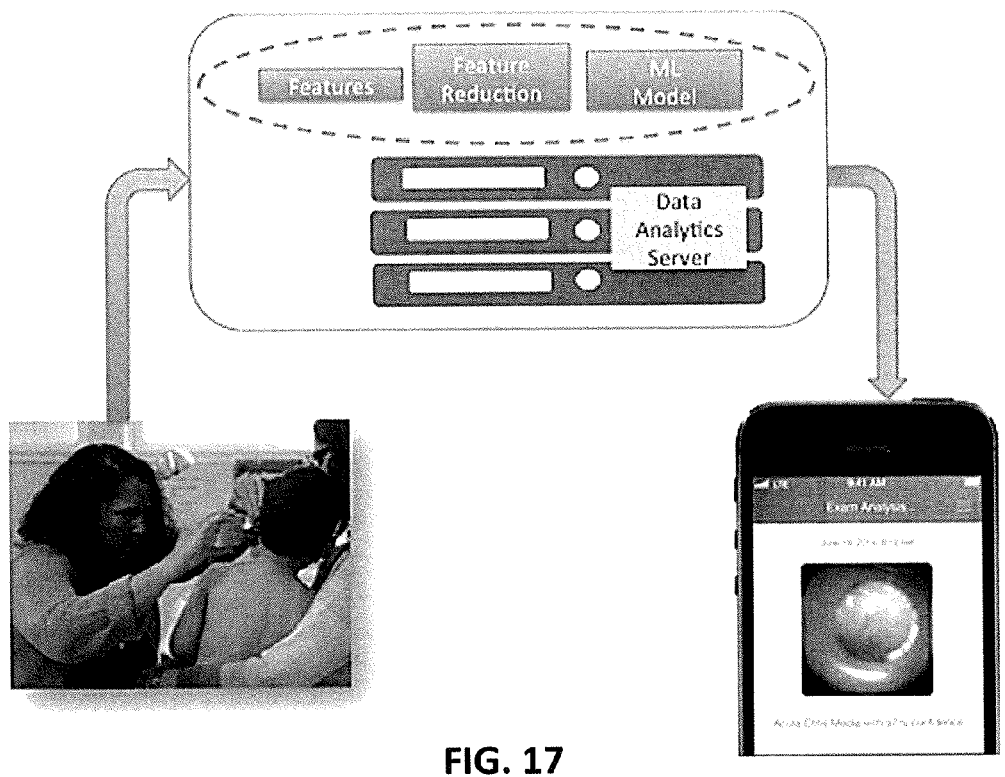
FIG. 17 illustrates one example of system usability workflow for a diagnosis assistance system as described herein.

The automated diagnosis system usability workflow is depicted in FIG. 17. The ear exam in the doctor's office (query images or videos) would be transmitted to the data analytics server, which hosts the diagnosis classification model. After processing through the diagnosis classification model, the exam analysis (with diagnosis outcome) would in turn be transmitted back to the mobile phone.

Alternatively, the diagnosis classification model could be stored on the mobile device. In this case, the analysis could be performed completely on the mobile device without requiring any network communication with the server.

Automated Prognosis

Similar to the methods described for automated diagnosis, a machine learning system may take in features from a current or past exam and use them to predict prognosis, i.e., when a disease is expected to resolve given a particular set of zero or more interventions. For example, in the case of otitis media, interventions might include but are not limited to: No intervention ("watchful waiting"); Antibiotics (of various forms); Tympanostomy tubes; Tympanocentesis; etc.

The main difference between prediction of prognosis and prediction of diagnosis is that diagnoses come in distinct classes, whereas prognosis is a real number, e.g., days to resolution. Predicting diagnosis therefore requires a classification method, while predicting prognosis relies on a regression method (example: support vector regression). In both cases, information from a single exam (and possibly exam history) is used as input, and predictions are made based on different scenarios; different diseases in the case of diagnosis prediction and different interventions in the case of prognosis prediction.

Figure 18:
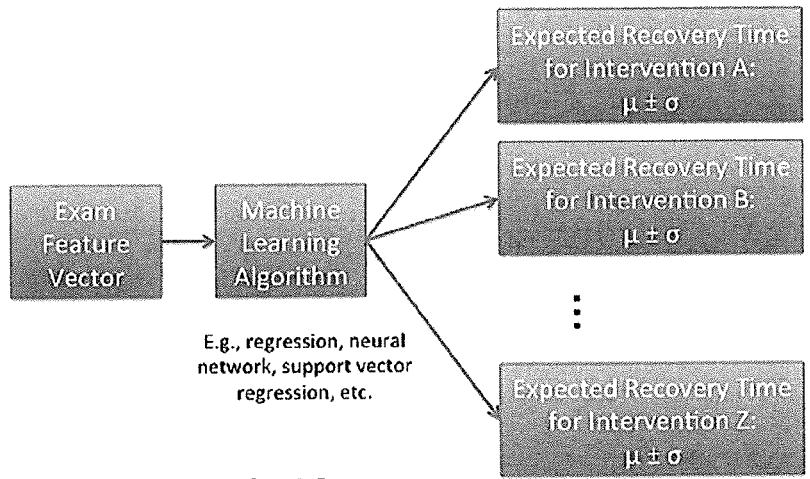
FIG. 18 illustrates one method of predicting prognosis using the systems and methods described herein.

The basic flow diagram for predicting prognosis (FIG. 18) is analogous to that for predicting diagnosis, except that the machine learning system is a regression method instead of a classification method and the returned information is expected recovery time for a given intervention instead of a likelihood score for a given disease. The mean and a confidence interval can both be calculated and returned for the expected recovery time. An interface for intuitively displaying the results of prognosis prediction is discussed below. Predicting prognosis may also take the form of classification, e.g., a true/false estimation or probability that a disease will resolve after N days.

Figure 19:
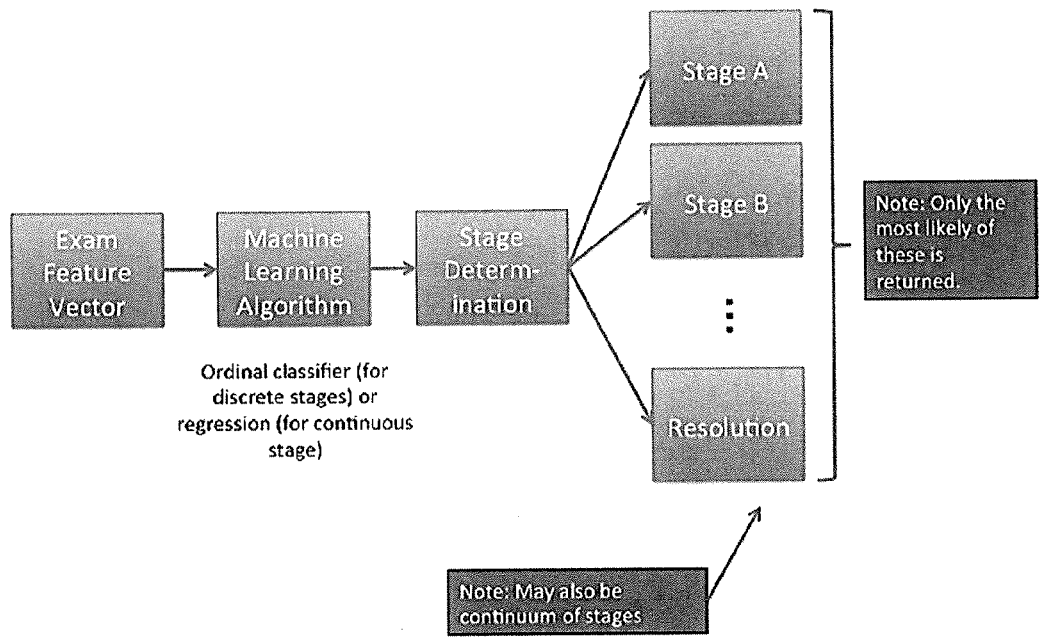
FIG. 19 schematically illustrates a method of automated determination of disease stage as described herein.

For many diseases, there may be several "stages" of the disease, ranging from the most acute form of the disease to resolution. One could also interpret the disease stage as lying on a continuum between acute and resolution, without requiring discrete stages. If the disease stages are discrete, a method to predict disease stage would be a classifier and would function similarly to the automated diagnosis classifier except that the response is ordinal (ordered) as opposed to nominal (unordered); see FIG. 19 for an example. Ordinal response mandates a somewhat different classifier (e.g., (Archer K J. rpartOrdinal: An R Package for Deriving a Classification Tree for Predicting an Ordinal Response. J Stat Softw. 2010 Apr. 1; 34:7) or using ordered regression models with the R ordinal package) than would be used to predict nominal response.

If the disease stages are continuous, this method would be a form of regression and would function similarly to the automated prognosis method, except that the response for only one disease would be shown, as opposed to the response for multiple interventions as detailed herein. The response would then be the expected disease stage, which would be a real number, e.g., from 0 to 1, plus or minus a confidence interval.

Once a diagnosis is made and an intervention is prescribed, it is helpful to track the progression of the disease via continuous exams and to suggest altering interventions if the disease is progressing or otherwise not improving as rapidly as expected. Methods and software tools can be a powerful aid in this tracking.

Figure 20:
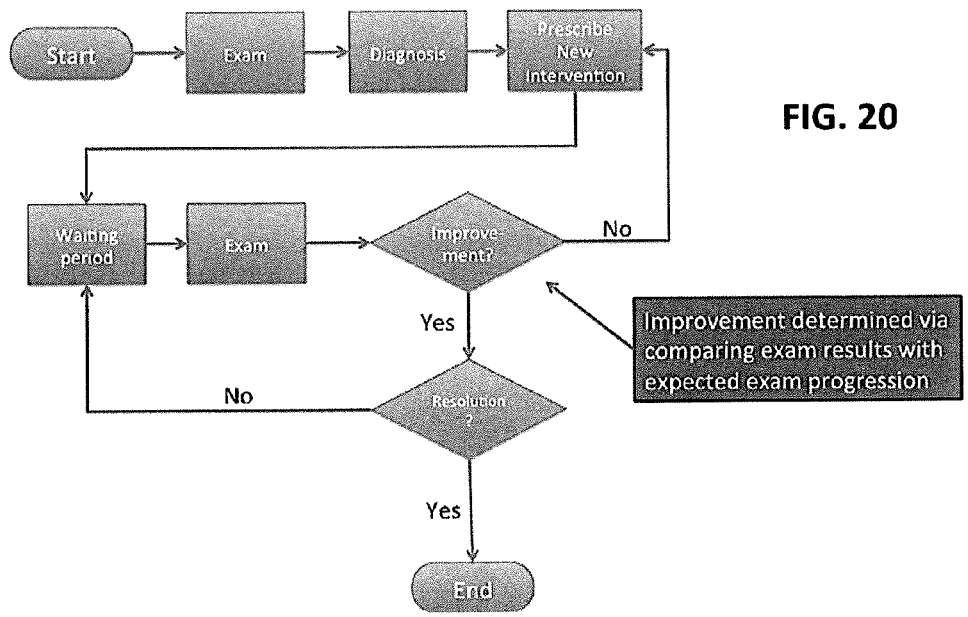
FIG. 20 schematically illustrates a method of continuous monitoring for intervention modification as described herein.

A method for continuous monitoring is shown in FIG. 20. Initially, an exam is performed, a diagnosis is made (possibly with help from the automated diagnosis method, described herein) and an intervention (including, possibly, no intervention or "watchful waiting") is prescribed (possibly with help from the automated prognosis method). After waiting for some period, e.g., one day, the exam is repeated. If the disease is improving as expected (possibly as determined with help from the automated method to determine disease stage) but has not yet resolved, the waiting period plus exam cycle may be repeated. If the disease is not improving as expected, a new intervention is prescribed based on the results of the most recent exam and, possibly, prior exams (again, possibly with help from the automated prognosis method). If the disease has resolved, the process is complete.

Creation of "Panoramas" from Small Field of View Images

Many types of image-centric examinations, including otoscopic and ophthalmoscopic (retinal) examinations, capture images with limited field of view (FOV) due to the need to image through narrow body cavities (e.g., the ear canal or eyeball), or with specula. As a result, the anatomical part of interest, e.g., the TM or the retina, may not fit within the field of view of a single image. To mitigate this limitation, one can capture multiple sections of the anatomical part of interest and then "stitch" them together into a composite image (i.e., a "panorama" or "mosaic"). This technique is already popular for creating panoramic images via stitched standard images in consumer cameras. However, medical images represent unique challenges due to intricacies of the images, e.g., the circular nature of the otoscopic images due to the specula and the smoothness of the tympanic membrane.

Existing methodologies for stitching together photographs into composite panoramas (e.g., Brown M, Lowe D G. Automatic panoramic image stitching using invariant features. Int J Comput Vis. 2007) could be adapted for the case of these narrow FOV images. Such a procedure would consist of several steps, given a set of images from which to compose a panorama: Feature detection (e.g., SIFT (Lowe D G. Distinctive Image Features from Scale-Invariant Keypoints. Int J Comput Vis. 2004; 60(2):91-110), SURF (Bay H, Ess A, Tuytelaars T, Van Gool L. Speeded-Up Robust Features (SURF). Computer Vision and Image Understanding. 2008 June; 110(3):346-59), ORB (Rublee E, Rabaud V, Konolige K, Bradski G. ORB: An efficient alternative to SIFT or SURF. IEEE; 2011. pp. 2564-71) or others); Feature matching; Homography estimation; Bundle adjustment; and/or Compositing.

Figure 21:
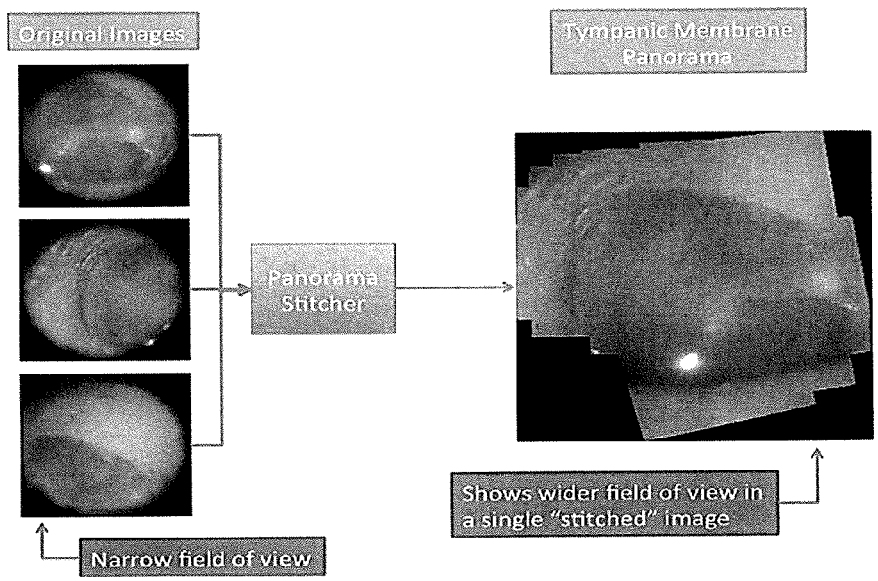
FIG. 21 shows an example of forming a tympanic membrane panorama from a plurality of individual images of the ear canal.

An example of the expected result of otoscopic TM stitching is shown in FIG. 21. The methods of creating a panorama image from a multiple otoscopic images or one or more otoscopic videos has required several innovations: Selection of optimal "key frames" to stitch into the final panorama using appropriate criteria, such as: High sharpness, Minimal motion blur, Large number of high-quality "features" (e.g., SURF (29) or others), Appropriate overlap with other key frames, and Complete coverage of the entire panorama area without gaps; Modification of existing panorama creation methods to deal with the circular or otherwise non-rectangular field-of-view; Modified feature detection or feature matching to allow for matches between smooth frames, e.g., those containing a healthy tympanic membrane; and/or Alternate methods of matching frames e.g., via optical flow for videos.

In one embodiment, the system and method may include the following steps:

(1) The input is a video (2) A set of relevant frame numbers containing the anatomical entity of interest are determined, for example, using the criteria described above. Further processing proceeds only on those frames deemed relevant in this step.

(3) The Field of View is detected within the image, e.g., using the method described above. Alternately, a pre-computed field of view may be used. Subsequent feature detection and optical flow steps are performed within the field of view.

(4) Optical flow is performed to estimate the displacement of each frame from the previous frame.

(5) The global coordinates of each frame are estimated using the inter-frame displacements.

(6) Keyframe selection proceeds as follows. Frames that are on the periphery of the covered global coordinate range are added as keyframes. Additional frames not on the periphery are added to the list of keyframes if (a) they are not too close in terms of frame number to an already-chosen keyframe (based on a predetermined distance threshold) and (b) the frame's sharpness is above a threshold.

(7) Keyframes are sharpened to aid in feature detection.

(8) Image features, such as SIFT, SURF, ORB, or similar, are detected.

(9) Features are matched.

(10) Matches are filtered based on their confirming to a limited affine mapping (i.e., the extent of rotation, scaling, etc., must fall within some predetermined range). Keyframe mapping is estimated based on matched features.

(11) Keyframes that could not be connected using the above mapping are instead mapped to adjacent keyframes using optical flow.

(12) Camera parameters are estimated from the keyframe mappings.

(13) Camera parameters are refined by bundle adjustment

(14) Keyframes are composited into the final mosaic

This embodiment is illustrated in the flow chart of FIG. 22.

An alternate embodiment is shown in FIG. 23. In this embodiment, the Keyframe Extraction procedure from the embodiment above is replaced with a procedure wherein sharp frames, as determined via the techniques above, are used to select key frames. The remaining steps are the same as in the previous embodiment.

Otoscopic and other visible-light-based medical images can be acquired with the acquisition device held in any orientation. For example, if the acquisition device is a mobile phone with an otoscope attachment, the phone may be held with the top of the phone in the patient's superior (towards the head) position, or the phone may be held with the top of the phone in the patient's anterior (towards the front) position, or in any other orientation in a 360° circle (see FIG. 24). Once the image is stored, there is, by default, no information encoded about the orientation of the acquisition device; it is therefore difficult to determine which direction is "up" (the patient's superior direction) when examining an image.

There are several possible methods of recording the superior direction in images. For example, the user may be permitted to manually enter the superior direction in the image based on their a priori knowledge of the exam or their interpretation of the image. This information entry could be performed either by manually entering "degrees from superior" of the "up" direction of the image, or by using an interface that allows them to either click or tap on the superior direction or rotate the image until superior is up.

If the recording device has an accelerometer, the device's orientation with respect to the ground may be recorded during the exam. The direction of zenith (perpendicular to the ground) can be recorded with the image as image metadata, for example, as degrees with respect to the "up" direction in the image. For patients standing or seated upright, it can then be inferred that the superior direction is the same as the zenith ("up") position recorded by the device.

An automated method could be used to detect the malleus, which is generally oriented in a specific way with respect to the superior direction.

The examiner could be instructed to take a picture of the patient's external ear with the device in the same orientation as that used during the otoscopic examination. The orientation of the ear could then be determined either manually, by allowing the examiner to indicate the superior direction, or the orientation could be determined via a machine learning system to detect the orientation of the external ear and the orientation could be applied to the otoscopic image. If the exam consists of a video, then the examiner could be instructed to ensure that the patient's external ear fills the frame during the initial or final portion of the video, and the above procedure could be applied.

An electronic "marker" of some form could be attached to a known (e.g., superior) portion of the patient's external ear during the exam, and a device could be incorporated into the otoscope probe to detect the orientation of the probe with respect to the marker Once the patient superior direction is known with respect to the image "up" direction, that direction can be conveyed to orient the image when it is displayed to the user via the methods described herein.

3-Dimensional Reconstruction of Ear Canal and Tympanic Membrane

3-Dimensional reconstruction of a scene image or video has traditionally made use of stereoscopic cameras with known separation distance between the lenses (e.g., http://en.wikipedia.org/wiki/Stereo_camera). With advances in image processing techniques, particularly multi-image registration via image features, it is now possible to reconstruct a 3D scene using a single camera/lens that has imaged a scene from two or more vantage points.

This procedure could be performed, for example, in the case of multiple images and/or one or more videos of a digitized otoscopic examination. By moving the camera within the ear canal, it should be possible to observe parts of the ear canal or TM from multiple different angles (FIG. 25). Image features, e.g., SURF features could then be found, matched between images, and registered. Registered features from multiple angles allow for estimation of the 3D position of each matched feature, thereby permitting 3D reconstruction of the imaged scene. Textures can be overlaid from the original images or videos to create a textured 3D reconstruction. An example of this 3D textured reconstruction in a more general context is the "Seene" iPhone app (http://seene.co/).

Once it is created, a 3D textured model of a patient's ear could be used to allow physicians or other users to perform a "virtual otoscopic exam". Another possible method of 3D otoscopic imaging using multiple camera optical elements is discussed below.

Otoscopic Exam Guidance System

When an individual performs an otoscopic exam for the first time, it may be difficult for them to determine whether they are performing the exam correctly. Specific challenges may include: trouble moving the otoscope within the ear canal without bumping into the wall of the canal (which can cause pain or irritation in the patient); not knowing how to find the tympanic membrane (i.e., in which direction they should point the otoscope to bring it into view); not knowing how to properly tug on the patient's ear to straighten the ear canal; not recognizing the tympanic membrane even when it is in view; not being able to identify common obstructions, such as cerumen (wax); and/or not knowing when an exam recording is "good enough" for a reliable diagnosis so that they can end the exam recording.

A properly trained real time guidance system that is integrated with a digital otoscope can solve these problems. Such a guidance system could provide "heads up display"-style cues (e.g., arrows, "locked on" indicator, or other graphics superimposed on the live video of the in-progress exam) or audio cues (e.g., a chime, or a voice instructing the user to move the otoscope left, right, into the ear, out of the ear, etc.) to guide the user during the exam. This would help to ensure that the necessary anatomy is visualized during the exam and that the exam is conducted in as expedient and safe a manner as possible.

Described below are different aspects of the real-time guiding system to address the above enumerated challenges inhering in performing an exam.

One can analyze the video recording to detect and track the "region of increasing depth," i.e., the location in the video recording that leads deeper into the canal (towards the tympanic membrane) to provide orifice (e.g. ear canal) guidance. This could be accomplished by finding and tracking the darkest, sufficiently large region in the video; that region would likely be the location of maximum depth (i.e., towards the interior of the ear canal) because the intensity of light from the otoscope falls as the square of distance from the otoscope, causing far-away features to appear darker. The detected region would have to be "sufficiently large" to avoid false positives from noise. One could also require that the region be detected in multiple sequential frames to mitigate noise.

Alternatively, a more sophisticated approach to detecting the region of increasing depth would consist of creating a supervised machine learning classifier. In this case, for training the method, one could record many videos and create a gold standard wherein the region of increasing depth is manually segmented in the videos. The region of increasing depth classifier would then be trained and operated in an analogous manner to that described above for TM segmentation.

Once detected, the region of increasing depth could be tracked using "optical flow," which tracks the movement of the scene, relative to the observer, in a video. As the camera moves right, for example, the optical flow method detects this movement based on features in the scene appearing to move left (from the perspective of camera's coordinate system).

Based on the known location of the region of increasing depth with respect to the currently observed scene, some indication could then be given to the user of the direction of the region of increasing depth. For example, if the user is pointing the otoscope at the side of the ear canal and the region of increasing depth is known to be to the left of the current location, an arrow pointing to the left could be displayed on the screen (FIG. 26), or an audio cue could sound, instructing the user to move the otoscope to the left or to tilt the phone in the appropriate direction.

Analogously, if there is something immediately in front of the tip of the otoscope (e.g., the ear canal, cerumen, foreign body, etc.), the user could be advised not to push the otoscope in any further or to change its orientation or draw it out of the ear. Detection of an object immediately in front of the speculum tip could be accomplished in a few ways: via a supervised machine learning approach, as described above in the TM segmentation method; by detecting whether a particular area of the image is significantly brighter than its surroundings, which may indicate either a specular reflection (e.g., the "cone of light" from the tympanic membrane) or an object significantly closer to the tip of the speculum than other objects in the image; by reading focus information from the camera and detecting whether the focal distance is very short (close to the lens).

One embodiment of guidance (e.g., using the ear canal) consists of the following steps:

(1) The input may be an image (which may be a still frame from a video).

(2) The Field of View may be detected within the image, e.g., as described above. Alternately, a pre-computed field of view may be used. Subsequent processing proceeds within the detected field of view.

(3) The image may be converted to grayscale.

(4) The image may be processed with a median filter, which should reduce impulsive noise, particularly including hairs or other small objects that cause slight occlusions in the image.

(5) The image may be corrected for uneven illumination using a precomputed "average illumination" image. The average illumination image represents the image that would be recorded if the subject is (geometrically) flat, uniform and gray or white in color. The input image is divided by the average illumination image to remove the effects of uneven illumination on the subject.

(6) A quantile image may be generated from the image. In the quantile image, each pixel is set to the value of the empirical cumulative distribution function at the original pixel value. E.g., if a pixel's value is 113 (out of 255) and 72% of all pixels have a value of 113 or less, then the value of that pixel in the quantile image would be 0.72.

(7) The quantile image may be thresholded to generate a true/false mask in which pixels are true if the quantile image is below the threshold. A reasonable threshold may be 0.1 (i.e., pixels in the 10th percentile of brightness will be included in the mask).

(8) The mask may be morphologically opened and closed to eliminate spurious holes, gaps and small connected regions.

(9) Distinct connected regions may be detected.

(10) Features may be extracted from each connected region. Features may include, but are not limited to: region area (number of pixels); region eccentricity (the eccentricity of the ellipse that has the same second-moments as the region); region solidity (proportion of pixels in the convex hull that are also in the region); mean intensity of original grayscale image; mean intensity of the illumination-corrected image.

(11) The features are fed into a pre-trained supervised machine learning classification model (e.g., a support vector machine or random forest model) to predict whether the given connected region represents a region of increasing depth in the image (as opposed to, e.g., a dark region of the subject or an artifact due to uneven illumination or proximity to the edge of the field of view).

(12) The output of the machine learning model is used to discard connected regions that do not likely represent regions of increasing depth.

(13) Centroids of the remaining connected regions are computed.

(14) The centroids are used as input into a UI that guides the user towards the region of increasing depth.

Figure 27A:
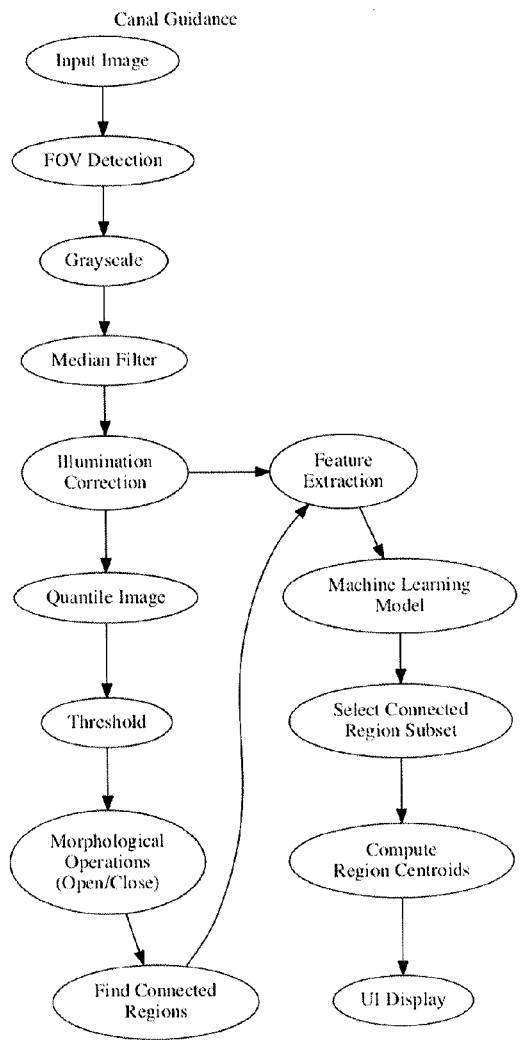
FIG. 27A schematically illustrates one method of guiding a subject using an otoscope to image a tympanic membrane.

This embodiment is illustrated in the flow chart of FIG. 27A. This example uses the depth of the field of view (darker regions) to guide a user toward the TM, which is deeper in the ear canal. FIGS. 27B and 27C show exemplary code for performing such a method. In addition, or alternatively, the apparatus may be configured to examine the images (or a subset of the images) being received and/or displayed, to identify a TM or a portion of a TM, as described herein. The apparatus may be configured to determine directionality (e.g., to center the TM) based on the position of the identified probable TM region on the screen, and provide indicators (e.g., arrows, icons, audible instructions/guidance) to guide the subject in positioning the otoscope. Additionally or alternatively, the apparatus may automatically take one or more images when a substantial portion (e.g., above a threshold of the TM or percentable of the image field of view) is present.

Figure 28:
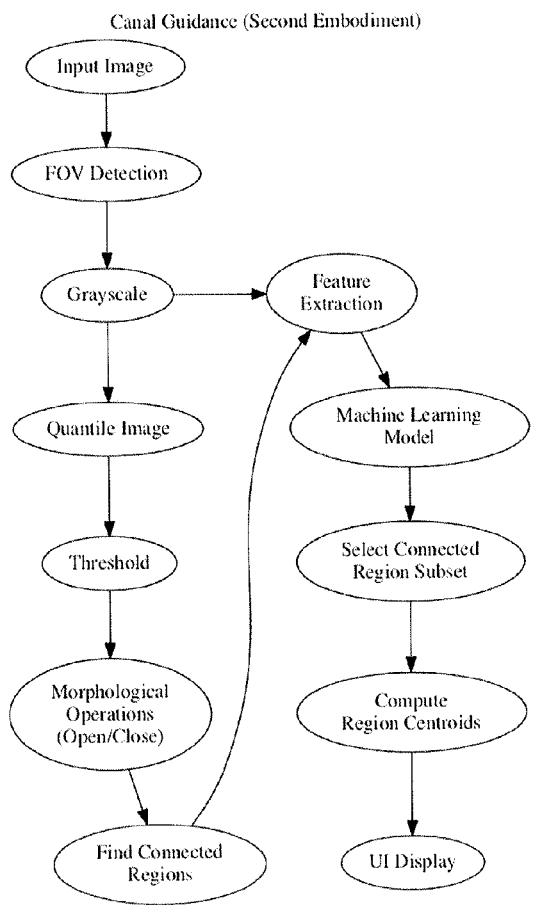
FIG. 28 schematically illustrates another method of guiding a subject using an otoscope to image a tympanic membrane.

An alternate embodiment is shown in FIG. 28. In this embodiment, the "median filter" and "illumination correction" steps have been removed. This is a simpler embodiment that may function similarly to the main embodiment if the illumination source is nearly uniform and the "morphological operation" step contains a morphological closing step with large enough kernels that median filtering is effectively performed as a side effect.

Similarly to how a user can be guided towards the tympanic membrane when performing an exam, they could also be advised how to properly tug on the external ear canal to straighten the ear canal and obtain the optimal view of the tympanic membrane. Text recommending that the user, e.g., "tug the earlobe towards the patient's back," could be displayed overlaying the live image, analogous to how the directional arrow is displayed in FIG. 26.

This guidance system may significantly aid users who do not know a priori the optimal way to straighten the patient's ear canal. Even when a user has properly straightened the ear canal, they may not be aware that they are straightening it properly. In this case, a message such as "ear canal successfully straightened" could be displayed.

The logic for the guidance system could be trained via a supervised machine learning approach, as described above in the tympanic membrane segmentation method or some other method. In this case, training data would consist of multiple videos of the same patient ear, where the patient's ear had been pulled in a different way in each video. For example, for patient A, there may be three videos, one for each of the following four scenarios: Ear not tugged, Ear tugged up (patient superior), Ear tugged back (patient posterior), Ear tugged down (patient inferior).

Using quantitative features acquired as described above, the machine learning method could be trained to predict the known optimal tugging direction.

The apparatus and method of detecting the TM, described above, may perform in real time during an otoscopic examination. In that case, it would be possible to indicate to the user, in real time, (a) that the TM has been detected and (b) where, in the live video, the TM is located. The interface for indicating the TM could be similar to that of FIG. 1, and might include: highlighting the boundaries of the TM, highlighting the area of the TM, noting the center of the TM, e.g., with an icon such as a checkmark, smiley face, etc.

Additionally, a threshold could be determined wherein, when the area of the tympanic membrane (either absolute or relative to other image features) is sufficiently large, an indication is displayed to the user (either audio, e.g., via a chime or voice, or visual, e.g., via a check box or modal dialog) that the TM has been successfully captured and that they may now end the exam. Other methods besides absolute size of the TM may be used to determine when an exam may be completed, including the sufficiently high quality capture of a particular part of the ear anatomy (e.g., the umbo of the TM), or the cone of light, or any other feature as suggested by the entity responsible for using the image or video to make a diagnosis (e.g., the physician).

Obstructions within the ear canal, including cerumen or foreign bodies may either prevent the ear exam from being completed successfully (because they partially or completely occlude the tympanic membrane) or may present a hazard during the otoscopic examination because they may be pushed by the speculum deeper into the ear. A cerumen/foreign object segmentation method has been created and described herein, analogous to that of TM segmentation discussed herein, to detect these obstructions. In this case, the positive training class would be various obstructions instead of the TM. If the obstruction is particularly large, or occludes the TM, the user could be advised to prematurely end the exam to avoid injuring the patient or worsening the obstruction.

Thresholds to determine when an obstruction warrants ending the exam can be determined via a standard machine learning method, wherein the training set consists of a set of otoscopic exams and labels, where the labels indicate which exams have dangerous obstructions and which do not. Such a machine learning method canbe run in real time during an exam to indicate to the user whether and why they should prematurely end the exam.

Detection that a Lens is Attached

Any of the apparatuses described herein may also include a detector that is configured to detect when the image is being generated by a device having an attached lens (e.g., otoscope component, etc.). This may be referred to as an Oto-Detector when used for an otoscope. An Oto-detector may process the pixel buffer being read by the camera in real time to detect whether or not the otoscope component (e.g., lens and speculum) is attached to the imaging device/processor (e.g., smartphone). Once it detects the device the software can trigger the phone's torch (camera flash), begin recording, alert the user with a voice prompt or perform other useful actions.

The Oto-Detector may work as follows:

(1) Measure the average color RGB color value on 3×3 block of pixels in each of the four corners.

(2) Compare this average to a pre-defined threshold.

(3) If the average is below (darker than) the threshold then measure the average of a 3×3 block of pixels in the center of the screen; otherwise, do nothing.

(4) Compare the center average to a pre-defined center threshold. If the center average is greater (brighter) than the threshold, turn on the torch or perform other useful actions.

Figure 29B:
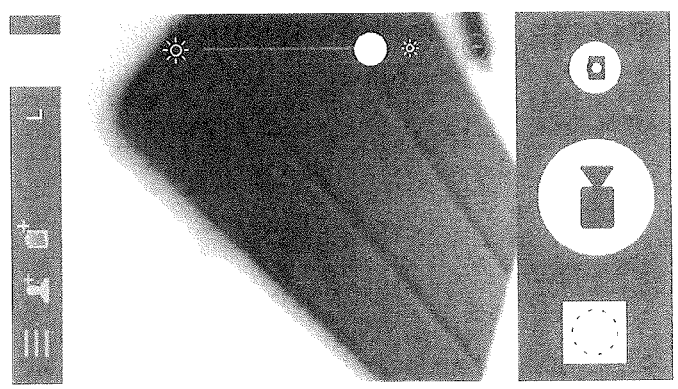
FIGS. 29A and 29B show different examples of lens attachment detection (e.g., otoscope detection).
Figure 29A:
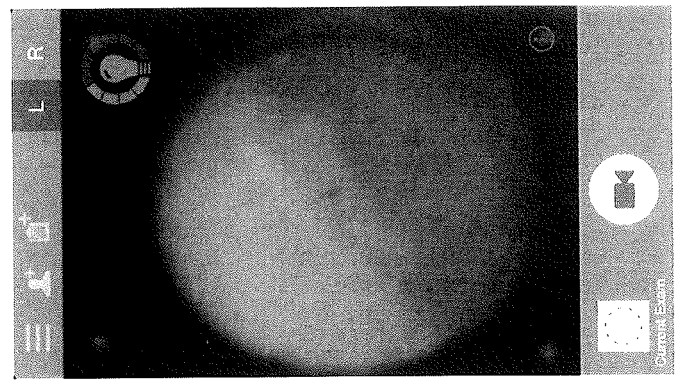

In essence, if the corners are black and the center is not, the device may be attached. FIGS. 29A and 29 B illustrate one example of detection of an otoscope, with the Otoscope device attached (left) and removed (right).

Any of these devices may also include an automated hardware camera hardware identifier reader. The following apparatus/method builds on the previously described one. For example, an Oto device can include a symbol within the viewable range of the camera sensor. This symbol can be read by the software to determine almost anything. For example, the symbol could contain a device type and version number so the app could automatically load the correct screen, add a filter, or begin recording and uploading to a server.

Figure 30:
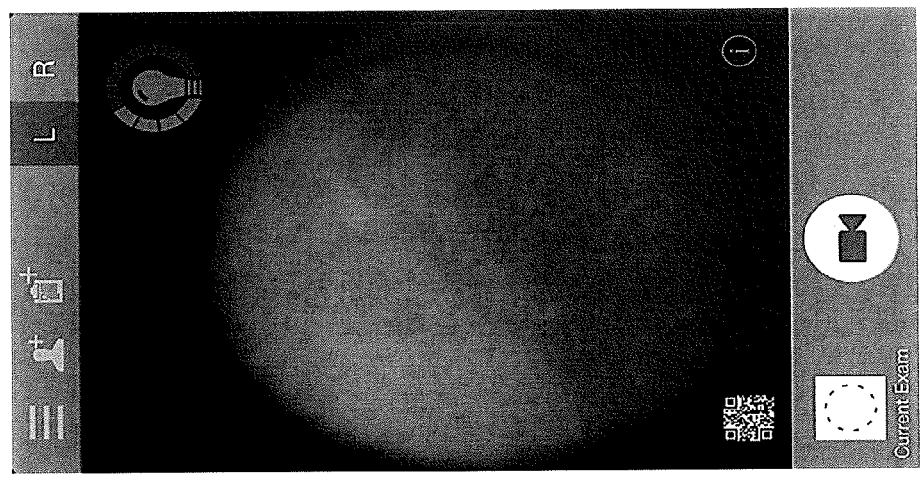
FIG. 30 illustrates an identification code for automated hardware identification during lens attachment detection (e.g., otoscope detection).

See, for example, FIG. 30. This QR code symbol in the lower-left would be attached to the Oto device itself, making it readable on any phone or tablet.

This is one method whereby the software application can present specific characteristics for different imaging applications or attachments. For example, in one version of the Oto hardware, the image formed on the camera is flipped and mirrored due to the optical design of the otoscope attachment. In normal use, the mobile app flips the image in X and Y to present it to the user "upright". When the Oto module is removed from the phone, the mobile app can detect its absence in the image, and change the imaging characteristics, for example ceasing to flip and mirror the presented image, so the user can now see the unmodified scene as expected. If the dermascope module is then attached, the app can see that the image need not be inverted, again depending on the imaging characteristics suited to the module and application.

Display and Interactive Interfaces

All below described display interfaces are suitable for mobile applications (e.g., iOS or Android OS, Google Glass), desktop applications (e.g., in Windows or Mac OS) or web applications. Note that the term "click" is used in some places, which may connote use of a pointing device; all below interfaces may also be implemented in mobile devices, in which case "click" is used interchangeably with "tap" and may include select, etc.

These interfaces are methods for presenting and interacting with the relevant information, as well part of the system of image collection, review, storage, analysis, and transmission.

Figure 31:
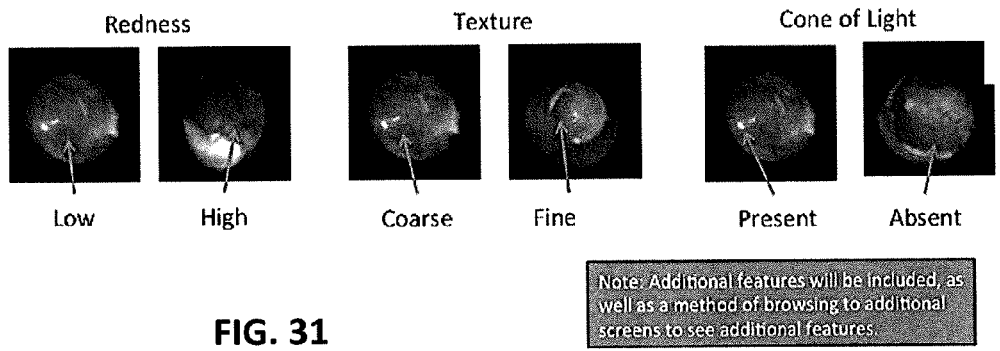
FIG. 31 illustrates one example of feature explanation.

A user-facing interface for the purpose of educating users about the meanings of different image features may be included. For each feature, two or more example images will be shown that distinctly show differences in the feature-of-interest. For example, for a "redness" feature, a normal ear image could be shown and labeled as having "low" redness, and a pathological ear image (e.g., with a diagnosis of AOM) could be shown and labeled as having "high" redness. An example interface showing three features is shown in FIG. 31. The user may also have the ability to select one of the example images to see a list of similar images that are also representative of that feature value.

Example images could either be chosen manually and hard-coded into the application, or they could be dynamically drawn from the database of images from which features have already been extracted. If drawn from the database, the displayed images would logically be chosen to be those that lie on the extreme ends of the distribution of values for that particular feature (e.g., images with very high or very low redness).

A given image (such as the one from the current exam), could be presented in this context, which each feature placed on a scale to illustrate the relative level.

Also described herein are interfaces for Content-Based Image Retrieval Results. For example, a user-facing interface for the purpose of displaying CBIR results to the user and for interacting with those results may be included. CBIR results are generated via the method described above.

Figure 32:
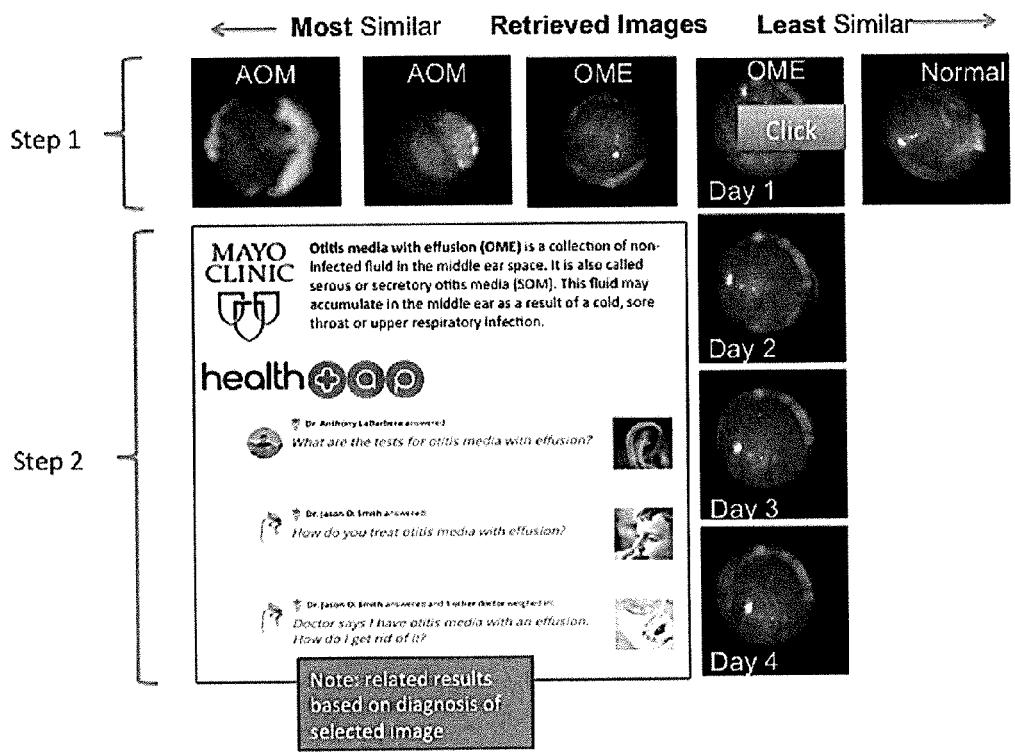
FIG. 32 illustrates an exemplary screen for displaying images of tympanic membrane.

Once the user has activated the CBIR process with a query image, similar images, along with their ranking and a "similarity score," will be available to the user interface. Initially, the user interface may show only a ranked subset of the retrieved images, possibly with their similarity scores and diagnoses or outcomes. The user will then be able to drill down, with a click or tap, to bring up more information about a returned image. That information could include additional images from the same patient, for example, if the patient was followed up with regular imaging. Additionally, information about the diagnosis could be displayed, e.g., from partner sites. Such information could include the formal disease name, common treatments, typical time to resolution, etc. The user may also be presented with partner information that allows them to contact a doctor, or ask a question about the returned image or the query image in a public or private medical discussion group. FIG. 32 shows this process.

By enabling more regular and frequent recorded images, the methods and apparatuses described herein may allow a new paradigm of image comparison and analysis. Previously, a user had no good way of seeing what an infection looks like over time. Now, he can submit his image to the systems described herein, find a similar case automatically, and see how that case resolved over a variety of time frames (minutes, hours, days, weeks, etc.). He can also see how similar cases fared with different interventions.

Figure 33:
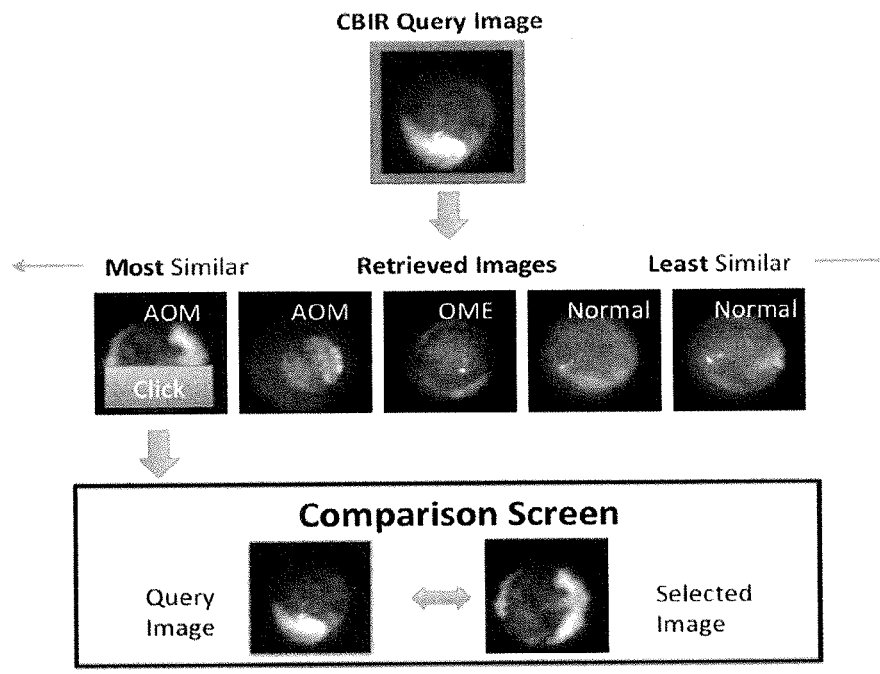
FIG. 33 illustrates one example of an access comparison screen for comparing an image of a patient's tympanic membrane to other (library) images.

By interacting with a returned CBIR result in a different way (e.g., via a contextual menu), the user could be immediately brought to an image comparison screen, where they can interactively compare the query image and the returned result (FIG. 33).

Figure 34:
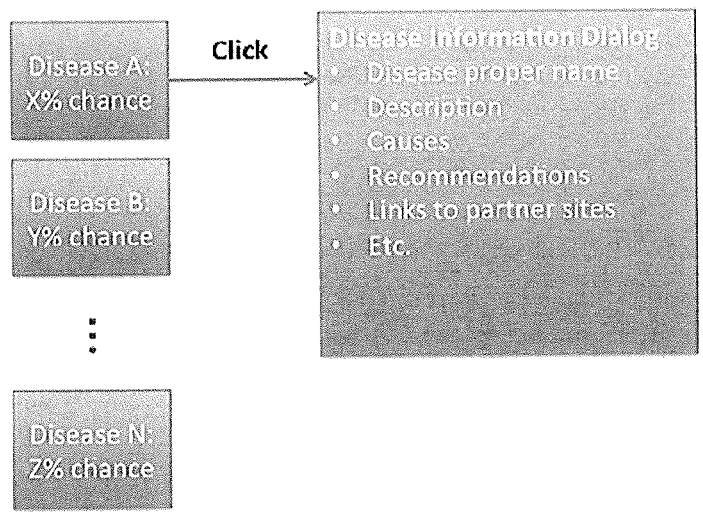
FIG. 34 schematically illustrates a diagnosis assistance display.

Also described herein are interfaces for automated diagnosis results. A user-facing interface for displaying results of automated diagnosis and allowing the user to interact with those results is illustrated herein. After the automated diagnosis method has run, each possible disease and diagnosis score will be displayed, possibly alongside a representative exam image for that disease. The user may then select any of the diseases, upon which a "disease information dialog" will be displayed, showing the disease name, description, causes, treatments, etc. FIG. 34 shows this process. Other information about the disease, or links to information from partners, analogous to that described in the CBIR interface, may also be shown.

Figure 35:
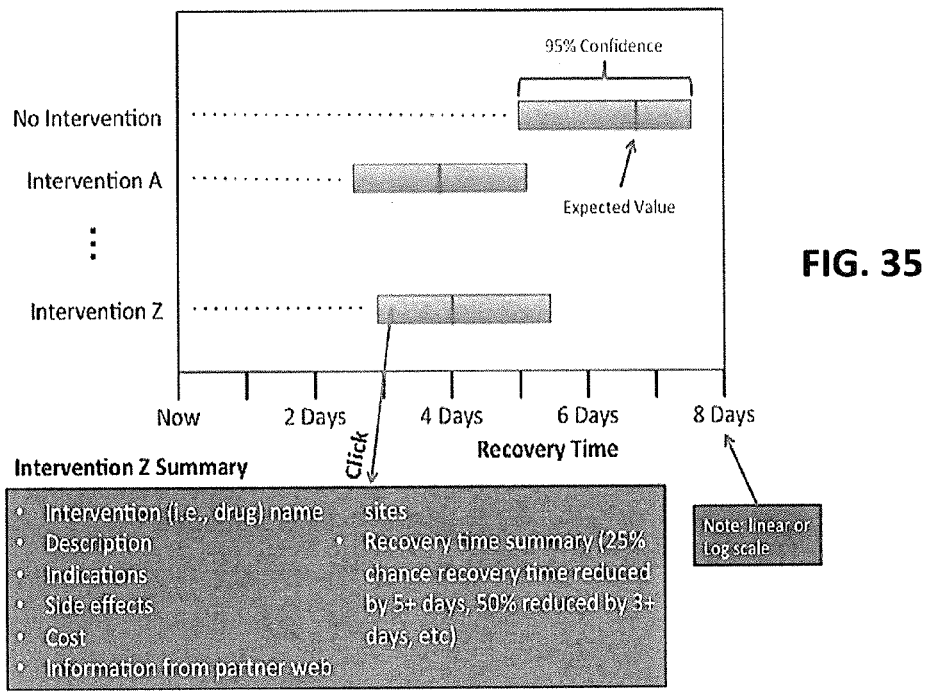
FIG. 35 is an example of an intervention effectiveness display.

Also described herein are interfaces for showing expected recovery time for different interventions. For example, a user-facing interface may visually convey to the user the expected difference in recovery times for different interventions (FIG. 35). The interface consists mainly of an interactive axis, on which "time to recovery" is on the x-axis and different interventions are on the y-axis. The displayed information is mean and confidence interval of the expected recovery time for different interventions. By visually comparing different interventions and noting the extent to which their confidence intervals overlap, the user can get a feel for which interventions might offer the most significant (either statistically significant, or "significant" in the colloquial sense) improvement in recovery times. They can use this information, along with other information about interventions (e.g., cost, side effects, invasiveness, etc.), in order to decide on the most appropriate intervention.

The user will have the ability to select an intervention, either by selecting the intervention name on the y-axis, or by selecting the bar denoting the recovery time confidence interval, to get more information about that intervention. Information may include the proper name of the intervention, description, side effects, information from partner sites (analogous to the partner information that shown in the CBIR interface), etc.

Additionally, either in this intervention summary, or via another method (e.g., a contextual menu), a statistical summary of the expected recovery time may be displayed, e.g., showing a human-readable summary of the cumulative distribution function for recovery times for that intervention, e.g., "25% chance of recovery in 3 or fewer days, 50% chance of recovery in 5 or fewer days, 75% chance of recovery in 15 or fewer days." This information could either be in absolute terms (number of days to recovery) or in the change in the number of days to recovery with respect to the expected (mean) number of days to recovery if no intervention is taken (e.g., "50% chance that recovery time is reduced by 3 or more days," etc.).

In addition, the system could distill this information to suggest a course of action, based on general results or user-supplied parameters (cost-sensitivity, watchful waiting tolerance, etc.).

Figure 36:
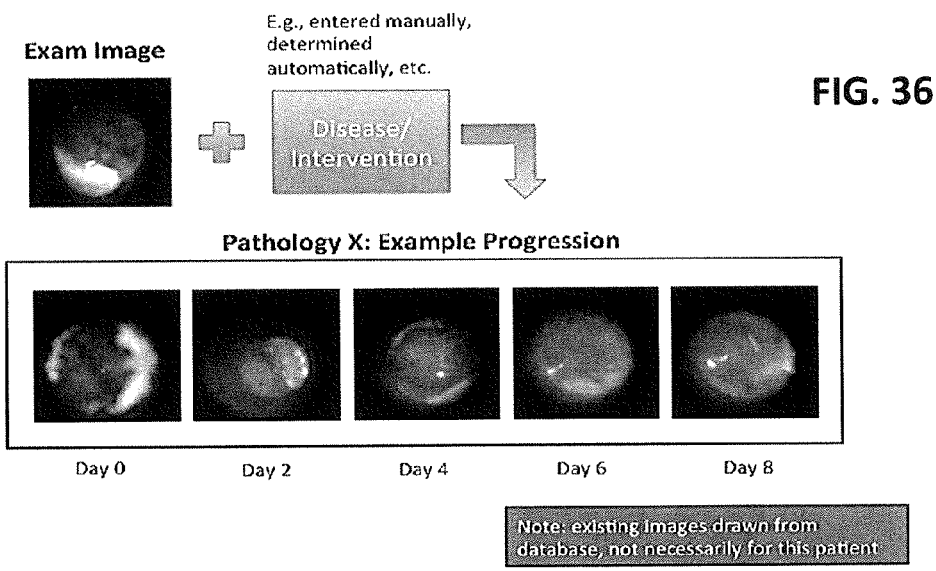
FIG. 36 is an example of a display showing expected recovery progression based on comparison with library (reference) images.

Also described herein are interface for showing example disease progression via images, for example, a user-facing interface for educating users about the expected progression of a given disease, possibly given an intervention, using example longitudinal imaging data from the database (FIG. 36). Given a disease name—possibly gleaned for an exam using the automated diagnosis procedure—and possibly an intervention, this interface will show longitudinal imaging from a single patient, with images spaced over time. The user will then have the ability to visually compare their exam to the example progression to estimate their stage in the disease progression.

Figure 37:
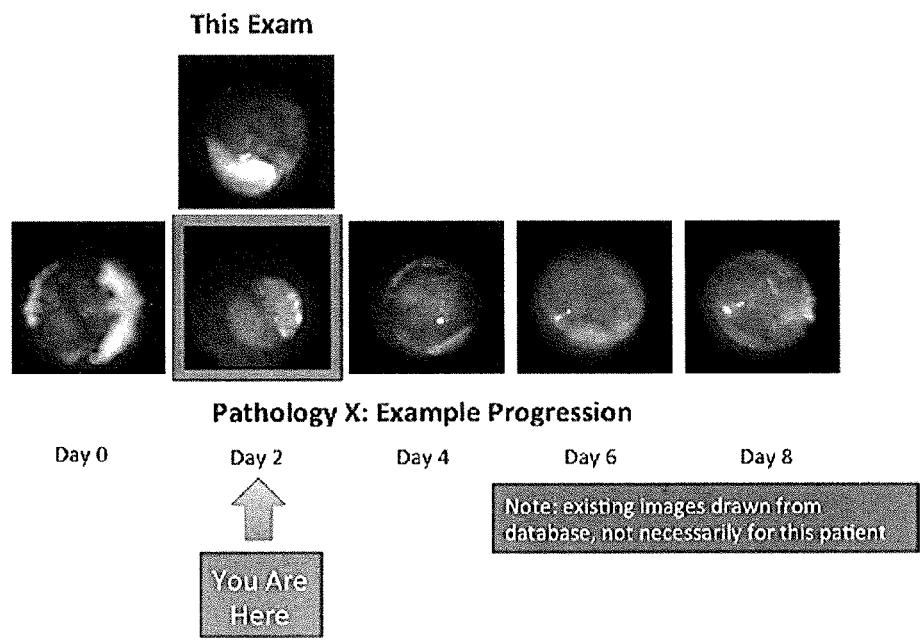
FIG. 37 illustrates one example of an expected recovery progression using library (reference) images.

This interface may also be extended to compare a query image to images within an example disease progression in order to automatically line up the query image with the appropriate image in the disease progression (FIG. 37). This will visually inform the user of the current stage of their disease. Determination of similarity between the query image and the images in the example progression would be made via the same similarity metrics used in CBIR, using an ordinal classifier. This interface would not be confined to any given example progression for a given disease/intervention, but could search for the closest image in all sets of longitudinal progression data associated with the given disease/intervention.

Figure 38A:
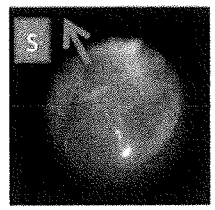
FIGS. 38A and 38B illustrate methods of indicating superior direction in an image of a tympanic membrane.
Figure 38B:
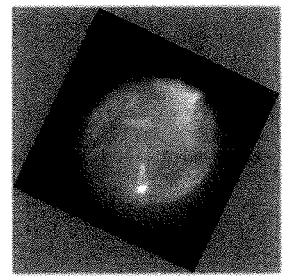

If the superior direction of the patient is known with respect to the image "up" direction, that superior direction could be indicated in one of two ways when the image is displayed (FIGS. 38A and 3AB): an arrow could be overlaid on the image, pointing towards the superior direction, as shown in FIG. 38A, or the image could be automatically rotated such that the superior direction is up, as shown in FIG. 38B.

Via methods described herein, it is possible to create a textured 3D model of a patient's ear canal and TM. Alternative methods including using high-resolution CT or MRI images to create the 3D model of the ear canal may be used; the model could then be textured using textures from any standard otoscopic exam. Such a 3D model could be used for training or to aid in diagnosis of a real patient.

Once a 3D model exists, a user can navigate through the reconstructed ear canal and view relevant anatomy from different angles. This navigation could be performed on any device (e.g., PC, tablet, mobile phone, heads-up display, such as Google Glass, etc.), and is not limited to the device used to record the original exam.

On a PC, navigation could be performed in a manner similar to that of a 3D modeling program, such as Solid-Works, or a 3D exploration program, such as Google Earth. Different combinations of clicking, dragging and mouse wheel scrolling perform functions of view zooming, panning and rotation.

On a mobile device, navigation could be performed in the "Google Earth style," where certain multitouch gestures allow panning, zooming or rotating the view. Alternatively, navigation could make use of the device's built-in accelerometer, so that, as the device moves or rotates, those movements can be captured and translated into corresponding movements of the view within the mobile application, allowing for a "virtual ear exam" using the previously built 3D model. This interface performs similarly to, for example, the Google Sky Map Android app (http://www.google.com/mobile/skymap/). The Google Sky Map app allows the user to point their mobile device at a portion of the sky and shows constellations and other relevant space phenomena in the direction that the device is pointing; the device's orientation is deduced by reading its accelerometer values. In the case of the virtual ear exam, the same principle is used, except that the "virtual space" consists of the textured 3D ear model.

When used for diagnosis of a real patient, the virtual ear exam allows unprecedented diagnostic ability when compared to a standard planar otoscopic exam, since standard otoscopic exams are not able to capture the 3D topology of the TM, and must instead rely on planar images for a diagnosis. If the TM is modeled in 3D, it is possible to view it from angles that are not achievable in a standard otoscopic exam due to the restricted movement within the ear canal. By zooming in to the TM and assessing it from low (off-zenith) angles, characteristics like TM bulging and tears can be assessed more easily than in planar images or videos.

Beyond increasing diagnostic capabilities for physicians, the virtual ear exam implemented on a mobile device can also be used as a training tool for clinicians-in-training or home users. The user can rotate and move the mobile device in the same manner that they would when performing a real ear exam, and the virtual scene displayed on the device could move in accordance to the user's movements, simulating what they would see if performing an ear exam on an actual patient. This allows them to "practice" performing an ear exam, which has the following advantages over training on a real patient: no need for real patients (resulting savings in cost and convenience); no risk of harm to real patients; ability to simulate different pathologies; simulated pathologies have a priori known causes, which allows for quantified evaluation of user's diagnostic decision; ability to simulate "challenging" exams, where proper diagnosis involves overcoming challenges, such as removal of wax, foreign bodies, confounding pathologies, oddly-shaped ear canals, squirming patients etc.

Haptic feedback can be incorporated into the virtual ear exam, such that, for example, the mobile device vibrates if the virtual ear canal was touched by the user during the exam.

Mobile devices such as smartphones are becoming a powerful tool for a variety of imaging applications. For example, optical attachments to turn a mobile phone into an otoscope, dermascope, microscope, and other optical devices for medical imaging have been described. Other attachments use the mobile device as a display and transmission system, for applications like ultrasound and spectrometry. Many of these tools were developed for medical applications, but could be used in a variety of fields, including agriculture, veterinary medicine, material examination, construction, geology and others.

The large storage capacity and integrated data transmission make mobile devices an attractive platform for image storage, but up to now the sub-clinical quality of mobile phone has made them unattractive for analysis. With new devices for diagnostic quality images, new fields of image comparison and analysis on the mobile device have arisen. A very large image database could reside on the device or a remote server, and image processing could be done either locally on the device, or images could be transmitted to a server for analysis. The methods and interfaces described here are shown on a mobile device for reference, but the same tools are useful on a desktop or other computing environment.

Images to be compared may depict two or more objects, persons, etc., or the same object at multiple times, or under different imaging or illumination conditions. Software and hardware tools like those described here enable image normalization, feature extraction, comparison, and automated analysis of both quantitative and qualitative changes. For example, automated image analysis could be used to compare a given eardrum image to a previous image from the same patient, a canonical "good example" image of a condition, or a relevant set of images or statistical values based on the features extracted.

Further, whereas digital medical devices have previously been used by specialists, the smartphone-enabled devices developed and described herein present a new paradigm of frequent data collection and analysis by at-home and other non-expert users. In standard practice a dermatologist may take a photo, with a specialized camera or dermatoscope, at a patient's appointment every six months, and use these photos to track changes over time. With the smartphone image capture devices described herein, users can now take images as often as they like and use them for automated comparison. The image frequency may depend on the condition, but for example it could be daily, weekly or monthly for a skin condition, or more frequent (every 5, 10, 15, 30 min, or 1, 2, 4, 6, 8, 12 etc. hours) for faster changing conditions like ear infection or monitoring blood vessel dynamics before/after a heart attack or stroke. Viewing and comparing images on a mobile device is a very useful feature of the apparatuses and methods described herein, both sequential images and comparing to others from the user/patient of a large database. Methods to highlight difference of change are another important feature of the methods and apparatuses described herein, and a number of exemplary embodiments are described herein.

Good images are useful for diagnosis by both human and automated readers. If the system is configured to collect video, it is valuable to provide ways to isolate frames easily. The apparatuses described herein can use features in the image/video capture software to aid in selecting good frames for review or feeding into image processing methods. Frame extraction can be manual, for example, a user can have the ability to select frames to save from a video, semi-automatic (a user can select from a collection of frames suggested by software, and frames can also be automatically saved whenever a user taps or pauses a video, which indicates that it is likely a frame of interest), or automated, e.g., good (e.g., in focus, well illuminated, interesting features, etc.) frames can be extracted using image processing methods.

The apparatuses described herein are intended for use in home, clinic and hospital environments (among others). Clinicians may include medical/nursing students and experienced professionals. User roles are implemented in software to assure appropriate interfaces and functionality for 'Pro' and 'Home' users. Images/data are tagged with the type of user who collected them, which can be used in deciding what to include in the method training.

Normalization/Registration

Many of these tools benefit from calibration and normalization to aid in comparison. Mobile devices such as the iPhone commonly include sensors such as a gyroscope, accelerometer, ambient light sensor, proximity sensor, noise-cancelling microphone, and others, which could be used to aid in image analysis and comparison. For example, the internal gyroscope and accelerometer readings may be used as image metadata to aid in orientation normalization and image registration.

External sensors and hardware features are also useful for image analysis. For example, a dermascope smartphone attachment may use an integrated test pattern, which can be used by the apparatuses to normalize the white balance, color values, and image exposure. Uniformity of exposure (or fidelity of the exposure pattern to an illumination design) can also be captured in an image or added using an additional sensor. For example, an external light meter could be couple with the mobile device using wired or wireless means, or a secondary camera on the device could capture the relevant lighting data. The mobile app could also measure the brightness of the region of interest and manually adjust the LED intensity to compensate (with a fixed exposure time). This is useful because many phones (including the iPhone 5) do not provide manual control over the exposure settings of the camera.

User supplied data, such as left or right ear, and landmark features, such as the eardrum light reflex, can also be used independently or in any combination with sensor-derived data to determine or normalize image orientation.

Methods and apparatuses configured to allow easy comparison between images are also described. For example, the following are methods and interfaces for apparatuses for comparing two images ("Image A" and "Image B"). Image A and Image B might be images of the same or different object, patient, etc. Image B could also be an overlay showing specific features or other information about Image A.

Figure 39:
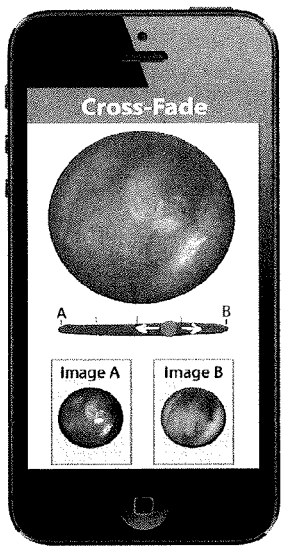
FIG. 39 is an example of a display comparing an image of a patient's tympanic membrane with a library (reference) matched image by cross-fading the two images.
Figures 48E, 48F:
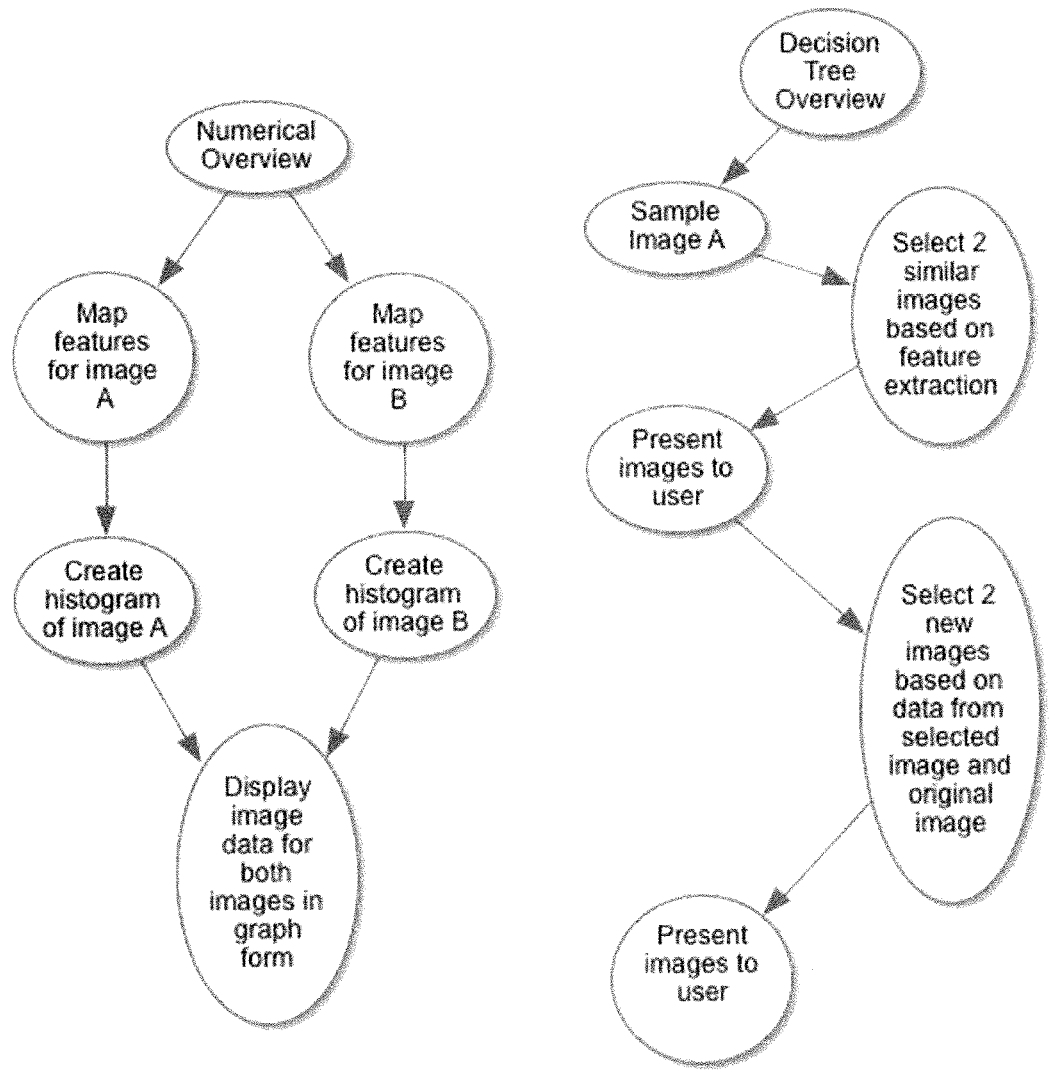
FIG. 48E is a schematic of a method of comparing tympanic membrane images including histograms of numerically described features. An example of this type of display is shown in FIG. 47.
FIG. 48F is a schematic of a method of comparing tympanic membrane images.

The image comparison may provide animation. For example, morphing. The user may be able to control and view a visual transition of Image A into Image B. The orientation of the images could be registered using information from the camera's internal gyroscope or based on features detected in the images. The transition could be based on complex algorithms or a simple crossfade. See FIG. 39 and FIG. 48A.

Time Lapse may be used. Images may be presented chronologically, gradually progressing from the first image to the last image in a "stop-motion" or "time-lapse" animation. This would work for any number of images in chronological order.

Figure 40:
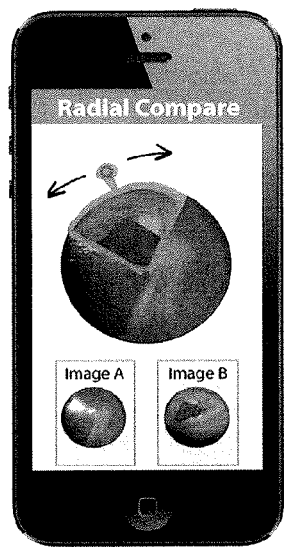
FIG. 40 is an example of a display comparing an image of a patient's tympanic membrane with a library (reference) matched image by radial comparison between the two images.
Figure 41:
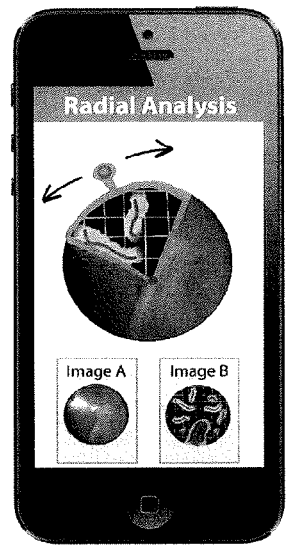
FIG. 41 is an example of a display comparing an image of a patient's tympanic membrane with a library (reference) matched image by radial analysis between the two images.

Images may be superimposed for comparison. For example, the apparatus may include a radial slider—an interface that presents Image A to the user with a movable "pizza slice" control anchored in the center of the image. In the area of the "slice" Image B would be superimposed over Image A. As the user rotates the "slice" around Image A, different areas of Image B would become visible. See FIGS. 40-41. FIG. 48B describes schematically a method of generating this type of display. This is especially useful for circular images like found in otoscopy, but the same slider approach could also be used as a linear transition, as the user swipes from side to side (similar to FIG. 43).

Figure 42:
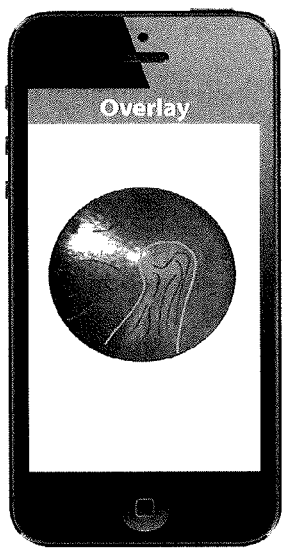
FIG. 42 is an example of a display comparing an image of a patient's tympanic membrane with a library (reference) matched image by overlaying the two images.

Ghost—The display would show Image B superimposed over Image A. See FIG. 42. If the user can control the relative opacities of Image A and Image B, this is similar to "Morph" described above (see FIG. 39).

The ghost technique is also useful in image capture. For example, when imaging a patient's ear drum (or skin, eye, etc.), the user could be presented with a semi-transparent ghost image to aid in alignment. The ghost image could be a previous image from that spot, or a canonical example.

Automatic Feature Annotation—An image would be displayed with salient features automatically labeled. For example, an otoscopy image of the ear drum could be processed (in real-time or post-capture) to extract and display key features such as the light reflex, malleus, and umbo.

Any of the apparatuses and methods may be configured to provide side by side comparison. For example, posterize color change shows a "posterized" version of Image A displayed alongside a "posterized" version of Image B. Posterization shows averaged image color over large areas of an image. See FIG. 43.

Isolate Channel—Image A would be presented alongside Image B. Image B would be a copy of Image A isolating a particular color channel, possibly selected by the user. See FIG. 44.

Color Gradient—Image A and Image B would be displayed above a gradient showing the average color of each image. See FIG. 45.

Figure 43:
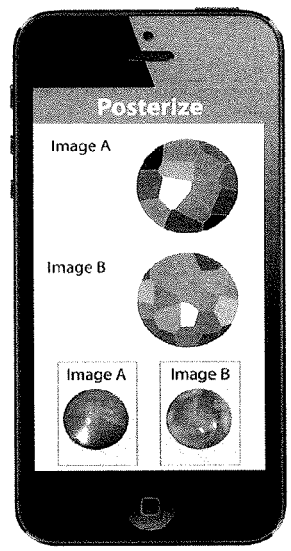
FIG. 43 is an example of a display comparing an image of a patient's tympanic membrane with a library (reference) matched image by posterizing the two images.
Figure 44:
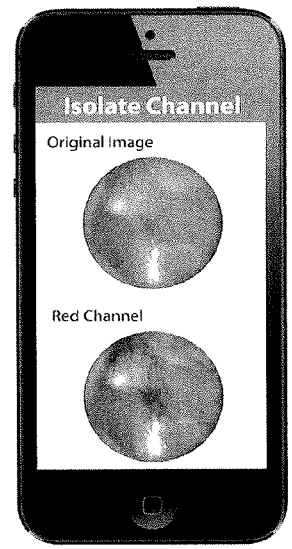
FIG. 44 is an example of a display of an image of a patient's tympanic membrane by showing one or more isolated color channels (a red color channel is shown).
Figure 45:
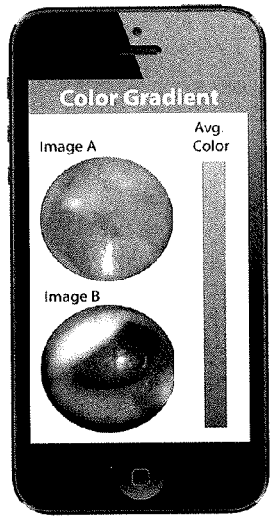
FIG. 45 is an example of a display comparing an image of a patient's tympanic membrane with a library (reference) matched image by comparing color gradients.

The schematic shown in FIG. 48C illustrates one exemplary method of forming displays such as those shown in the examples of FIGS. 43-45.

Any of the apparatuses and methods described herein may be configured to provide a numerical display for analysis of an image (or for comparison to one or more other images).

Figure 46:
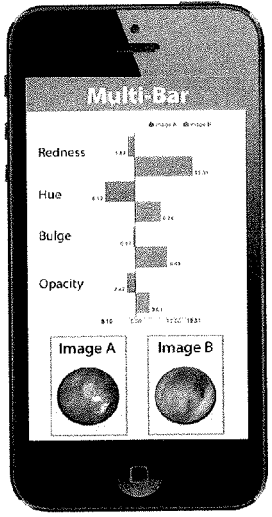
FIG. 46 is an example of a display comparing an image of a patient's tympanic membrane with a library (reference) matched image by showing multiple bar graphs of different feature (redness, hue, bulge and opacity) comparing the two.

Multi Bar—A multi-bar graph can be displayed showing data for Image A and Image B for various different measurements, e.g., redness, translucence, concavity. See FIG. 46. One variation of a method of forming such a multi-bar display is shown schematically in FIG. 48D.

Distribution Model—A histogram of key data (such as color values in a region of interest) could be presented. Automated or manual comparison of the color distribution could aid in image analysis. For example, if a user is presented with two images of an ear drum for which the spectral distribution has shifted 10% toward red, it may be suggestive of inflammation and infection.

Semantic displays may also be used. Plain English Description—An image would be presented with an automatically generated "plain-English" description. This could highlight salient features, like the bones of the middle ear, or it could provide a simple and understandable analysis to a non-expert viewer (e.g., "ear infection detected", or "90% match with ear infection".

Custom Language—An image would be presented with an automatically generated description of the image employing terminology defined by CellScope to classify images. This could be a "redness score" or "wrinkle score" generated using custom methods.

Other types of display/presentations may be alternatively or additionally used.

Decision Tree—Allows the user to compare an image against a library of pre-diagnosed images. They make a selection, then are presented with an additional list based on their previous choice similar to the subjective portion of an eye exam.

Amalgam—Displays a composite image containing average values for a set of source images.

Figure 47:
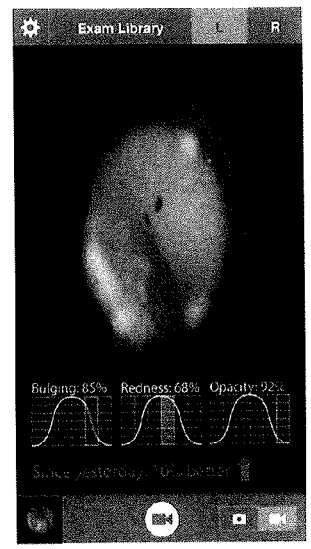
FIG. 47 is an example of a display showing the progression of features from images of a patient's tympanic membrane over time, and graphs of features (bulging, redness, opacity).

This list is meant to illustrate a few of the possible implementations of the methods and apparatuses described herein for analysis and image comparison of images from a mobile device. While the examples shown focus on medical applications such as ear, skin, and eye diagnosis, this is not meant to be limiting or exhaustive. FIG. 47 shows an example application interface which could be used to provide analysis data to the user. In this case, the image is a comparison between an initial doctor's office visit and a follow-up for a patient with suspected ear infection. The salient features (e.g. redness, bulging, and translucency) may extracted from both images by the apparatus and used to provide a visual indicator of the patient's progress directly in the mobile app. Similar analysis and advice could be provided on a web or desktop computer interface, based on images from the mobile device. As mentioned above, FIGS. 48D and 48F illustrate methods that may be used in forming a display such as the one shown in FIG. 47. This variation could be used for telemedicine, or fully-automated diagnosis, providing new models for healthcare delivery. FIGS. 48A-48F also illustrate examples of methods for analyzing and displaying images that may be used and may be incorporated as a feature or portion of an apparatus.

In addition to the components of the apparatuses described above (e.g., lens, speculum, processor, display, etc.), any of the apparatuses described herein may also include one or more additional elements. For example, these otoscope device may include an insufflator with built-in pressure sensor to automatically a tympanic membrane mobility.

The American Academy of Pediatrics currently recommends that "clinicians should not diagnose AOM in children who do not have Middle Ear Effusion (MEE) (based on pneumatic otoscopy and/or tympanometry)". Under pneumatic otoscopy, MEE is indicated by impaired TM mobility. This process consists of viewing the TM while applying both positive and negative pressure within the ear canal using an insufflator attached to a pneumatic otoscope, which creates an airtight seal between the ear canal and the pressure source. In a patient without MEE, the TM should visibly move upon application of pressure, and in a patient with MEE, the TM may remain stationary.

Two problems with traditional pneumatic otoscopy are that (a) there is significant inter-operator variation, particularly with respect to the level of applied pressure and (b) the process is subjective and prone to inter-observer variability. These problems may be addressed with an automated system that both measures the applied pressure and objectively assesses movement of the TM.

To measure the applied pressure, an integrated pressure sensor within the pressurized area of the pneumatic otoscope would record the pressure reading and communicate it to a central processing unit and memory storage device, such as a mobile phone. This pressure sensor would be able to detect and record when the user performed a manual insufflation and the magnitude of the pressure generated.

As the user points the otoscope at the TM and performs manual insufflation a computer vision system can automatically assess the movement of the TM while pressure is simultaneously recorded. After detecting the TM, e.g., via the TM segmentation method described above, movement could be automatically assessed in several ways:

Via optical flow, in which the movement in pixels of different parts of the TM and surrounding ear canal are assessed with respect to each other. In this case, significant movement in, for example, the superior posterior quadrant with respect to the surrounding area would suggest high TM mobility.

Via a traditional machine learning method that is trained using labeled data consisting of otoscopic videos undergoing insufflation. The labels would be comprised of levels of mobility, as assessed, for example, by expert readers such as experienced clinicians. Either traditional feature-based learning (e.g., based on the change of different features from frame to frame) or deep learning, as detailed above, could be used.

The pressure level and degree of mobility could be simultaneously assessed, and measurements of mobility would be deemed "clinically meaningful" only if the recorded pressure was within some clinically determined range that had been demonstrated to induce observable TM mobility on patients without MEE and no observable TM mobility on patients with MEE.

To increase the consistency of results obtained with the method of automatic assessment of insufflation results, a small electronically controlled pneumatic pump can be integrated into the otoscope module to perform controlled insufflation. This pump would use feedback control with the pressure sensor to apply either predetermined or user adjustable positive and/or negative pressure levels to the TM, during which TM mobility could then be assessed using the techniques discussed above. Controlling the pressure in this manner would likely improve both the repeatability of the results (since the applied pressure would not be subject to variation in the squeeze force generated by the operator) and the user experience, since it would avoid the case where users may be required to perform insufflation multiple times until the recorded pressure level is within the preferred range.

Figure 49A:
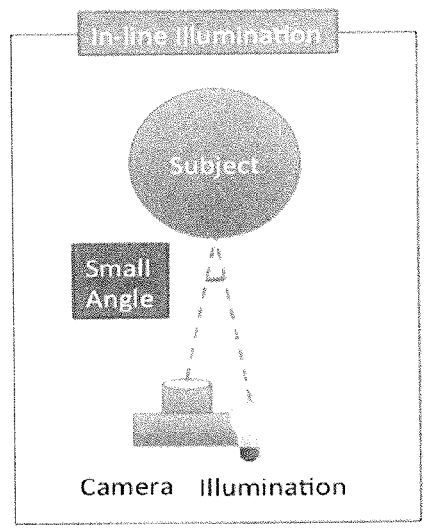
FIG. 49A schematically illustrates one example of in-line illumination.
Figure 49B:
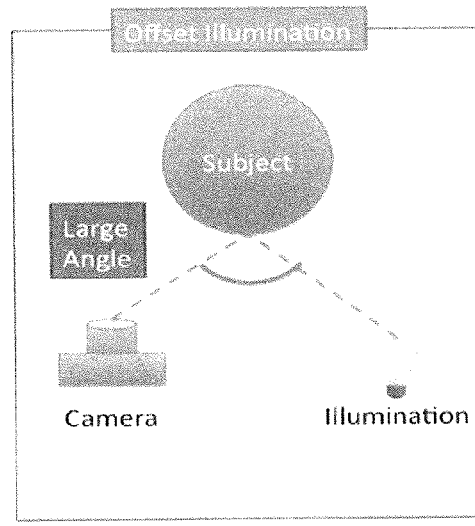
FIG. 49B schematically illustrates one example of offset illumination.

Offset Illumination and Optics for the Purpose of Obtaining Enhanced Image Contrast Traditional otoscopes co-locate the camera optics and the illumination optics along the same axis, resulting in a system with "in-line illumination" (FIG. 49A). In the case of in-line illumination, texture, such as bumps or ridges, cannot readily be seen because no visible shadows are cast; anything visible by the camera is also visible by the illumination source, which precludes observation of shadows (e.g., FIG. 49C). However a system with "offset" or oblique illumination (FIG. 49B), where a significant angle exists between the camera-subject line and the illumination-subject line, will allow shadows to be seen by the camera, therefore highlighting the physical texture of the subject (e.g., FIG. 49D). FIGS. 49C and 49D show photos of stucco wall with flash in line with camera (49A) and with flash-subject line at a significant angle to camera-subject line (49D).

Although the confined cavity of the ear canal or other bodily cavities may not permit a large offset between the optical components and the illumination, one could create a system that offsets the illumination as much as possible, as in FIG. 50B. This moderate offset would add some enhanced degree of texture visualization via the visualization of shadows. Such a system might require a custom or reusable speculum that would allow the camera optics and illumination optics to be as close to the tip of the speculum as possible, to maximize the relative angles between the collection/emission surfaces of the camera and illumination optics and the subject.

Figures 51A, 51B:
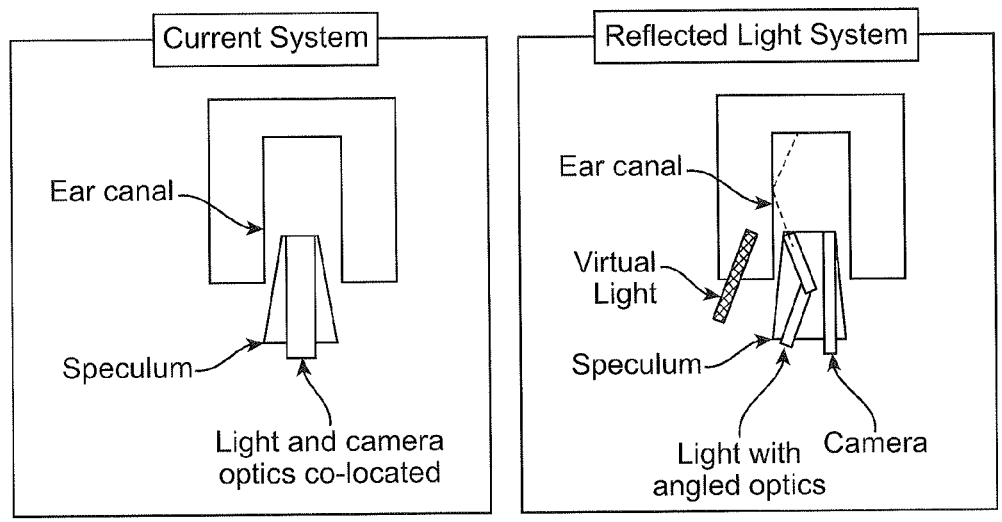
FIG. 51A (like 50A) is an example of an otoscope having co-located (e.g., in-line) lights and camera optics.
FIG. 51B is an example of a system using reflected-light (angled optics).

As an alternative to having a direct illumination source that is separated from the camera optics, as in FIG. 50B, it would also be possible to use an indirect light source wherein the light is reflected off the ear canal before reaching the subject; this scenario is shown in FIG. 51B. In FIG. 51B, the illumination optics and the camera optics are again offset, but they need not be. A difference between FIG. 50B and FIG. 51B is that, in FIG. 51B, the illumination source is directed not at the subject but at the canal wall, where one or more reflections occur before the light reaches the subject. The major advantage of the reflected light setup in FIG. 51B is that the resulting visual effect is the same as if the illumination source was located significantly further from the camera optics than it actually is, as indicated by the "virtual light" in FIG. 51B.

Disadvantages of a reflected light setup may include: some light will be absorbed and not reflected in the reflection process; how much light is lost to absorption depends on the material properties of the canal wall, including moisture, presence of cerumen or other materials, etc.; the reflected light will take on some of the coloration of the canal wall; and/or the reflected light may be occluded by objects which would not occlude the light if it were collinear with the camera optics.

However, these disadvantages can be easily overcome via the following techniques: ensure that the incident light amplitude is sufficiently high that enough light reaches the subject after reflection; correct the color of the subject in post-processing using white balance techniques; and/or allow rotation of the otoscope around the axis of the ear canal by the operator to avoid any occluding objects.

Multiple Optical Elements for 3-Dimensional Imaging

Figure 52:
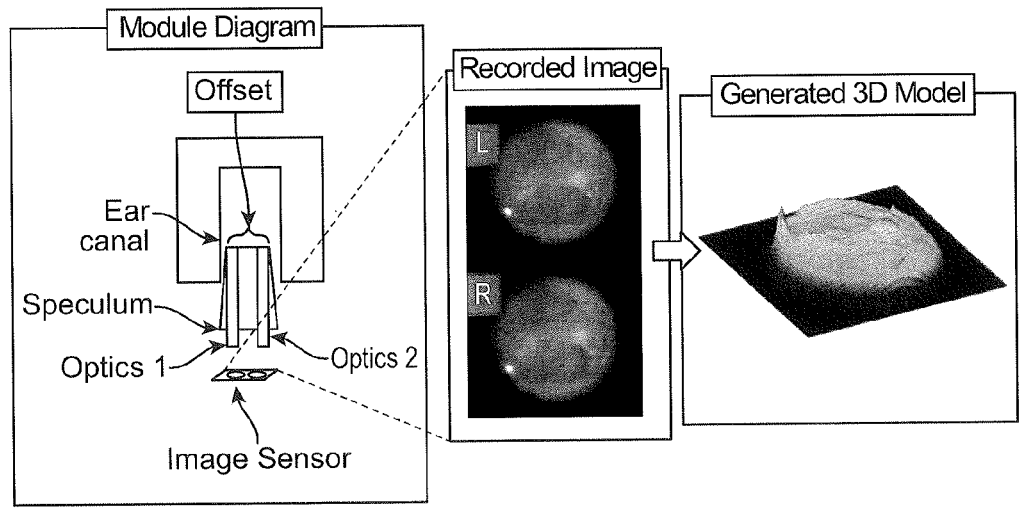
FIG. 52 is an illustrate of the generation of stereoscopic 3D otoscope images.

Stereoscopic imaging may be used to enable recording of 3D videos and images within visible light imaging, e.g., otoscopic exams. In this case, two separate optical paths would exist, the collecting areas of which would be somewhat offset (FIG. 52, left). The offset in collection areas would allow for stereoscopic vision, as each optical path would see a slightly offset image with respect to the other. The two optical paths could mate with a single, common image sensor, which would reduce the complexity of the electronics hardware. Since both images would be recorded simultaneously in the same video stream (FIG. 52, right), software could be written to locate both recorded images in the common video stream and combine them into a single 3D image or video. That software could also make the individual monocular streams available for viewing, e.g., if the user does not possess a system with which to view the 3D reconstruction.

Once the 3D video or image is created, the recording can either be displayed non-interactively in 3D or the depth and texture data can be separately analyzed to create a 3D model, as described in herein.

Automatic White Balance Calibrator

Figure 53:
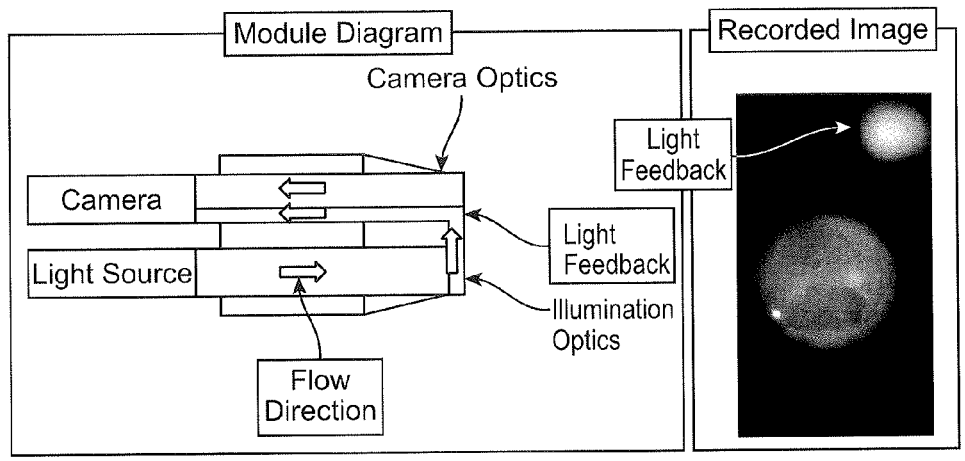
FIG. 53 illustrates light feedback for white balance calibration in an image.

In certain situations during an otoscopic or similar visible light medical imaging exam, it may be challenging to determine the color temperature of the incident light, which may prevent proper white balance of the recorded image or video. If the illumination source and imaging system are integrated together, it may be possible to feed a small amount of the illumination source directly into the camera system. In that case, software could be used to measure the temperature of that sample light source, which would always appear in the same region of the recorded image, and adjust white balance accordingly. An example otoscopic module diagram and resulting recorded image is shown in FIG. 53.

Any of the apparatuses described herein may also include additional components. For example, any of these apparatuses may include an integrated gas analyzer. There are currently many types of equipment available for performing diagnostics via imaging including but not limited to otoscopes, dermascopes, retinascopes and endoscopes. These devices are used by the operator to determine among other things, if a patient is experiencing an infection. By integrating a gas analyzer into these systems additional data about the area of interest can be obtained and the diagnostic capability of the device can be enhanced.

Figure 54:
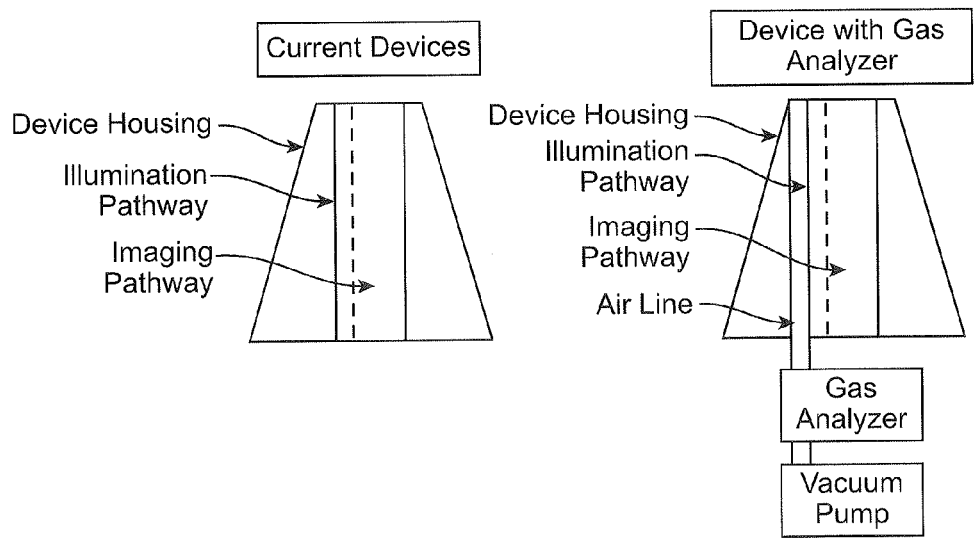
FIG. 54 is a comparison of an otoscope device without (left) and with (right) an integrated gas analyzer.

The gas analyzer can be integrated by the addition of an air line that has an inlet near the opening of the imaging and illumination pathways. This air line is then connected to a vacuum pump to allow samples of the air in the region of interest to be collected and taken into a gas analyzer for analysis as shown in FIG. 54 (comparing devices with and without an integrated gas analyzer).

The gas can be analyzed via multiple methods including but not limited to gas chromatography and mass spectrometry. As technology continues to advance, the size of these analyzers continues to decrease and they may exist as either standalone units or integrated into the handheld device itself.

The analyzer would then examine the contents of the gas sample obtained from the region of interest and record it for further analysis. These results could be compared to known gas emissions of infectious diseases to allow the operator to confirm if any known diseases were present. One example of this is shown below in FIG. 55 where the spectra of emissions from a known infections agent are compared to the measured spectra of a gas sample and the infectious agent is identified.

Any of these apparatuses may also include multispectrum sensing of a target area via optical switching. In many cases it is useful to get information about an area of interest using multiple spectrums of light, such as infrared, ultraviolet and visible light. However, doing this involves either using sensing elements which sacrifice precision in one spectrum in order to support a wider variety of spectral inputs or having multiple sensors aligned parallel to each other which offsets what each sensor is seeing as they do not all share the same axis. In many cases where space is constrained, such as with an endoscope or otoscope, having multiple sensors aligned in parallel with each other is not practical.

In order to overcome these space limitations and to allow for sensing of the same target area across multiple wavelengths an optical switch can be used to redirect the light coming in from a single target source to multiple sensors. This allows for an identical region to be sampled by each sensor and removes the need for multiple parallel pathways of light at the inspection end of the device where space is typically the most constrained.

Figure 55:
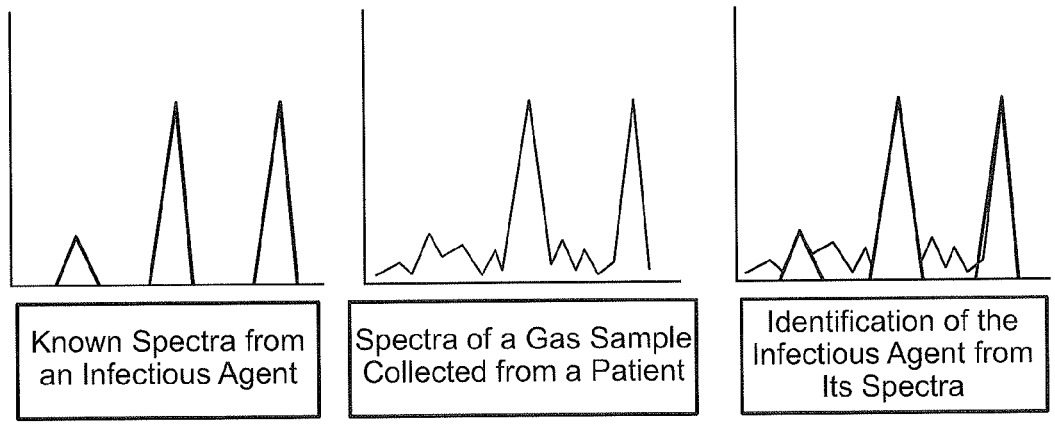
FIG. 55 illustrates identification of an infection agent using mass spectroscopy of a gas sample.
Figure 56:
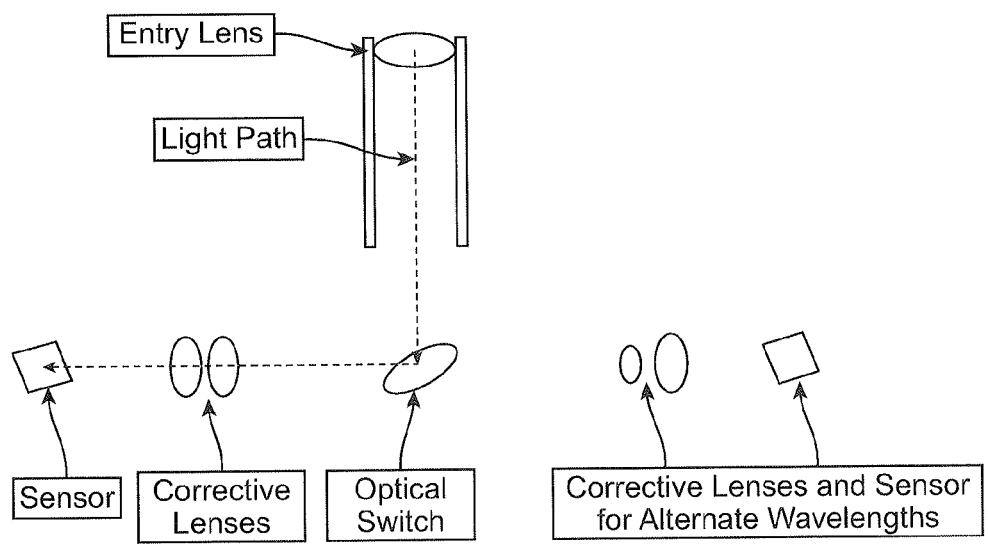
FIG. 56 is a schematic illustration of multi-spectrum imaging from a single source via an optical switch.
Figure 57:
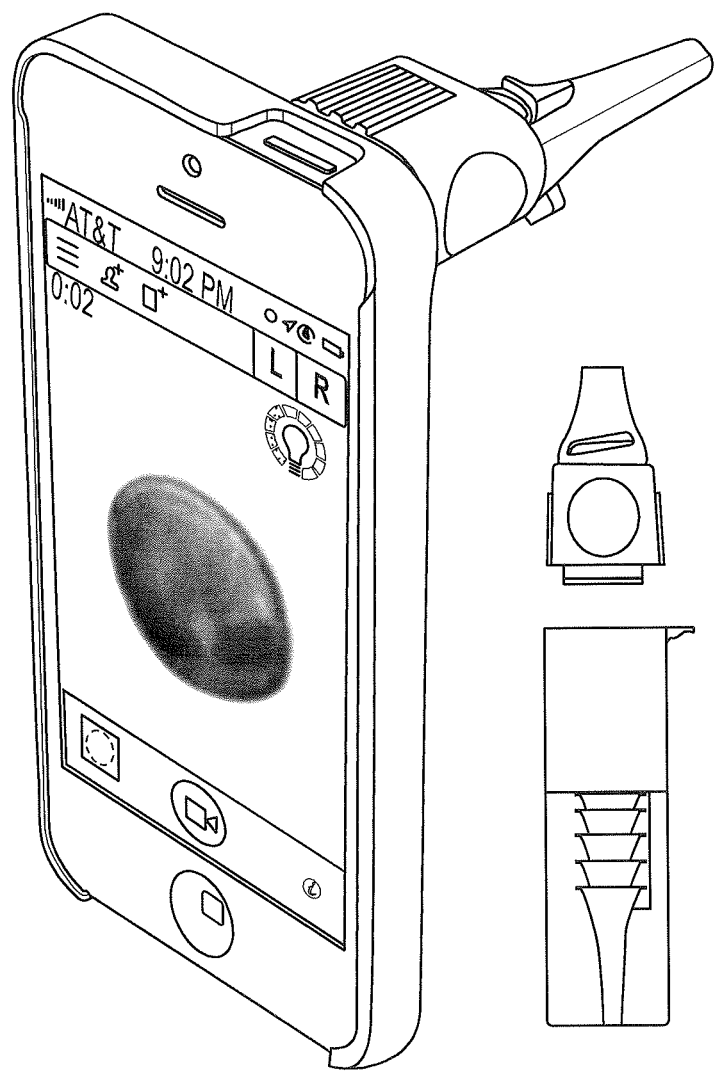
FIG. 57 illustrates an example of an otoscope and imaging apparatus in which the otoscope is modular is adapted to connect to a smartphone (e.g., iPhone). The phone may include a processor adapted to perform any of the methods described herein either on/by the phone, or by connection to a remote processor (e.g., cloud).

In one example, as shown in FIG. 55, light comes in to the device from a single point of entry and is directed into the first sensor through a set of corrective lenses. These corrective lenses can be used to correct for any effects that are particular to the wavelength being sensed or they could be used for magnification or focusing purposes as well. Once the target area has been imaged with sensor 1, the optical switch will flip to direct light into sensor 2 which has its own set of corrective lenses as well as a different sensor. FIG. 56 illustrates one variation of a layout of Multi-Spectrum Imaging from a Single Source Via an Optical Switch Any of the apparatuses described herein may be configured to be interchangeable (e.g., with interchangeable imaging modules). For example, any of these imaging systems can have a number of embodiments to fit different imaging applications. FIG. 57 shows a passive attachment, which uses its lenses to combine with the smartphone camera lens to form an image, plus fiber optics (or other light guide or wave guide) to draw light from the phone's LED flash. While one embodiment of the optical attachment is passive, it can also be useful to have powered electronics built into the device (for illumination, image sensor, IR sensor, or other sensors or actuators). The power could be drawn from the device, or reside in the attached module. For example, optics in the attachment could work with the phone's camera to form an image, and the attachment could also contain a battery and LED light for illumination of the sample, plus additional optical components to customize the pattern, spectrum, polarization, or other properties of the light.

The device in FIG. 57 uses an attachment with lenses that work with the phone's camera to form an image, and fiber optics or other light guide design to draw light from the camera's LED flash. Thus this version of the device can be passive, relying on the phone for power.

Figure 58:
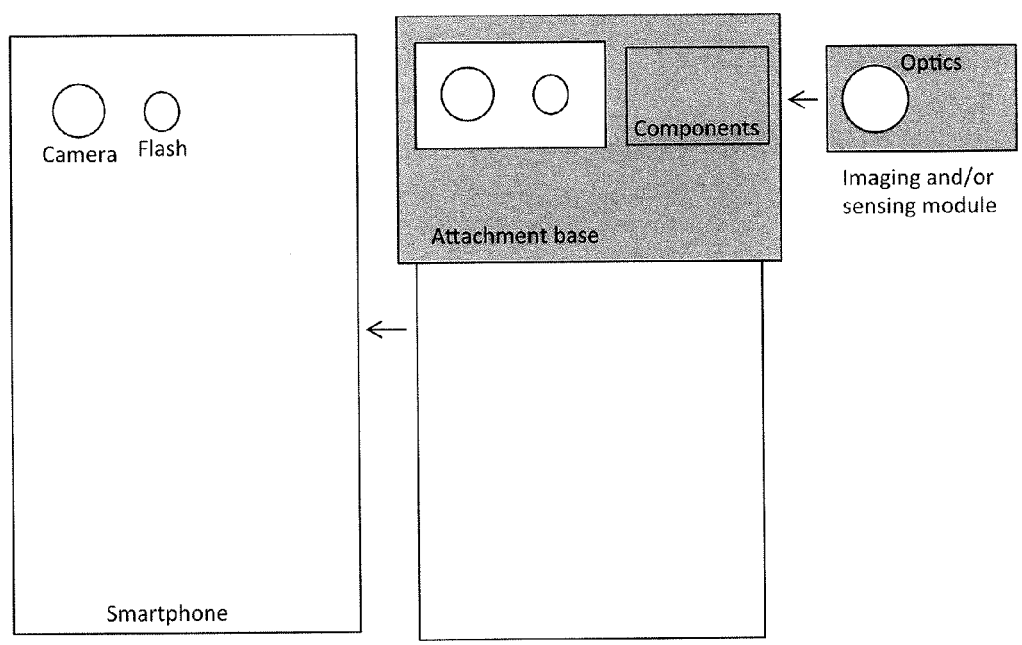
FIG. 58 is an example of a "smart case" for use with a smartphone to hold/connect to a lens (such as an otoscope, etc.).
Figure 60:
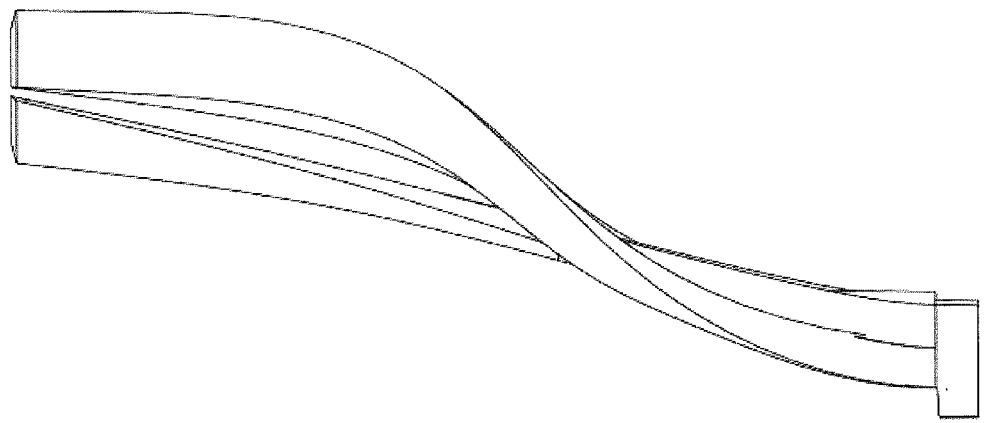
FIG. 60 is a side profile view of the lightpipe of FIG. 59.
Figure 59:
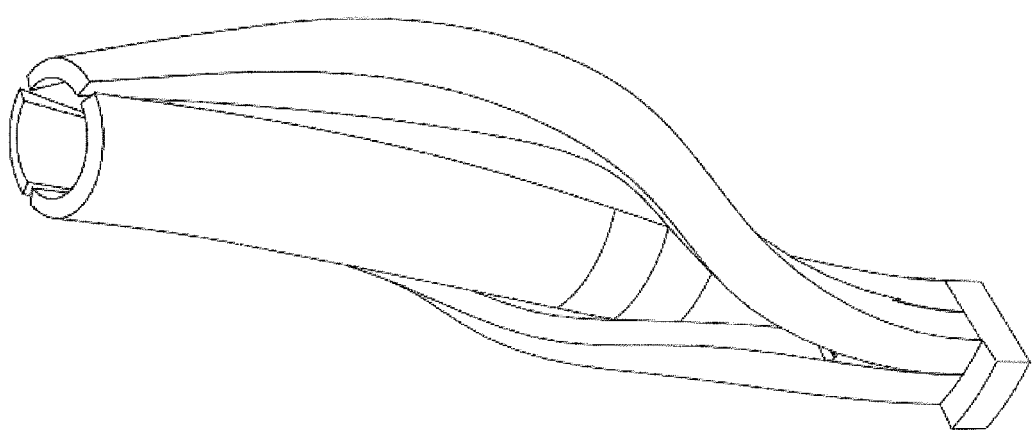
FIG. 59 is shows one example of a lightpipe for any of the apparatuses described herein, including an otoscope component, for communicating light from a light source (e.g., LED on the surface of a smartphone) to a light right at the distal end to illuminate a portion of the body to be visualized.
Figure 62:
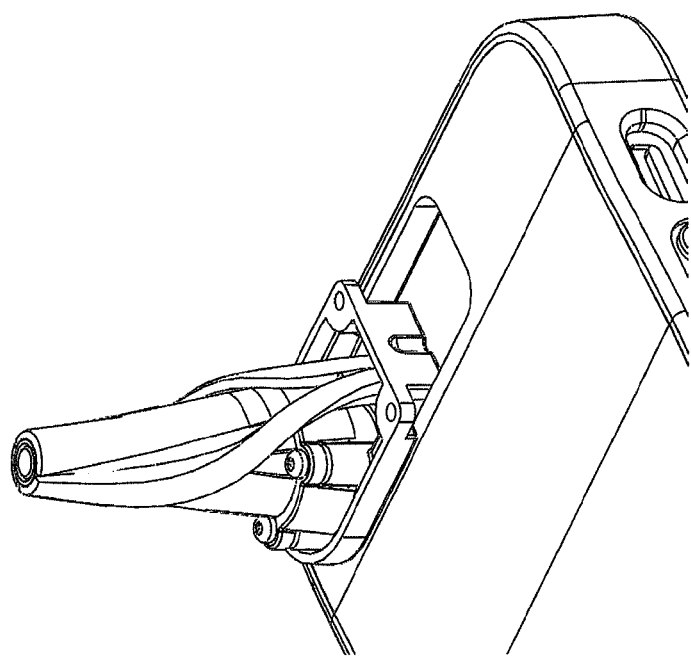
FIG. 62 is a view of a portion of an otoscope system including a lightpipe such as the one shown in FIG. 59 integrated into the otoscope attachment component and attached (optically coupled) to a smartphone LED via a mount. In this example, the mount is a portion of the case for the smartphone which has an opening onto which the otoscope attachment couples.
Figure 61:
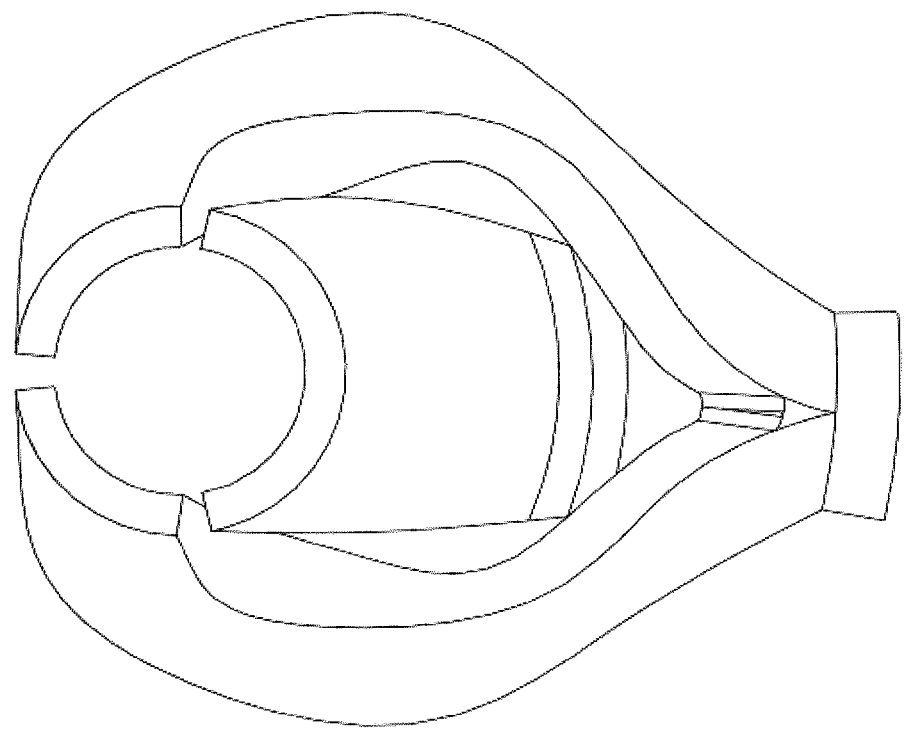
FIG. 61 is a top view of the lightpipe of FIG. 59, showing a ring light configuration at the distal end. Light is transmitted up the light pipe to illuminate the distal ring region.
Figure 64:
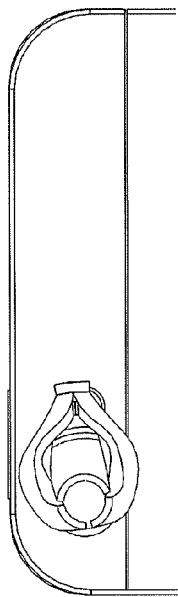
FIG. 64 is a top view of FIG. 63, sowing the lightpipe directing light from the smartphone LED into a ring light around the smartphone camera axis.
Figure 63:
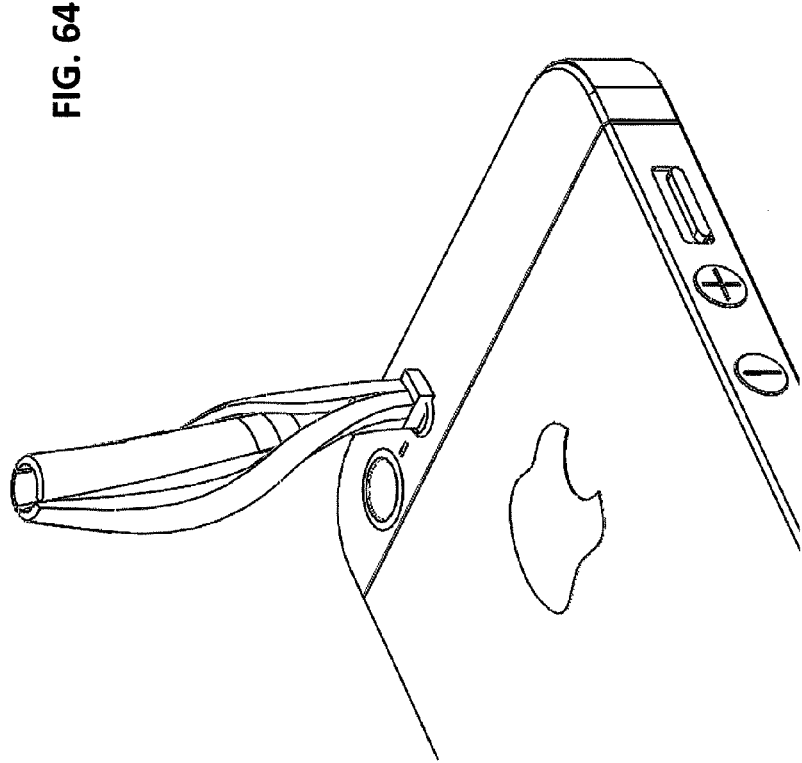
FIG. 63 is an example similar to FIG. 62, but with all of the otoscope components, with the exception of the lightpipe removed/made invisible, showing the interaction between the lightpipe and the phone. Light is coupled into the lightpipe from the phone LED and guided up to a ring light around the distal end of the phone.

FIG. 58 shows a different configuration of an apparatus as described herein, where electronic components can be included in the smartphone attachment. In one modular configuration, the smartphone case (or half-case or other attachment interface) contains a battery, image sensor, and light source, and an interface onto which imaging modules can be attached (the "smart case"). These modules could be passive, working with the components of the smart case and the phone to collect data. For example, the smart case (attachment interface) could have a battery and an LED, and different modules could be used to tailor the imaging to ear, nose, throat, skin, eye, endoscopic or other imaging (in addition to non-medical imaging). This approach could allow for a more powerful case to work with a variety of simpler, less expensive optical or other sensor attachments, providing a versatile toolkit for mobile image and other data collection.

In FIG. 58, the smartphone (left) commonly contains a camera and lightsource (LED flash). A "smart case" (center) may have a battery or draw power from the phone with a wire, and in turn power components in the case or other modular attachments. Components here could include a light source, or other shared sensors which could be useful. As shown, optical attachments with different imaging properties can be attached to the smart case, designed to work with the smartphone's own camera to form an image on the camera's sensor. The case could also have an LED or other light source, and a light guide in the modular attachment could shape or configure the light as necessary for the imaging application (e.g., structured illumination or polarized illumination). Another configuration is for the smart case to also include an image sensor, but use interchangeable optical modules to tailor the image collection to the application.

Also described herein are device tips with special properties. Earwax is a mixture of desquamated keratinocytes and hair combined with the secretions of both the ceruminous and the sebaceous glands of the external ear canal. The major organic components of earwax identified were long chain fatty acids, both saturated and unsaturated, alcohols, squalene and cholesterol With this organic composition in mind, an otoscope specula may include oleophilic, hydrophobic or other material properties to attract cerumen. The material may be a coating, partial coating (e.g., ring) on the speculum. Standard specula are designed simply to be inert and facilitate image collection in the ear canal. A specula that uses materials which attract oily substances may help move or remove wax to improve image collection.

Another approach to improved wax capture could include an intermediate "tag", such as a magnetic particle which has affinity for the organic wax. This tag could be applied via drops in the ear canal, or squirted in through a modified speculum. A magnet otoscope speculum could then be used to withdraw the tagged wax from the ear canal. This approach is not limited to magnetic attraction, but could be broadly applied to any chemical or physical attractive force coupled with a "wax tagging" substance.

Any of the apparatuses and methods described herein may be systems and methods for diagnostic imaging. These systems and methods for image or video capture and analysis may be adapted for use with a mobile device. The examples described herein may be mainly used with a mobile phone (e.g., smartphone), with an attachable imaging lens (attachment) as described above, but they could also take the form of an integrated, stand-alone device. A system may include multiple attachments (components) forming a modular system, or the like. In general, the apparatuses and methods described herein may address the challenges of imaging with a mobile device, including illumination, calibration, and normalization of the data collected, as well as practical issues such as ease of manufacturing. In addition to the examples of otoscopes and a dermascopes described herein, other imaging applications may be included, such as an endoscope, laryngoscope, ophthalmoscope, general microscope, as well as multi-function or modular devices which can serve several imaging and/or other data collection purposes.

Some variations of the otoscope are indirectly illuminated otoscopes that utilize fiber optics to direct the light from a light source (typically located in the handle near the battery) to form a ring light around the viewing area of the otoscope in order to illuminate the ear canal. Additionally, otoscopes can be lit via direct illumination by utilizing a light bulb placed within the viewing area itself. As described above, the use of indirect illumination with fiber optics allows for an unobscured viewing area as well as greater freedom in the placement of the illumination components and an additional factor of safety as all electrical contacts are isolated away from the patient's ear canal.

The use of fiber optics has several limitations however. The fibers must be polished in order to transmit light through a time consuming process that can introduce variability in the light output as the sanding pads on the polishing equipment wear with each use. The fibers are also limited by the circular profile of the fiber optics themselves. The path of the fibers is also limited by the material properties of the fiber optics, which reduce their efficiency if they are bent too tightly. Described herein are lightpipes (also known as a light guides, wave guides or other similar terms) which is used to guide the light from a source away from the viewing area (in one case a phone, in another case an LED on a circuit board) to a ring light around the viewing area of an otoscope. This lightpipe may be an injection molded part which is much simpler, cheaper and more consistent than a polished fiber optic bundle. Additionally, the greater freedom allowed in shaping the lightpipe may allow for it to be made to fit into more compact otoscopes while retaining good light output performance necessary for viewing the ear canal. An example of an otoscope including a lightpipe is shown in FIGS. 59-65C.

The lightpipe can help overcome some challenges with handset compatibility of an imaging attachment. For example, the collection side of the lightpipe can be designed to funnel in the light from several possible source positions, which can make it possible for a single lightpipe design to work with multiple handsets. This utility is apparent, for example, when operating with different phone types, such as the iPhone 5 and 5S, which have a consistent overall form factor, but vary in the design and position of the camera's LED flash. A lightpipe can have a collection feature which covers both of these LED sources, and then re-directs the light according to the application (ring light in an otoscope, structured or diffuse illumination in a dermascope, etc.).

Figure 66:
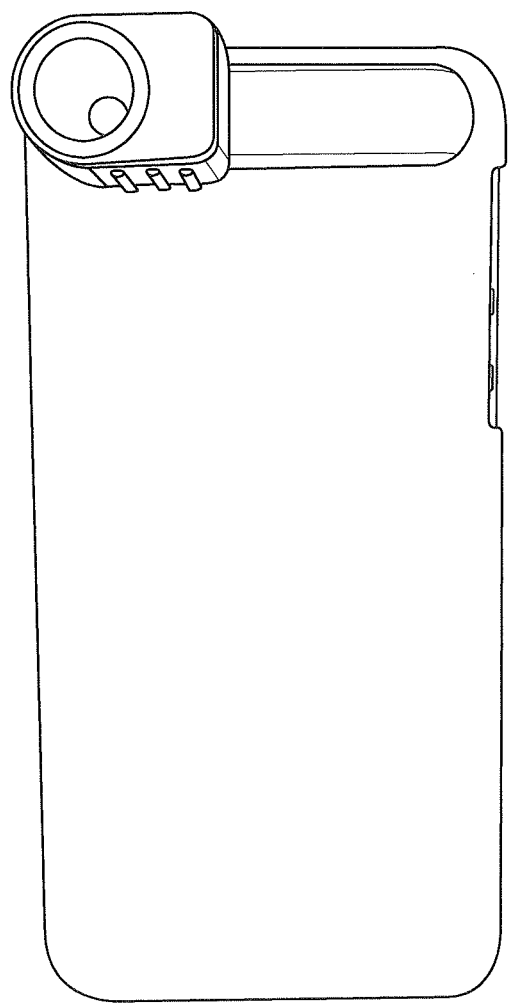
FIG. 66 shows a dermascope attachment for a mobile phone, forming an apparatus. The attachment uses a lens for magnified imaging (increased compared to the native camera magnification or resolution), a light guide to direct light from the phone's LED, two polarizers in crossed configuration to reduce glare, and an enclosure designed to reduce ambient light and provide optimal imaging distance when in contact with the skin surface.

Precise alignment with the light source can also help optimize the performance of lightpipe. As shown in FIG. 66, a phone case designed for attachment of accessory components can help ensure precise alignment with the handset's features, enabling a single lightpipe design to be positioned to work with multiple LED positions.

A lightpipe can also be an intermediate light collection feature, which takes in light from the handset, circuit board, or other illumination source, and transfers it on to another application-specific illumination module.

In addition, any of the lightpipes herein may have a constant cross section throughout each element (or each "pipe"). In some applications of the lightpipe, it may be helpful to maintain a constant (or nearly constant) cross-sectional area along the segments of the light pipe in order to maximize transmission efficiency.

Any of these lightpipes may also have a high polish on the lightpipe surface. For example, SPI-A2 polish (1 level under lens polishing) on all surfaces and SPI-A1 (lens quality) wherever practical to reach with polishing bit. A lightpipe may also have a smooth path on each pipe and minimized curvature to maximize internal reflection. A lightpipe may also use LED/lightpipe grade plastic with high transmission factor and clarity (e.g. Makrolon LED 2045), and/or may include an angled outlet surface (e.g. 15 degrees) to redirect output rays forward. This can significantly help control the targeting of the illumination (FIGS. 65B and 65C).

As shown in FIG. 65A, bumps 6503 or other features on the housing 6501 may help position the lightpipe while also decoupling the lightpipe from the inner housing to prevent absorption of light by the housing.

Also described herein are mobile handset attachments for diagnostic imaging. FIG. 66 shows an embodiment of an apparatus as described herein, configured as a dermascope (also called a dermatoscope) for skin imaging. In this embodiment, it includes a mobile phone case to which the optical module, or dermascope component, attaches (e.g. clips on, slides in, or any other attachment component). The module (dermascope component) contains a magnifying lens which is selected and positioned to work with the phone's camera lenses to form an image on the phone's image sensor. Configuring the attachment lens or lenses properly to work with the phone's camera lens may be important for high quality imaging.

The magnification level may be chosen according to the desired application, and may include a tunable lens or lens system which enables dynamic configuration of the magnification or focus. This could be a deformable lens, or could be one or more lenses whose position can be adjusted to alter the magnification, focal length, or other properties. This system can provide high resolution images, on the order of micron resolution, depending on the lens configuration. One embodiment of the system for high resolution imaging includes a distal objective lens, and a proximal eyepiece lens together configured to work with the phone's camera lens or lenses.

FIG. 66 shows an enclosure for the optical system which is meant to facilitate image capture; the skin surface is in focus when the enclosure is in contact. In some cases, partial or no contact would be preferred (e.g. a wound healing monitoring application). In that case, the optical system can be designed to accommodate a gap between the enclosure and the surface, or a protective layer through which the surface is viewed. If a protective layer is used, device optics are designed to accommodate the index of refraction of the intermediate material or layer.

The embodiment shown in FIG. 66 includes a lightpipe which draws light from the phone's LED and redirects it for the desired illumination. This lightpipe can have a variety of designs for desired illumination, including uniform illumination, structured light (to obliquely highlight wrinkles, for example). The attachment could also contain onboard LEDs or other light sources, with or without onboard power. Although the light sources described herein use LED to describe the light sources in mobile phones and attachments, a variety of light sources may be compatible.

Dual source (and higher number) illumination systems like that of the iPhone 5S present a new opportunity for hardware and software to form a powerful system. Another embodiment includes distinct light-directing features over different LEDs (or parts of a multipart LED), which can provide distinct illumination characteristics. For example, the system may be configured to control which of the handset lights is on; one may have a spectral, polarization, intensity, or holographic filter, while another may have a physical lightpipe which provides alternative desired illumination, or any combination of modification features over the light sources. This provides control over the illumination design, without the user having to flip a switch, move a filter, or otherwise be involved in modifying the illumination.

In the device shown in FIG. 66, the illumination system includes a polarizer at the distal end (nearest to the sample plane), and another polarizer over the camera in a perpendicular configuration. This is very helpful in reducing glare on the skin surface. Calibration may be important in many applications of the system, especially for longitudinal image capture, and embodiments where additional light from the environment may be present. The device can include one or more reference features that alone, or in combination with the illumination system, can provide a tool for color calibration. These features may be in the field of view of the primary camera, or they can use another camera or sensor within or working with the device. For example, the device could have an on-board light meter to measure and compensate for environmental light conditions.

Image registration is very helpful for comparing longitudinal images. Both software and hardware features may be used to facilitate this image alignment. For example, a hardware reticle or other spatial reference feature may be included, which the user can align with a prominent feature on the surface. The system may provide a semi-transparent overlay of the previous image, to which the user can align the current field of view. Features like these, including magnification, polarization, spectral selection for illumination and recording, integrated calibration, and controlled illumination are all provided by the methods and apparatuses described herein, in conjunction with a mobile phone or other mobile device, or as a stand-alone system. Combined with the display and wireless transmission capabilities of the phone, this is a powerful system for diagnostic imaging. Images can be read locally by software or a person, or transmitted for remote diagnosis. In the case of remote analysis, the response can be sent back to the user along with treatment advice.

As mentioned above, another example of an apparatus as described herein includes a system for psoriasis imaging.

Skin imaging may be useful for many potential applications, such as detection and/or monitoring of: skin cancer, acne, wound healing, chronic conditions such as psoriasis and eczema, as well as skincare or cosmetic issues like color, texture, wrinkles, aging, sun spots etc. Described below are features of a system for psoriasis imaging, many of which are useful in other skin applications.

Psoriasis is a common skin condition which often results in redness and irritation. Thick, red skin with flaky silver patches are common. The apparatuses and methods described herein may provide an accessible means for anyone to capture and analyze psoriasis images, which could help evaluate the efficacy of a drug or other treatment, and provide feedback to determine the optimal dosage. In this application, the user needs high-quality images with controlled illumination, calibrated color and intensity, and reproducible longitudinal features. Oblique, structured light, or other custom illumination techniques can be useful to highlight the three-dimensional flake features. 3D images could also be achieved with the apparatus described herein, for example using a periscope-like feature of the device (e.g. a series of mirrors) that could shift into place and enable an image from a second perspective using the same camera. For handsets with two (or more) cameras, two images could be taken simultaneously. While handsets with two cameras on a single surface are still rare in the market, the back-facing and front-facing cameras may be used simultaneously to collect a 3D image of a surface, using optics, mirrors, etc. to redirect one of the camera views.

Also described herein is the capture and analysis of serial images to measure physiological response. Longitudinal (serial) images over a period of time can be immensely valuable in tracking the results of a therapeutic intervention (or natural change or healing), even before it is visible to the user or an expert. Changes in color, reduced redness for example, can be hard to detect with the subjective vision of an observer and varying light conditions. The methods and apparatuses described herein provide a system and method for capturing the necessary images or other data, combining with knowledge of the dosage or intensity of the drug or therapy applied, and evaluating changes over time according to key evaluative factors. For example, in the psoriasis application, the use of the drug can begin with the normal dosage schedule, but titration of the dosage (or application method etc.) can be adjusted based on the comparing the patient's response with the expected response curve based on other patients. The expected response curve could be predicted by taking a broad sample of patient response or identifying similarity factors with other patients to further personalize the feedback system.

The apparatuses described herein can therefore provide serial analytical images, and combine with other data about the expected results of the drug and personal characteristics of the patient to provide an improved outcome, and can also provide a means to increase the user's satisfaction and adherence with the therapy, as he or she sees subtle improvement over time that would have been difficult to perceive with the naked eye.

Although in general, discussed herein and provided in the examples are otoscope apparatuses and methods for operating them to identify and analyze specific ear regions such as the tympanic membrane, the apparatuses and methods described herein may be more generally applied to include other biological imaging systems and methods, including in particular skin (e.g., dermascope) and eye (e.g., retinascope or opthalmoscope) applications. For example, any of the methods of detecting a tympanic membrane from an image of a subject's ear canal may be adapted to provide a method of detecting a region of skin (e.g., outer layer, mole, blemish, freckle, skin tag, etc.) or as a method of detecting a region of a patient's eye (e.g., retina, sclera, cornea, anterior chamber, posterior chamber, iris, pupil, lens, vitreus humor, fovea, macula, etc.). Such methods may include receiving the image of the subject's body region (e.g., skin, eye, etc.); selecting a subset of subregions from the image; extracting a set of feature values for each of the subregions in the subset of subregions; estimating, for each individual subregion within the subset of subregions, a probability that the individual subregion is part of a predetermined body region (e.g., retina, etc.) based on the extracted sets of feature values for the individual subregion; and identifying a predetermined body region from the image using the estimated probabilities for the subregions within the subset of subregions.

Similarly, any of the methods for guiding a subject using an otoscope as described herein may be adapted to guide the use of a dermascope, retinascope, opthalmoscope, or the like, by using a characteristic body region to be observed in place of the tympanic membrane (e.g., retina, etc.). Likewise, any of the methods of displaying an image of a tympanic membrane may be adapted as described herein to provide a method of displaying an image of another region of a subject's body (e.g., retina or other eye region when using a retinascope, a skin region when using a dermascope, etc.). For example, a method of displaying an image of a region of a subject's body may include extracting a plurality of image features from a first image of a subject's body region (e.g., retina, skin, etc.), wherein the image features include color and texture data; combining the extracted features into a feature vector for the first image; identifying a plurality of similar body region images from a database of body region images by comparing the feature vector for the first image to feature vectors for images in the database of body region images; concurrently displaying the first image and the plurality of similar body region images from the database and indicating the similarity of each of the similar body region images to the first image.

Finally, any of these methods and apparatuses may be adapted to guide diagnosis. For example a method of guiding diagnosis of an eye ailment (using a retinascope) using an image may include: extracting a plurality of image features from a first image of a subject's eye (e.g., retina), wherein the image features include color and texture data; combining the extracted features into a feature vector for the first image; applying the feature vector to a trained classification model to identify a probability of each of a plurality of different diseases; and indicating the probability of each of a plurality different disease. Alternatively, the methods or apparatuses may be adapted to guide diagnosis of a skin disorder (e.g., using a dermascope), or disorder of some other body region using an appropriate imaging device.

The methods and apparatuses described herein that may be implemented on a processor, including as software, enhance the operation of the processor on which they operate. This is particularly useful in the implementations described herein in which the process is part of a mobile telecommunications device, which may efficiently locally process image data (e.g., for images taken with a scope (e.g., otoscope) coupled to the mobile telecommunications device such as a smartphone, and remotely communicate the information with a database, including an image database, and/or a medical server (e.g., medical records, hospital, clinic, or physician). The distribution of functions between the local (e.g., smartphone) and the remote (e.g., database) may allow more efficient processor usage, enhancing speed and reliability.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An automated method of guiding a subject to take an image of a tympanic membrane using an otoscope apparatus, the method comprising:
    displaying, on a display, an image from the otoscope apparatus while the otoscope apparatus is inserted into a patient's ear;
    using the otoscope apparatus to automatically detect from the image either or both of: one or more deeper regions in the image, and at least a portion of a tympanic membrane; and
    providing real-time guidance to the subject indicating a direction that the subject should orient the otoscope apparatus in the patient's ear based on either or both of the detected one or more deeper regions and the detected at least the portion of the tympanic membrane.

2. The method of claim 1, further comprising using the otoscope to detect an occlusion of an ear canal in the image, and indicating when an occlusion is detected.

3. The method of claim 1, wherein displaying on the display comprises displaying on a screen of a mobile telecommunications device.

4. The method of claim 1, further comprising using the otoscope device to detect if an ear canal in the image is not straight, and indicating that the ear canal should be straightened.

5. The method of claim 1, wherein using the otoscope apparatus to automatically detect one or more deeper regions in the image comprises: determining a field of view for the image, correcting for uneven illumination in the field of view, identifying from the field of view one or more regions of brightness below a threshold in the image, extracting features for each identified region, and determining if an identified region is deeper in the ear canal based on the extracted features.

6. The method of claim 1, wherein using the otoscope apparatus to automatically detect one or more deeper regions in the image comprises: determining a field of view for the image, converting the field of view of the image to greyscale, filtering the field of view of the image to remove small objects, and dividing the image by an average illumination value.

7. The method of claim 1, wherein using the otoscope apparatus to automatically detect one or more deeper regions in the image comprises: determining a distribution of pixel values from the image from the otoscope and identifying regions having the pixel values below a threshold percentile of the distribution.

8. The method of claim 1, wherein using the otoscope apparatus to automatically detect one or more deeper regions in the image comprises using a trained model to determine if the one or more regions are deeper regions in an ear canal.

9. The method of claim 1, wherein using the otoscope apparatus to automatically detect one or more deeper regions in the image comprises extracting features from one or more regions of the image that are not as bright as other regions and using a trained model to determine if the one or more regions are deeper regions in an ear canal, wherein the extracted features include one or more of: region area, region eccentricity, region solidity, mean intensity of the region, and mean intensity of the region in an illumination-corrected image.

10. The method of claim 1, wherein indicating a direction to orient the otoscope comprises displaying a direction on the display device.

11. The method of claim 1, further comprising using the otoscope apparatus to automatically indicate when the at least a portion of the tympanic membrane is detected.

12. The method of claim 1, wherein using the otoscope apparatus to automatically detect at least a portion of a tympanic membrane comprises: extracting a set of feature values from a plurality of subregions from the image, and estimating, for each subregion, a probability that the subregion is part of a tympanic membrane based on the extracted sets of feature values.

13. An automated method of guiding a subject to take an image of a tympanic membrane using an otoscope apparatus, the method comprising:
displaying, on a mobile phone display coupled to the otoscope, an image from the otoscope apparatus while the otoscope apparatus is inserted into a patient's ear;
using the otoscope apparatus to automatically detect one or more deeper regions in the image;
providing real-time guidance to the subject indicating a direction that the subject should orient the otoscope apparatus on the display based on the detected one or more deeper regions; and
using the otoscope to indicate when the image includes at least a portion of a tympanic membrane.

14. The method of claim 13, wherein using the otoscope to indicate when the image includes at least a portion of a tympanic membrane comprises: extracting a set of feature values from a plurality of subregions from the image, estimating, for each subregion, a probability that the subregion is part of a tympanic membrane based on the extracted sets of feature values.

15. The method of claim 13, wherein displaying on the display comprises displaying on a screen of a mobile telecommunications device.

16. The method of claim 13, wherein using the otoscope apparatus to automatically detect one or more deeper regions in the image comprises: determining a field of view for the image, correcting for uneven illumination in the field of view, identifying from the field of view one or more regions of brightness below a threshold in the image, extracting features for each identified region, and determining if an identified region is deeper in the ear canal based on the extracted features.

17. The method of claim 13, wherein using the otoscope apparatus to automatically detect one or more deeper regions in the image comprises: determining a field of view for the image, converting the field of view of the image to greyscale, filtering the field of view of the image to remove small objects, and dividing the image by an average illumination value.

18. The method of claim 13, wherein using the otoscope apparatus to automatically detect one or more deeper regions in the image comprises: determining a distribution of pixel values from the image from the otoscope and identifying regions having the pixel values below a threshold percentile of the distribution.

19. The method of claim 13, wherein using the otoscope apparatus to automatically detect one or more deeper regions in the image comprises using a trained model to determine if the one or more regions are deeper regions in an ear canal.

20. The method of claim 13, wherein using the otoscope apparatus to automatically detect one or more deeper regions in the image comprises extracting features from one or more regions of the image that are not as bright as other regions and using a trained model to determine if the one or more regions are deeper regions in an ear canal, wherein the extracted features include one or more of: region area, region eccentricity, region solidity, mean intensity of the region, and mean intensity of the region in an illumination-corrected image.

21. An automated method of guiding a subject to take an image of a tympanic membrane using an otoscope apparatus, the method comprising:
displaying, on a display, an image from the otoscope apparatus;
using the otoscope apparatus to detect one or more deeper regions in the image by:
correcting for uneven illumination in the image, identifying one or more regions of brightness below a threshold in the image, extracting features for each identified region, and determining if an identified region is deeper in the ear canal based on the extracted features;

providing real-time guidance to the subject on the display indicating a direction that the subject should orient the otoscope apparatus based on the detected one or more deeper regions; and determining if the image includes a tympanic membrane by: extracting a set of feature values from a plurality of subregions from the image, estimating, for each subregion, a probability that the subregion is part of a tympanic membrane based on the extracted sets of feature values.

22. The method of claim 21, further comprising indicating that the image includes at least a portion of the tympanic membrane.

\* \* \* \* \*